(12) United States Patent
Sparks et al.

(10) Patent No.: US 11,299,772 B2
(45) Date of Patent: *Apr. 12, 2022

(54) ASSAY SYSTEMS FOR GENETIC ANALYSIS

(71) Applicant: Ariosa Diagnostics, Inc., San Jose, CA (US)

(72) Inventors: Andrew Sparks, Emerald Hills, CA (US); Craig Struble, San Jose, CA (US); Eric Wang, Cupertino, CA (US); Arnold Oliphant, Morgan Hill, CA (US)

(73) Assignee: Ariosa Diagnostics, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/421,398

(22) Filed: May 23, 2019

(65) Prior Publication Data

US 2019/0276879 A1    Sep. 12, 2019

Related U.S. Application Data

(63) Continuation of application No. 13/205,603, filed on Aug. 8, 2011, now Pat. No. 10,308,981, which is a continuation-in-part of application No. 13/013,732, filed on Jan. 25, 2011, now abandoned.

(60) Provisional application No. 61/371,605, filed on Aug. 6, 2010.

(51) Int. Cl.
*C12Q 1/6827* (2018.01)
*C12Q 1/6862* (2018.01)
*C12Q 1/6809* (2018.01)

(52) U.S. Cl.
CPC ......... *C12Q 1/6827* (2013.01); *C12Q 1/6809* (2013.01); *C12Q 1/6862* (2013.01)

(58) Field of Classification Search
CPC ... C12Q 1/6827; C12Q 1/6809; C12Q 1/6862
See application file for complete search history.

(56) References Cited

U.S. PATENT DOCUMENTS

| | | | |
|---|---|---|---|
| 2001/0051341 A1* | 12/2001 | Lo | C12Q 1/6879 435/6.12 |
| 2002/0197618 A1* | 12/2002 | Sampson | C12Q 1/6806 435/6.12 |
| 2007/0269805 A1* | 11/2007 | Hogers | C12Q 1/6858 435/6.12 |
| 2008/0020390 A1* | 1/2008 | Mitchell | C12Q 1/6883 435/6.12 |
| 2008/0090239 A1* | 4/2008 | Shoemaker | G01N 1/405 435/6.12 |

* cited by examiner

*Primary Examiner* — Joseph G. Dauner
(74) *Attorney, Agent, or Firm* — Jennifer Rosenfield

(57) ABSTRACT

The present invention provides assay systems and methods for detection of copy number variation at one or more loci and polymorphism detection at one or more loci in a mixed sample from an individual.

18 Claims, 16 Drawing Sheets

Specification includes a Sequence Listing.

| Sample | Sample Tag | Fetal Gender | Genome Equivs. | Maternal Karyotype | Fetal Karyotype | Mater Age | GestAge (Day) | # Loci DiffPoly | % Fetal | Mean18 | Mean21 | Prop18 | Prop21 | ZStat18 | ZStat21 |
|---|---|---|---|---|---|---|---|---|---|---|---|---|---|---|---|
| 1 | TGTCCCC | M | 2293 | 46XX | 46XY | 45 | 110 | 38 | 0.210138 | 1005.426 | 999.4412 | 0.501493 | 0.498507 | 0.48436 | -0.48436 |
| 2 | ATCCTCC | F | 3593 | 46XX | 46XX | 37 | 131 | 45 | 0.096075 | 996.6228 | 998.7823 | 0.499459 | 0.500541 | -0.84491 | 0.84491 |
| 4 | GCCAACC | F | 1469 | 46XX | 46XX | 34 | 121 | 26 | 0.235051 | 991.0624 | 997.5193 | 0.498376 | 0.501624 | -1.55236 | 1.552358 |
| 5 | CCACGAC | F | 1296 | 46XX | 46XX | 36 | 129 | 36 | 0.140539 | 1010.048 | 1004.468 | 0.501385 | 0.498615 | 0.413907 | -0.41391 |
| 6 | TCCTCGT | F | 2110 | 46XX | 46XX | 33 | 136 | 24 | 0.049392 | 994.7681 | 1000.632 | 0.498531 | 0.501469 | -1.45169 | 1.451689 |
| 7 | CCTTGCT | F | 2772 | 46XX | 46XX | 43 | 111 | 42 | 0.095395 | 997.3443 | 986.4745 | 0.50274 | 0.49726 | 1.299353 | -1.29935 |
| 8 | TCACTCT | M | 2506 | 46XX | 46XY | 34 | 126 | 32 | 0.158725 | 1004.807 | 996.2886 | 0.502128 | 0.497872 | 0.899842 | -0.89984 |
| 9 | CATCTTC | M | 3996 | 46XX | 46XY | 36 | 121 | 34 | 0.110817 | 1005.714 | 1002.283 | 0.500854 | 0.499146 | 0.067201 | -0.0672 |
| 10 | TTCGCCG | F | 4032 | 46XX | 46XX | 42 | 84 | 29 | 0.159776 | 999.7097 | 1000.399 | 0.499828 | 0.500172 | -0.60393 | 0.60393 |
| 11 | GTGTCCC | F | 4212 | 46XX | 46XX | 36 | 175 | 39 | 0.119147 | 1004.796 | 995.1465 | 0.502412 | 0.497588 | 1.085457 | -1.08546 |
| 12 | GCCCTTG | F | 3816 | 46XX | 46XX | 36 | 111 | 27 | 0.085664 | 1002.909 | 999.3516 | 0.500888 | 0.499112 | 0.089291 | -0.08929 |
| 13 | CTTACAC | F | 2160 | 46XX | 46XX | 41 | 123 | 40 | 0.117371 | 1002.012 | 995.0877 | 0.501734 | 0.498266 | 0.641893 | -0.64189 |
| 14 | TCGCAGC | F | 2790 | 46XX | 46XX | 51 | 125 | 36 | 0.119314 | 1008.515 | 999.3439 | 0.502284 | 0.497716 | 1.001374 | -1.00137 |
| 15 | CGGCCAT | F | 2783 | 46XX | 46XX | 51 | 125 | 50 | 0.123598 | 1005.525 | 998.867 | 0.501661 | 0.498339 | 0.594272 | -0.59427 |
| 16 | CCAGCTG | M | 2272 | 46XX | 46XY | 34 | 110 | 40 | 0.119257 | 1010.173 | 1004.256 | 0.501468 | 0.498532 | 0.468561 | -0.46856 |
| 17 | AGCACCT | M | 2401 | 46XX | 46XY | 34 | 140 | 43 | 0.111573 | 988.7338 | 986.5967 | 0.500541 | 0.499459 | -0.13768 | 0.137679 |
| 18 | CGATACC | F | 3960 | 46XX | 46XX | 41 | 126 | 27 | 0.099872 | 996.8338 | 999.2182 | 0.499403 | 0.500597 | -0.88162 | 0.88162 |
| 19 | CCCGAAT | M | 3816 | 46XX | 46XY | 37 | 133 | 30 | 0.095735 | 999.3982 | 991.0248 | 0.502103 | 0.497897 | 0.883556 | -0.88356 |
| 20 | CCCAGGG | M | 3474 | 46XX | 46XY | 38 | 123 | 32 | 0.115184 | 1006.395 | 992.8395 | 0.50339 | 0.49661 | 1.724514 | -1.72451 |
| 21 | CAGCACG | M | 1080 | 46XX | 46XY | 38 | 97 | 28 | 0.13036 | 994.7498 | 1003.364 | 0.497844 | 0.502156 | -1.90014 | 1.900139 |

FIG. 8

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 22 | CTCTATG | M | 2002 | 46XX | 46XY | 30 | 123 | 30 | 0.08322 | 994.7936 | 999.994 | 0.498697 | 0.501303 | -1.3432 | 1.343199 |
| 23 | ACTTTIAC | M | 3042 | 46XX | 46XY | 35 | 130 | 33 | 0.138751 | 1004.97 | 1003.101 | 0.500465 | 0.499535 | -0.18713 | 0.187128 |
| 24 | CGTATCG | F | 1922 | 46XX | 46XX | 23 | 159 | 29 | 0.254234 | 1003.218 | 1006.4 | 0.499208 | 0.500792 | -1.00868 | 1.008678 |
| 25 | AACCATT | M | 3708 | 46XX | 46XY | 38 | 148 | 31 | 0.145101 | 996.0673 | 995.7268 | 0.500085 | 0.499915 | -0.43538 | 0.435383 |
| 26 | CTGGGGC | M | 4032 | 46XX | 46XY | 30 | 126 | 27 | 0.077438 | 1005.191 | 1003.628 | 0.500389 | 0.499611 | -0.23694 | 0.23694 |
| 27 | TGCCGAG | F | 2383 | 46XX | 46XX | 35 | 138 | 32 | 0.131712 | 996.445 | 1002.698 | 0.498436 | 0.501564 | -1.51345 | 1.513451 |
| 28 | ATACCAG | F | 4104 | 46XX | 46XX | 23 | 99 | 33 | 0.099894 | 991.6721 | 1001.903 | 0.497434 | 0.502566 | -2.16839 | 2.168385 |
| 29 | GAAACCG | F | 2437 | 46XX | 46XX | 33 | 149 | 25 | 0.067606 | 1004.187 | 1006.778 | 0.499356 | 0.500644 | -0.91231 | 0.912305 |
| 30 | AAAGGCC | F | 2765 | 46XX | 46XX | 23 | 126 | 29 | 0.144098 | 1001.308 | 995.2881 | 0.501508 | 0.498492 | 0.494093 | -0.49409 |
| 31 | TCTAATT | M | 2416 | 46XX | 46XY | 23 | 119 | 28 | 0.105371 | 1006.535 | 1005.069 | 0.500364 | 0.499636 | -0.25309 | 0.25309 |
| 32 | GTTGATC | M | 2653 | 46XX | 46XY | 34 | 148 | 29 | 0.164518 | 1003.738 | 998.0583 | 0.501419 | 0.498581 | 0.435957 | -0.43596 |
| 33 | GATGTCT | M | 7488 | 46XX | 46XY | 36 | 148 | 21 | 0.056835 | 1012.154 | 1002.257 | 0.502456 | 0.497544 | 1.114241 | -1.11424 |
| 34 | AGTCTGT | M | 2653 | 46XX | 46XY | 26 | 140 | 39 | 0.21197 | 1004.959 | 996.9646 | 0.501997 | 0.498003 | 0.813799 | -0.8138 |
| 35 | AATTCTG | F | 3780 | 46XX | 46XX | 35 | 133 | 43 | 0.259642 | 997.0006 | 997.6736 | 0.499831 | 0.500169 | -0.60149 | 0.601493 |
| 36 | CTAAGTT | M | 8136 | 46XX | 46XY | 26 | 151 | 33 | 0.082773 | 1007.02 | 1006.742 | 0.500069 | 0.499931 | -0.44599 | 0.445992 |
| 37 | GGCGGTT | M | 2228 | 46XX | 46XY | 37 | 114 | 37 | 0.15551 | 1004.912 | 1003.615 | 0.500323 | 0.499677 | -0.28021 | 0.280209 |
| 38 | TATAGGC | F | 4248 | 46XX | 46XX | 27 | 165 | 48 | 0.064569 | 1014.599 | 995.8518 | 0.504662 | 0.495338 | 2.556064 | -2.55606 |
| 39 | TAGGTAC | M | 3960 | 46XX | 46XY | 35 | 124 | 41 | 0.167184 | 997.8251 | 998.4044 | 0.499855 | 0.500145 | -0.58608 | 0.586081 |
| 40 | CAATTGG | F | 4140 | 46XX | 46XX | 24 | 127 | 43 | 0.129398 | 997.6805 | 996.6003 | 0.500271 | 0.499729 | -0.31423 | 0.314232 |
| 41 | TCATAAG | M | 4320 | 46XX | 46XY | 39 | 139 | 29 | 0.227198 | 1002.31 | 991.6654 | 0.502669 | 0.497331 | 1.253298 | -1.2533 |
| 42 | GAACGGT | F | 3744 | 46XX | 46XX | 38 | 118 | 39 | 0.094147 | 1007.442 | 994.0998 | 0.503333 | 0.496667 | 1.687191 | -1.68719 |

FIG. 8 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 43 | AAGGCGT | F | 6984 | 46XX | 46XX | 37 | 130 | 36 | 0.228387 | 998.8644 | 995.701 | 0.500793 | 0.499207 | 0.027059 | -0.02706 |
| 44 | AGGAATC | F | 5112 | 46XX | 46XX | 18 | 188 | 39 | 0.244261 | 1001.465 | 995.804 | 0.501417 | 0.498583 | 0.435058 | -0.43506 |
| 45 | AACATAG | F | 3503 | 46XX | 46XX | 41 | 141 | 22 | 0.106969 | 999.5094 | 990.8389 | 0.502178 | 0.497822 | 0.932375 | -0.93238 |
| 46 | TTTGGAT | F | 2606 | 46XX | 46XX | 39 | 143 | 32 | 0.196098 | 1001.959 | 1000.069 | 0.500472 | 0.499528 | -0.18279 | 0.182795 |
| 47 | TTGATGT | F | 5292 | 46XX | 46XX | 36 | 111 | 30 | 0.109084 | 1004.708 | 1002.777 | 0.500481 | 0.499519 | -0.17694 | 0.176939 |
| 48 | ATGGTTG | M | 5184 | 46XX | 46XY | 24 | 160 | 40 | 0.060517 | 1010.204 | 1006.291 | 0.50097 | 0.49903 | 0.143003 | -0.143 |
| 49 | GGGTAGT | M | 3996 | 46XX | 46XY | 23 | 153 | 30 | 0.151707 | 1003.952 | 998.371 | 0.501394 | 0.498606 | 0.419553 | -0.41955 |
| 50 | AGATGAT | F | 5256 | 46XX | 46XX | 26 | 118 | 26 | 0.126345 | 998.1654 | 996.1826 | 0.500497 | 0.499503 | -0.16635 | 0.166347 |
| 51 | GTGAAAG | M | 4068 | 46XX | 46XY | 29 | 140 | 29 | 0.214532 | 1004.428 | 996.9586 | 0.501866 | 0.498134 | 0.728436 | -0.72844 |
| 52 | AGTGAAG | M | 11412 | 46XX | 46XY | 18 | 196 | 24 | 0.140258 | 1007.84 | 998.7992 | 0.502253 | 0.497747 | 0.9811 | -0.9811 |
| 53 | ACAACGC | M | 3146 | 46XX | 46XY | 21 | 147 | 32 | 0.180869 | 1010.525 | 999.8358 | 0.502659 | 0.497341 | 1.24639 | -1.24639 |
| 54 | GACGAGG | F | 5508 | 46XX | 46XX | 35 | 114 | 32 | 0.053622 | 994.8149 | 1005.452 | 0.497341 | 0.502659 | -2.22916 | 2.229159 |
| 55 | GGAATAC | F | 6624 | 46XX | 46XX | 28 | 140 | 37 | 0.21238 | 999.7187 | 1006.639 | 0.498275 | 0.501725 | -1.61846 | 1.618464 |
| 56 | GTTCGCG | M | 6192 | 46XX | 46XY | 44 | 115 | 25 | 0.083131 | 1009.487 | 999.2224 | 0.502555 | 0.497445 | 1.178758 | -1.17876 |
| 57 | GTCTTAT | F | 7056 | 46XX | 46XX | 25 | 115 | 37 | 0.135201 | 1005.611 | 996.4 | 0.5023 | 0.4977 | 1.01226 | -1.01226 |
| 58 | TAGTGTT | F | 5148 | 46XX | 46XX | 22 | 99 | 38 | 0.124127 | 996.363 | 999.6895 | 0.499167 | 0.500833 | -1.03587 | 1.035871 |
| 59 | TGCTTTC | M | 4104 | 46XX | 46XY | 30 | 197 | 28 | 0.310846 | 1004.509 | 1009.571 | 0.498743 | 0.501257 | -1.31256 | 1.312564 |
| 60 | TCTGTGG | M | 5364 | 46XX | 46XY | 27 | 122 | 26 | 0.118328 | 997.1746 | 992.0824 | 0.50128 | 0.49872 | 0.345307 | -0.34531 |
| 61 | TGGGCTC | F | 3636 | 46XX | 46XX | 28 | 178 | 30 | 0.158146 | 989.5388 | 999.8624 | 0.497405 | 0.502595 | -2.18709 | 2.187092 |
| 62 | TGAGTAT | M | 17856 | 46XX | 46XY | NA | NA | 45 | 0.064088 | 993.7189 | 996.5081 | 0.499299 | 0.500701 | -0.94924 | 0.949237 |
| 63 | TGCAAAT | F | 5004 | 46XX | 46XX | 35 | 109 | 39 | 0.076783 | 1003.939 | 992.7595 | 0.5028 | 0.4972 | 1.33858 | -1.33858 |

FIG. 8 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 64 | TATCAAT | M | 8712 | 46XX | 46XY | 35 | 119 | 33 | 0.077373 | 1004.37 | 996.8203 | 0.501886 | 0.498114 | 0.741595 | -0.74159 |
| 65 | TAAGAGT | F | 2552 | 46XX | 46XX+13 | 35 | 90 | 41 | 0.144442 | 999.7136 | 988.3962 | 0.502846 | 0.497154 | 1.369064 | -1.36906 |
| 66 | TAAAGAT | F | 7668 | 46XX | 46XX+13 | 30 | 141 | 37 | 0.057703 | 998.6741 | 990.8426 | 0.501968 | 0.498032 | 0.795151 | -0.79515 |
| 67 | TCTGCAC | M | 3996 | 46XX | 46XY+13 | 35 | 161 | 26 | 0.21564 | 1001.317 | 998.1811 | 0.500784 | 0.499216 | 0.021337 | -0.02134 |
| 68 | GTGGGCT | F | 7560 | 46XX | 46XX+21 | 35 | 125 | 28 | 0.092562 | 983.1548 | 1024.755 | 0.489641 | 0.510359 | -7.2619 | 7.2619 |
| 69 | GTGACTT | F | 13248 | 46XX | 46XX+21 | 19 | 132 | 30 | 0.085949 | 980.027 | 1020.997 | 0.489763 | 0.510237 | -7.18225 | 7.182254 |
| 70 | GGTCAGC | F | 7452 | 46XX | 46XX+21 | 40 | 91 | 31 | 0.056151 | 990.5328 | 1011.076 | 0.494868 | 0.505132 | -3.84532 | 3.845324 |
| 71 | GGGCGAC | F | 5508 | 46XX | 46XY+21 | 18 | 166 | 32 | 0.140102 | 965.1286 | 1037.339 | 0.48197 | 0.51803 | -12.2758 | 12.27579 |
| 73 | GGCTAAC | M | 5184 | 46XX | 46XY+18 | 29 | 147 | 29 | 0.157072 | 1044.147 | 960.7049 | 0.52081 | 0.47919 | 13.11012 | -13.1101 |
| 75 | GAGTGCG | M | 2689 | 46XX | 46XX+18 | 40 | 93 | 24 | 0.129256 | 1038.787 | 958.3378 | 0.520141 | 0.479859 | 12.67306 | -12.6731 |
| 76 | GAATGAC | F | 7632 | 46XX | 46XX+18 | 43 | 133 | 24 | 0.048391 | 1015.894 | 982.9916 | 0.50823 | 0.49177 | 4.887983 | -4.88798 |
| 78 | GCTTGTG | F | 7128 | 46XX | 46XX+18 | 25 | 128 | 30 | 0.06035 | 1018.978 | 985.6703 | 0.508308 | 0.491692 | 4.938613 | -4.93861 |
| 79 | GCAGAAC | M | 4464 | 46XX | 46XY+18 | 40 | 82 | 31 | 0.082749 | 1022.638 | 974.749 | 0.511988 | 0.488012 | 7.344068 | -7.34407 |
| 80 | ATGGAAT | F | 2100 | 46XX | 46XX+18 | 42 | 98 | 39 | 0.094043 | 1023.162 | 977.342 | 0.511452 | 0.488548 | 6.993832 | -6.99383 |
| 81 | ATCAGAT | M | 4176 | 46XX | 46XY+21 | 35 | 147 | 33 | 0.148476 | 957.3759 | 1038.729 | 0.479622 | 0.520378 | -13.8102 | 13.81016 |
| 82 | AGTTACT | M | 4500 | 46XX | 46XY+21 | 39 | 124 | 19 | 0.205496 | 952.9748 | 1049.25 | 0.475958 | 0.524042 | -16.205 | 16.20502 |
| 83 | AGTAGAC | M | 8640 | 46XX | 46XY+21 | 37 | 125 | 30 | 0.130907 | 973.3572 | 1028.835 | 0.486146 | 0.513854 | -9.54628 | 9.546281 |
| 84 | AGGTCTT | M | 16092 | 46XX | 46XY+21 | 43 | 94 | 35 | 0.126545 | 976.6225 | 1029.797 | 0.486749 | 0.513251 | -9.1521 | 9.152097 |
| 85 | AGGATAT | M | 4212 | 46XX | 46XY+21 | 40 | 157 | 24 | 0.119821 | 969.1251 | 1025.932 | 0.485763 | 0.514237 | -9.79643 | 9.796425 |
| 86 | AGGACGG | M | 4644 | 46XX | 46XY+21 | 33 | 97 | 31 | 0.053737 | 992.2248 | 1011.59 | 0.495168 | 0.504832 | -3.64941 | 3.649405 |
| 87 | AGAGATT | M | 4320 | 46XX | 46XY+21 | 31 | 119 | 37 | 0.08022 | 978.7159 | 1014.132 | 0.491114 | 0.508886 | -6.29894 | 6.298937 |

FIG. 8 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 89 | AGCTGCC | F | 6768 | 46XX | 46XX+21 | 31 | 98 | 35 | 0.126696 | 963.2256 | 1024.818 | 0.484509 | 0.515491 | -10.616 | 10.61595 |
| 90 | AGCGCTG | M | 1375 | 46XX | 46XY+21 | 36 | 162 | 36 | 0.133202 | 961.1764 | 1032.034 | 0.482225 | 0.517775 | -12.1088 | 12.10879 |
| 91 | AGCATGC | M | 5155 | 46XX | 46XY+21 | 41 | 154 | 37 | 0.095349 | 967.2823 | 1017.613 | 0.487322 | 0.512678 | -8.77777 | 8.777767 |
| 92 | AATGGTT | F | 2549 | 46XX | 46XX+21 | 41 | 119 | 32 | 0.09505 | 965.3134 | 1025.717 | 0.484831 | 0.515169 | -10.4056 | 10.4056 |
| 93 | AAGTAAG | F | 9216 | 46XX | 46XX+21 | 42 | 253 | 32 | 0.209915 | 946.0902 | 1052.948 | 0.473273 | 0.526727 | -17.96 | 17.96002 |
| 94 | AAATAGC | F | 2041 | 46XX | 46XX+21 | 36 | 161 | 32 | 0.102554 | 973.7957 | 1025.545 | 0.487058 | 0.512942 | -8.94982 | 8.949816 |
| 95 | AAATCCT | M | 1843 | 46XX | 46XY+21 | 42 | 91 | 35 | 0.137238 | 965.4467 | 1031.552 | 0.483449 | 0.516551 | -11.309 | 11.30904 |

FIG. 8 (cont.)

SEQUENCE LISTING

<160> NUMBER OF SEQ ID NOS: 8

<210> SEQ ID NO 1
<211> LENGTH: 24
<212> TYPE: DNA
<213> ORGANISM: Artficial Sequence
<220> FEATURE:
<223> OTHER INFORMATION: Synthetic oligonucleotide

<400> SEQUENCE: 1
tacaccggcg ttatgcgtcg agac                                          24

<210> SEQ ID NO 2
<211> LENGTH: 24
<212> TYPE: DNA
<213> ORGANISM: Artficial Sequence
<220> FEATURE:
<223> OTHER INFORMATION: Synthetic oligonucleotide

<400> SEQUENCE: 2
attgcgggga ccgatgatcg cgtc                                          24

<210> SEQ ID NO 3
<211> LENGTH: 48
<212> TYPE: DNA
<213> ORGANISM: Artficial Sequence
<220> FEATURE:
<223> OTHER INFORMATION: Synthetic Oligonucleotide

<400> SEQUENCE: 3
taatgatacg gcgaccaccg agatctacac cggcgttatg cgtcgaga               48

<210> SEQ ID NO 4
<211> LENGTH: 53
<212> TYPE: DNA
<213> ORGANISM: Artficial Sequence
<220> FEATURE:
<223> OTHER INFORMATION: Synthetic oligonucleotide
<220> FEATURE:
<221> NAME/KEY: misc_feature
<222> LOCATION: (26)..(26)
<223> OTHER INFORMATION: n = a, c, g, or t

<400> SEQUENCE: 4
tcaagcagaa gacggcatac gagatnaaac gacgcgatca tcggtccccg caa          53

<210> SEQ ID NO 5
<211> LENGTH: 21
<212> TYPE: DNA
<213> ORGANISM: Artficial Sequence
<220> FEATURE:
<223> OTHER INFORMATION: Synthetic Oligonucleotide

<400> SEQUENCE: 5
taatgatacg gcgaccaccg a                                             21

<210> SEQ ID NO 6
<211> LENGTH: 25
<212> TYPE: DNA
<213> ORGANISM: Artficial Sequence
<220> FEATURE:
<223> OTHER INFORMATION: Synthetic oligonucleotide

<400> SEQUENCE: 6
atctcgtatg ccgtcttctg cttga                                         25

<210> SEQ ID NO 7
<211> LENGTH: 48
<212> TYPE: DNA
<213> ORGANISM: Artficial Sequence
<220> FEATURE:
<223> OTHER INFORMATION: Synthetic Oligonucleotide

<400> SEQUENCE: 7

```
aatgatacgg cgaccaccga gatctacacc ggcgttatgc gtcgagac                    48

<210> SEQ ID NO 8
<211> LENGTH: 60
<212> TYPE: DNA
<213> ORGANISM: Artficial Sequence
<220> FEATURE:
<223> OTHER INFORMATION: Synthetic oligonucleotide
<220> FEATURE:
<221> NAME/KEY: misc_feature
<222> LOCATION: (26)..(32)
<223> OTHER INFORMATION: n = a, c, g, or t

<400> SEQUENCE: 8
tcaagcagaa gacggcatac gagatnnnnn nnaaacgacg cgatcatcgg tccccgcaat      60
```

ASSAY SYSTEMS FOR GENETIC ANALYSIS

CROSS-REFERENCE TO RELATED APPLICATIONS

The present application is a continuation of U.S. application Ser. No. 13/205,603, filed Aug. 8, 2011, which claims priority to U.S. application Ser. No. 13/013,732, filed Jan. 25, 2011, which claims priority to U.S. Provisional Application Ser. No. 61/371,605, filed Aug. 6, 2010, each of which are herein incorporated by reference incorporated herein in their entireties by this reference.

FIELD OF THE INVENTION

This invention relates to assay systems for identifying copy number variation in mixed samples in a single assay.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions. Recent advances in diagnostics have focused on less invasive mechanisms for determining disease risk, presence and prognosis. Diagnostic processes for determining genetic anomalies have become standard techniques for identifying specific diseases and disorders, as well as providing valuable information on disease source and treatment options.

The identification of cell free nucleic acids in biological samples such as blood and plasma allow less invasive techniques such as blood extraction to be used in making clinical decisions. For example, cell free DNA from malignant solid tumors has been found in the peripheral blood of cancer patients; individuals who have undergone transplantation have cell free DNA from the transplanted organ present in their bloodstream; and cell-free fetal DNA and RNA have been found in the blood and plasma of pregnant women. In addition, detection of nucleic acids from infectious organisms, such as detection of viral load or genetic identification of specific strains of a viral or bacterial pathogen, provides important diagnostic and prognostic indicators. Cell free nucleic acids from a source separate from the patient's own normal cells can thus provide important medical information, e.g., about treatment options, diagnosis, prognosis and the like.

The sensitivity of such testing is often dependent upon the identification of the amount of nucleic acid from the different sources, and in particular identification of a low level of nucleic acid from one source in the background of a higher level of nucleic acids from a second source. Detecting the contribution of the minor nucleic acid species to cell free nucleic acids present in the biological sample can provide accurate statistical interpretation of the resulting data.

There is thus a need for processes for calculating copy number variation (CNV) in one or more genomic regions in a biological sample using information on contribution of nucleic acids in the sample. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The methods of the invention comprise a single assay system with the ability to determine contribution of a major source and/or a minor source within a sample from an individual and determining copy number information for one or more genomic regions within a single source to determine a value difference for the genomic region compared to the contribution of the source of the loci in the mixed sample. The present invention utilizes a single assay system that utilizes both non-polymorphic and polymorphic detection to determine source contribution and copy number variations (CNVs) from a single source within the mixed sample. Determination of contribution of the major and/or minor source within the sample can provide information on the presence of sufficient genetic material from both sources to allow adequate identification of genomic regions for determination of CNV in the mixed samples.

In one aspect, the assay system utilizes amplification and detection of selected loci in a mixed sample from an individual to calculate source contribution and to identify the copy number of one or more genomic regions. In one specific aspect, the invention provides single assay systems with the ability to determine the contribution of nucleic acids from a major and/or minor source in the mixed sample and the presence or absence of CNVs at one or more genomic regions from a single source in a mixed sample. The assay system can specifically detect copy number of genomic regions present in two or more sources within the mixed sample. For determination of contribution, the selected loci from one source are distinguished from the selected loci of at least one other source in the mixed sample. For determination of copy number variation of a genomic region, the selected loci can but do not need to be distinguished as to source contribution, as copy number variation can be detected by comparison of the levels of two or more genomic regions within a mixed sample. Preferably, the cell free nucleic acids analyzed in the assay system are cell free DNA (cfDNA).

Thus in a first implementation, the invention provides a single assay system for 1) determining the contribution of a major source and/or a minor source in a mixed sample using frequency data derived from two or more informative loci; 2) determining the frequency of one or more genomic regions in the major and minor source; and 3) identifying the presence or absence of a CNV for one or more genomic regions in the major and/or minor source. Preferably, the CNV identification is based on the comparison of the copy number of two or more genomic regions from the major and/or minor source in the mixed sample.

Preferably, the nucleic acids analyzed using the systems of the invention are cell free nucleic acids. More preferably, the nucleic acids analyzed in the assay system comprise cell free DNA (cfDNA).

In another specific aspect, the invention provides an assay system for calculation of source contribution and detection of the presence or absence of CNVs in one or more genomic regions within a mixed sample, the assay comprising the steps of introducing a first set of fixed sequence oligonucleotides to a mixed sample under conditions that allow the fixed oligonucleotides to specifically hybridize to complementary regions on one or more loci in or associated with a genomic region; introducing a second set of fixed sequence oligonucleotides to the mixed sample under conditions that allow the fixed oligonucleotides to specifically hybridize to complementary regions on two or more informative loci; ligating the hybridized oligonucleotides to create contiguous ligation products complementary to the selected loci; amplifying the contiguous ligation products to create amplification products; and detecting the amplification products. The detection of the amplification products is used to calculate source contribution and the copy number of one or more genomic regions in the mixed sample.

The sets of fixed oligonucleotides comprise two or more oligonucleotides that hybridize to contiguous regions of the genomic regions or the informative loci. In some preferred aspects, sets of loci are interrogated for CNV, and are indicative of an amplification of a larger genomic region, e.g., all or part of a chromosome. Preferably, the assay systems can distinguish the copy number of these loci between a major source and a minor source within a mixed sample. Levels of selected loci can be determined for a genomic region of interest and compared to the quantities of loci of one or more other genomic regions of interest and/or one or more reference genomic regions to detect potential CNVs based on loci frequencies in the mixed sample.

Detection of chromosomal abnormality in a sample can be based on detection of CNV for multiple selected loci located on or associated with a single chromosome from a minor and/or major source. Thus, in another specific aspect, the invention provides a single assay system for 1) determining the contribution of a major source and/or a minor source in a mixed sample using frequency data derived from two or more informative loci; 2) determining the frequency of one or more genomic regions in the major and minor source; and 3) identifying the presence or absence of a chromosomal abnormality in the major and/or minor source in the mixed sample.

Thus, the invention provides an assay system for calculation of source contribution and detection of the presence or absence of a chromosomal abnormality in a mixed sample using a single assay, the assay comprising the steps of: introducing a first set of fixed sequence oligonucleotides to a mixed sample under conditions that allow the fixed sequence oligonucleotides to specifically hybridize to complementary regions on two or more loci corresponding to a first chromosome; introducing a second set of fixed sequence oligonucleotides to the mixed sample under conditions that allow the fixed oligonucleotides to specifically hybridize to complementary regions on two or more loci corresponding to a second chromosome; introducing a third set of fixed sequence oligonucleotides to the mixed sample under conditions that allow the fixed oligonucleotides to specifically hybridize to complementary regions on two or more informative loci; ligating the hybridized oligonucleotides to create contiguous ligation products complementary to the nucleic acids; amplifying the contiguous ligation products to create amplification products; and detecting the amplification products. The detection of amplification products can be used for calculation of source contribution as well as identification of chromosomal abnormalities in the mixed sample.

In a more specific aspect the assay systems of the invention are used to identify percent fetal contribution and chromosomal abnormalities in a maternal sample. The invention provides an assay system comprising the steps of: introducing a first set of fixed sequence oligonucleotides to a maternal sample under conditions that allow the fixed oligonucleotides to specifically hybridize to complementary regions on two or more loci corresponding to a first chromosome; introducing a second set of fixed sequence oligonucleotides to the maternal sample under conditions that allow the fixed oligonucleotides to specifically hybridize to complementary regions on two or more loci corresponding to a second chromosome; introducing a third set of fixed sequence oligonucleotides to the maternal sample under conditions that allow the fixed oligonucleotides to specifically hybridize to complementary regions on two or more informative loci; ligating the hybridized oligonucleotides to create contiguous ligation products complementary to the nucleic acids; amplifying the contiguous ligation products to create amplification products; and detecting the amplification products. The detection of amplification products can be used for calculation of fetal contribution as well as identification of chromosomal abnormalities in the fetal nucleic acids in the maternal sample.

In certain aspects of the invention, the fixed oligonucleotides are hybridized immediately adjacent in the contiguous region, so that they are ligated directly during the ligation step of the assay. In other aspects, however, there may be a gap of one or more nucleotides between the ends of the fixed oligonucleotides following hybridization in the contiguous region. The fixed oligonucleotides are joined by a combination of, e.g., primer extension using a polymerase and ligation.

Each set of fixed sequence nucleic acids is designed to hybridize to at least two separate regions in a selected locus. In preferred aspects, two or more separate oligos are used in a set to hybridize to these regions to provide adjacent nucleic acids complementary to the selected loci. In some aspects, however, a set can comprise a single probe with two or more distinct non-adjacent regions that are complementary to the selected loci (e.g., padlock probes), as described in more detail herein. The sets of fixed sequence oligos can be provided in the assay sequentially or simultaneously in the assay.

In certain preferred aspects, bridging oligos are used to increase specificity of the oligo sets and/or fill a gap between fixed sequence oligonucleotides. Accordingly, another specific aspect of the invention provides an assay system for calculation of source contribution and detection of the presence or absence of CNVs in one or more genomic regions within a mixed sample, the assay comprising the steps of introducing a first set of fixed sequence oligonucleotides to a mixed sample under conditions that allow the fixed oligonucleotides to specifically hybridize to complementary regions on one or more loci in or associated with a genomic region; introducing a second set of fixed sequence oligonucleotides to the mixed sample under conditions that allow the fixed oligonucleotides to specifically hybridize to complementary regions on at least one informative loci; introducing one or more bridging oligonucleotides under conditions that allow the bridging oligonucleotides to specifically hybridize to complementary regions in the loci, wherein one or more bridging oligonucleotides are complementary to a region of the loci between and immediately adjacent to the regions complementary to the fixed sequence oligonucleotides of each set; ligating the hybridized oligonucleotides to create contiguous ligation products complementary to the nucleic acids; amplifying the contiguous ligation products to create amplification products; and detecting the amplification products. Detection of the amplification products is used to calculate source contribution and the copy number of one or more genomic regions in the mixed sample.

Another specific aspect of the invention provides an assay system using bridging oligonucleotides to calculate source contribution and identify chromosomal abnormalities in a mixed sample. This assay comprises the steps of: introducing a first set of fixed sequence oligonucleotides to a mixed sample under conditions that allow the fixed oligonucleotides to specifically hybridize to complementary regions on two or more loci corresponding to a first chromosome; introducing a second set of fixed sequence oligonucleotides to the mixed sample under conditions that allow the fixed oligonucleotides to specifically hybridize to complementary regions on two or more loci corresponding to a second chromosome; introducing a third set of fixed sequence oligonucleotides to the mixed sample under conditions that allow the fixed oligonucleotides to specifically hybridize to complementary regions on two or more informative loci; introducing one or more bridging oligonucleotides under conditions that allow the bridging oligonucleotides to specifically hybridize to complementary regions in the loci, wherein one or more bridging oligonucleotides are complementary to a region of the loci between and immediately adjacent to the regions complementary to the fixed sequence oligonucleotides of each set; introducing one or more bridging oligonucleotides under conditions that allow the bridging oligonucleotides to specifically hybridize to complementary regions in the loci, wherein one or more bridging oligonucleotides are complementary to a region of the loci between and immediately adjacent to the regions complementary to the fixed sequence oligonucleotides of each set; ligating the hybridized oligonucleotides to create contiguous ligation products complementary to the nucleic acids; amplifying the contiguous ligation products to create amplification products; and detecting the amplification products. The detection of amplification products can be used for calculation of source contribution (such as fetal contribution in a maternal sample), as well as identification of chromosomal abnormalities in the mixed sample.

In certain aspects of the invention, the fixed oligonucleotides are hybridized immediately adjacent to the bridging oligos, so that they are all ligated directly during the ligation step of the assay. In other aspects, however, there may be a gap of one or more nucleotides between the end of one or both of the fixed oligonucleotides and the bridging oligo following hybridization of the bridging oligo. The fixed oligonucleotides and the bridging oligo are joined by a combination of, e.g., primer extension using a polymerase and ligation.

It is an important feature that the multiplexed assays of the invention allow the analysis of 5 or more, preferably 10 or more, preferably 16 or more, preferably 20 or more, preferably 30 or more, preferably 32 or more, preferably 40 or more, preferably 48 or more, preferably 50 or more, preferably 60 or more, preferably 70 or more, preferably 80 or more, preferably 90 or more, and more preferably 96 or more selected loci simultaneously. These selected loci may be different loci from a single sample, or they may be loci from two or more mixed samples. In the latter case, at least one of the two fixed sequence oligonucleotides used for analysis of a selected locus will comprise a sample identifier (e.g., a "sample index") that will allow the locus to be associated with a particular sample. Alternatively, a sample index may be added during amplification of the ligation product by using a primer comprising the sample index.

In preferred aspects, the interrogation of these loci utilizes universal amplification techniques that allow amplification of multiple loci in a single amplification reaction. The selected nucleic acids for contribution calculation and detection of CNV and/or chromosomal abnormalities in the assay system of the invention can be amplified using universal amplification methods following the initial selective amplification from the mixed sample. The use of universal amplification allows multiple nucleic acids regions from a single or multiple samples to be amplified using a single or limited number of amplification primers, and is especially useful in amplifying multiple selected regions in a single reaction. In a preferred aspect, the universal primer regions are used in sequence determination of the amplification products. In another preferred aspect, the same universal primer regions are used in the fixed sequence oligonucleotides used for detection of genomic regions and the fixed sequence oligonucleotides used for detection of polymorphisms.

Thus, in a specific aspect of the invention, sequences complementary to primers for use in universal amplification are introduced to the selected loci during or following selective amplification. Preferably such sequences are introduced to the ends of such selected nucleic acids, although they may be introduced in any location that allows identification of the amplification product from the universal amplification procedure.

In certain preferred aspects, one or both of the primers used comprise a sample index or other identifier. In a specific aspect, a sample index is included in one or more of the universal primers. The sample index is incorporated into the amplification products, and amplification products from different samples may then be combined. The sample index is detected concurrently with the detection of the CNV or chromosomal abnormality and the detection of polymorphism such that the CNV and polymorphism may be properly assigned to the sample of origin.

In certain aspects, the assay system multiplexes loci interrogation using one or more common bridging oligonucleotides that are complementary to regions in two or more interrogated loci, i.e. a single bridging oligo can be used for two or more fixed oligonucleotide sets. This allows the number of bridging oligonucleotides used in the multiplexed assay system to be less than the number of loci interrogated in the assay. In certain specific aspects, the assay system uses a pool of bridging oligonucleotides that are each designed to be compatible with two or more loci interrogated using the assays system of the invention.

Frequencies of selected loci can be determined for a genomic region of interest and compared to the frequencies of loci of one or more other genomic regions of interest and/or one or more reference genomic regions to detect potential CNVs based on loci frequencies in the mixed sample.

In some instances, the chromosomal abnormality detected using is associated with gene amplification or loci expansion on a chromosome of interest. In other instances, the chromosomal abnormality is associated with a translocation resulting in the presence of an extra portion of a chromosome in the genome. In yet other instances, the chromosomal abnormality is a deletion.

In certain preferred aspects, the chromosomal abnormality is associated with aneuploidy of a chromosome of interest. For example, the most common chromosomal abnormalities in the fetus are trisomy 21, 18, 13, X and/or Y or monosomy X. In specific preferred aspects, the assay systems of the invention are used to detect such common chromosomal aneuploidies in the fetal DNA of a maternal sample.

In the assay systems of the invention, the amplification products are optionally isolated prior to detection. When isolated, they are preferably isolated as individual molecules to assist in subsequent detection. Following isolation, the amplification products can be further amplified to create identical copies of all or a portion of the individual amplification products prior to detection. Alternatively, the isolated amplification products can be further amplified to create identical copies of molecules complementary to all or a portion of the individual amplification products prior to detection.

Various methods of detection of CNVs can be employed in conjunction with the detection of the polymorphisms in the assay systems of the invention. In one general aspect, the assay system employs a method for determination of a CNV in one or more loci in a mixed sample, comprising the steps of amplifying one or more selected nucleic acids from a first genomic region of interest in a mixed sample; amplifying one or more selected nucleic acids from a second locus of interest in the mixed sample, determining the relative frequency of the selected loci, comparing the relative frequency of the selected loci, and identifying the presence or absence of a CNV based on the compared relative frequencies of the selected nucleic acids from the first and second loci. Preferably, the assay method amplifies two or more selected loci from different genomic regions, although the loci may be located in the same general genomic region for confirmation of CNVs arising from chromosomal abnormalities rather than CNVs from a single locus.

More preferably, the unhybridized fixed sequence oligonucleotides are removed prior to introduction of the bridging oligonucleotides. In some aspects, the bridging oligonucleotides are introduced simultaneously with the ligation mixture. In other aspects, the hybridization products of the fixed sequence oligonucleotides and the locus are isolated prior to introduction of the bridging oligonucleotides.

In certain specific aspects, the assay system uses a pool of bridging oligonucleotides that are each designed to be compatible with two or more loci interrogated using the assay system of the invention. In these aspects, the bridging oligonucleotides used in the multiplexed assay are preferably designed to have a $T_m$ in a range of $\pm 5°$ C., more preferably in a range of $\pm 2°$ C.

In certain aspects, the bridging oligonucleotides of are between 2-45 nucleotides in length. In a specific aspect, the bridging oligonucleotides are between 3-9 nucleotides in length. In yet another specific aspect, the oligonucleotides are between 10-30 nucleotides in length.

The loci interrogated for CNV can in some instances be indicative of a amplification of a larger genomic region, e.g., all or part of a chromosome. Preferably, the assay systems can distinguish the copy number of these loci between a major source and a minor source within a mixed sample.

In another aspect, the present invention utilizes techniques that allow the identification of both CNVs and infectious agents in a mixed sample. This may be especially helpful to monitor patients in which the clinical outcome may be compromised by the presence of an infectious agent. For example, a patient that has undergone a transplant will likely be taking immunosuppressant medication, and so more prone to infection in general. Similarly, pregnant women have changes in their immune system and thus may be more susceptible to infection with pathogens that may have an adverse effect on the mother and/or fetus. Also, certain types of cancer are associated with infectious agents (e.g., liver cancer associated with hepatitis B and C infections, cervical cancer associated with human papilloma virus infection), and identification of the infectious agents may be informative in predicting clinical outcome or determining the preferred course of medical treatment for the patient.

Thus, in certain aspects, the invention provides an assay system for calculation of source contribution, detection of the presence or absence of CNV of a genomic region, and the presence or absence of an infectious agent in a mixed sample using a single assay, the assay comprising the steps of: of introducing a first set of fixed sequence oligonucleotides to a mixed sample under conditions that allow the fixed oligonucleotides to specifically hybridize to complementary regions on one or more loci in or associated with a genomic region; introducing a second set of fixed sequence oligonucleotides to the mixed sample under conditions that allow the fixed oligonucleotides to specifically hybridize to complementary regions on at least one informative loci; introducing a third set of fixed sequence oligonucleotides to the mixed sample under conditions that allow the fixed sequence oligonucleotides to specifically hybridize to complementary regions on loci indicative of an infectious agent; ligating the hybridized oligonucleotides to create a contiguous ligation product complementary to the loci; amplifying the contiguous ligation product to create amplification products; and detecting the amplification products. The detection of the amplification products correlates to copy number of the genomic region and the presence or absence of an infectious agent in the mixed sample.

In another general aspect, the assay system employs a method for determining the presence or absence of a chromosomal abnormality associated with CNV in a genomic region, comprising the steps of amplifying one or more selected loci from a first chromosome of interest in a mixed sample; amplifying one or more selected loci from a second chromosome of interest in the mixed sample, determining the relative frequency of the selected regions from the first and second chromosomes of interest, comparing the relative frequency of the selected regions from the first and second chromosomes of interest, and identifying the presence or absence of an abnormality based on the compared relative frequencies of the selected regions. Preferably, two or more nucleic acids regions are selected from each chromosome, and more preferably five or more loci are selected from each chromosome.

In yet another general aspect, the assay system employs a method for determination of the presence or absence of an aneuploidy in a mixed sample from an individual, comprising the steps of amplifying two or more selected loci in the cfDNA corresponding to a first chromosome of interest in a mixed sample; amplifying two or more selected loci in the cfDNA corresponding to a second chromosome of interest in the mixed sample, determining the relative frequency of the selected regions from the first and second chromosomes of interest, comparing the relative frequency of the selected regions from the first and second chromosomes of interest, and identifying the presence or absence of an aneuploidy based on the compared relative frequencies of the selected regions. In a specific aspect, the loci of the first and second chromosomes are amplified in a single reaction, and preferably in a single reaction contained within a single vessel.

Preferably, the assay system detects the presence or absence of loci in samples that can be easily obtained from a subject, such as blood, plasma, serum and the like. In one general aspect, the assay system utilizes detection of selected regions in cfDNA in a mixed sample. In one more specific aspect, the assay system utilizes detection of selected regions in cfDNA of a mixed sample from an individual to identify the presence or absence of CNVs in a genomic region and the presence or absence of a polymorphism in one or more loci. Copy number within a genomic region can be determined based on detection of quantities of selected loci and comparison to the quantities of selected loci from another genomic region and/or to the quantities of selected loci from a reference genomic region. In a particular aspect, the ratio of the frequencies of the nucleic acid are compared to a reference mean ratio that has been determined for a statistically significant population of genetically "normal" subjects, i.e. subjects that do not have a CNV associated with the particular loci interrogated in the assay system.

In a preferred aspect of the invention, the amplification products corresponding to the selected nucleic acids are isolated as individual molecules for analysis of the selected loci. These individual amplification products are isolated from one another, and preferably physically isolated (e.g., on a substrate or in individual vessels). The individual molecules may be further amplified following isolation to make multiple, identical copies of the amplification product, a portion thereof, or a nucleic acid complementary to the amplification product or a portion thereof.

In a preferred aspect, the individual amplification products are analyzed through sequence determination. In other aspects, the individual amplification products are analyzed using hybridization techniques.

It is a feature of the present invention that copy number of the selected loci can be detected using non-polymorphic detection methods, i.e., detection methods that are not dependent upon the presence or absence of a particular polymorphism to identify the selected nucleic acid region. In a preferred aspect, the assay detection systems utilize non-polymorphic detection methods to "count" the relative numbers of selected loci present in a mixed sample. These numbers can be utilized to determine if, statistically, a mixed sample is likely to have a CNV in a genomic region in a major and/or minor source within the mixed sample. Similarly, these numbers can be utilized to determine, if statistically, nucleic acids from the major source and/or minor source has one or more polymorphisms. Such information can be used to identify a particular pathology or genetic disorder, to confirm a diagnosis or recurrence of a disease or disorder, to determine the prognosis of a disease or disorder, to assist in determining potential treatment options, etc.

In some aspects, the methods for determination of aneuploidy used by the assay system measure the copy number variation of multiple selected loci from two or more chromosomes in a sample. The levels of the different selected loci corresponding to specific chromosomes can be individually quantified and compared to determine the presence or absence of a chromosomal aneuploidy in one or more cell source in a mixed sample. The individually quantified regions may undergo a normalization calculation or the data may be subjected to outlier exclusion prior to comparison to determine the presence or absence of an aneuploidy in a mixed sample.

In other aspects, the relative frequencies of the selected loci are used to determine a chromosome frequency of the first and second chromosomes of interest, and the presence or absence of an aneuploidy is based on the compared chromosome frequencies of the first and second chromosomes of interest.

In yet other aspects, the relative frequencies of the selected loci are used to determine a chromosome frequency of a chromosome of interest and a reference chromosome, and the presence or absence of an aneuploidy is based on the compared chromosome frequencies of the chromosome of interest and the reference chromosome.

As the assay system of the invention is preferably configured as a highly multiplexed system, multiple loci from a single or multiple chromosomes within an individual sample and/or multiple samples can be analyzed simultaneously. In such multiplexed systems, the samples can be analyzed separately, or they may be initially pooled into groups of two or more for analysis of larger numbers of samples. When pooled data is obtained, such data is preferably identified for the different samples prior to analysis of aneuploidy. In some aspects, however, the pooled data may be analyzed for potential CNVs, and individual samples from the group subsequently analyzed if initial results indicates that a potential aneuploidy is detected within the pooled group.

In certain aspects, the assay systems utilize one or more indices that provide information on specific samples. For example, an index can be used in selective or universal amplification that is indicative of a sample from which the nucleic acid was amplified.

In one particular aspect, the selected loci are isolated prior to detection. The selected loci can be isolated from the mixed sample using any means that selectively isolate the particular nucleic acids present in the mixed sample for analysis, e.g., hybridization, amplification or other form of sequence-based isolation of the nucleic acids from the mixed sample. Following isolation, the selected nucleic acids are individually distributed in a suitable detection format, e.g., on a microarray or in a flow cell, for determination of the sequence and/or relative quantities of each selected nucleic acid in the mixed sample. The relative quantities of the detected nucleic acids are indicative of the number of copies of chromosomes that correspond to the selected nucleic acids present in the mixed sample.

Following isolation and distribution of the selected nucleic acids in a suitable format, the selected sequences are identified, e.g., through sequence determination of the selected sequence.

In one specific aspect, the invention provides an assay system for detection of the presence or absence of a fetal aneuploidy, comprising the steps of providing a mixed sample comprising maternal and fetal cfDNA, amplifying two or more selected loci from a first and second chromosome of interest in the mixed sample, amplifying two or more selected loci from the first and second chromosome of interest in the mixed sample, determining the relative frequency of the selected regions from the chromosomes of interest, comparing the relative frequency of the selected loci from the first and second chromosomes of interest, and identifying the presence or absence of a fetal aneuploidy based on the compared relative frequencies of the selected loci.

In some specific aspects, the relative frequencies of the loci from a genomic region are individually calculated, and the relative frequencies of the individual loci are compared to determine the presence or absence of a chromosomal abnormality. In other specific aspects, the relative frequencies of the selected loci are used to determine a chromosome frequency of a first and second chromosome of interest and a reference chromosome, and the copy number variation for the chromosome or a genomic region of the chromosome is based on the compared chromosome frequencies of the first and second chromosomes of interest.

The mixed sample used for analysis can be obtained or derived from any sample which contains the nucleic acid of interest to be analyzed using the assay system of the invention. For example, a mixed sample may be from any maternal fluid which comprises both maternal and fetal cell free nucleic acids, including but not limited to maternal plasma, maternal serum, or maternal blood. A mixed sample from a transplant patient would be any fluid or tissue which contains cell free nucleic acids from both the donor cells and the cells of the patient. A mixed sample from a patient with a malignancy would contain cell free nucleic acids from the patient's normal, healthy tissue as well as cell free nucleic acids from the cancerous cells.

Although preferably the assay system is used to detect cfDNA in a mixed sample, in certain aspects the DNA of interest to be analyzed using the assay system of the invention comprises DNA directly from the different cell types rather than from a mixed sample containing DNA from the major and minor cell types. Such samples can be obtained from various sources depending upon the target DNA. For example, fetal cells for analysis can be derived from samples such as amniotic fluid, placenta (e.g., the chorionic villi), and the like. Samples of donor organs can be obtained in an individual by biopsy. Infectious organisms can be isolated directly from an individual and analyzed following isolation. DNA can be extracted from cancerous cells or tissues and used for analysis.

It is another feature of the invention that the substantial majority of the nucleic acids isolated from the mixed sample and detected in the assay system provide information relevant to the presence, quantity and/or polymorphic nature of a particular locus in the mixed sample. This ensures that the majority of nucleic acids analyzed in the assay system of the invention are informative.

In some aspects, a set of multiple selected loci are interrogated for each genomic region, and the quantity of the set of selected regions present in the mixed sample are individually summed to determine the relative frequency of a genomic region in a mixed sample. This includes determination of the frequency of the locus for the combined maternal and fetal DNA present in the mixed sample. Preferably, the determination does not require a distinction between the DNA from separate sources, although in certain aspects this information may be obtained in addition to the information of relative frequencies in the sample as a whole.

In preferred aspects, selected nucleic acids corresponding to informative loci are detected and summed to determine the relative frequency of a genomic region in the mixed sample. Frequencies that are higher than expected for loci from a first genomic region when compared to the loci from a second locus in a mixed sample is indicative of a CNV of the first genomic region in the mixed sample.

Comparison of genomic regions can be a comparison of part or all of a chromosome. For example, the genomic region detected for CNV may be an entire chromosome in the fetus (e.g., chromosomes 18 and 21), where the likelihood of both being aneuploid is minimal. This can also be a comparison of chromosomes where one is putatively aneuploid (e.g., chromosome 21) and the other acts as a reference chromosome (e.g. an autosome such as chromosome 2). In yet other aspects, the comparison may utilize two or more chromosomes that are putatively aneuploid and one or more reference chromosomes.

In one aspect, the assay system of the invention analyzes multiple nucleic acids representing selected loci on chromosomes of interest, and the relative frequency of each selected locus from the sample is analyzed to determine a relative chromosome frequency for each particular chromosome of interest in the sample. The chromosomal frequency of two or more chromosomes or portions thereof is then compared to statistically determine whether a chromosomal abnormality exists.

In another aspect, the assay system of the invention analyzes multiple copies of a set of selected loci on chromosomes of interest, and the relative frequency of each of the selected loci from the sample is analyzed and independently quantified to determine a frquency for each selected locus in the sample. The sum of the loci in the sample is compared to statistically determine whether a CNV exists for one or more loci in a genomic region of one source in a mixed sample.

In another aspect, subsets of loci on each chromosome are analyzed to determine whether a chromosomal abnormality exists. The loci frequency can be summed for a particular chromosome, and the summations of the loci used to determine aneuploidy. This aspect of the invention sums the frequencies of the individual loci in each genomic region and then compares the sum of the loci on a genomic region of one chromosome against a genomic region of another chromosome to determine whether a chromosomal abnormality exists. The subsets of loci can be chosen randomly but with sufficient numbers of loci to yield a statistically significant result in determining whether a chromosomal abnormality exists. Multiple analyses of different subsets of loci can be performed within a mixed sample to yield more statistical power. In another aspect, particular loci can be selected that are known to have less variation between samples, or by limiting the data used for determination of chromosomal frequency, e.g., by ignoring the data from loci with very high or very low frequency within a sample.

In a particular aspect, the measured quantities of one or more particular loci are normalized to account for differences in loci quantity in the sample. This can be done by normalizing for known variation from sources such as the assay system (e.g., temperature, reagent lot differences), underlying biology of the sample (e.g., nucleic acid content), operator differences, or any other variables.

In certain specific aspects, determining the relative percentage of nucleic acids from the minor source in a mixed sample may be beneficial in performing the assay system, as it will provide important information on the relative statistical presence of loci that may be indicative of copy number variation within the minor source in that sample. Determining the loci contributed to the mixed sample from the minor source can provide information used to calculate the statistically significant differences in frequencies for genomic regions of interest. Such loci could thus provide two forms of information in the assay—allelic information can be used for determining the percent minor cell contribution in a mixed sample and a summation of the allelic information can be used to determine the relative overall frequency of that locus in a mixed sample. The allelic information is not needed to determine the relative overall frequency of that locus.

In another specific aspect, the assay system of the invention can be utilized to determine potential mosaicism in a cell population, and whether further confirmatory tests should be undertaken to confirm the identification of mosaicism in the major and/or minor source. In certain instances, determination of the percent nucleic acids from the minor source in a mixed sample could assist in quantification of the estimated level of mosaicism. Mosaicism could be subsequently confirmed using other testing methods that could distinguish mosaic full or partial aneuploidy in specific cells or tissue.

In yet another specific aspect, the assay system of the invention can be utilized to determine contamination in a sample, with the minor species representing a contaminant species.

In another aspect, the oligonucleotides for a given selected nucleic acid can be connected at the non-sequence specific ends such that a circular or unimolecular probe may bind thereto. In this aspect, the 3' end and the 5' end of the circular probe binds to the selected locus and at least one universal amplification region is present in the non-selected specific sequence of the circular probe.

It is an important feature of the assay that the amplification products may be analyzed directly without the need for enrichment of polymorphic regions from the initial mixed sample. Thus, the current invention allows detection of both CNV and polymorphisms from a maternal sample without an intervening polymorphic enrichment step prior to sequence determination of the selected loci.

It is another important feature of the assay that both CNV and source contribution are determined using a targeted approach of selected amplification and detection. This allows the majority of information gathered in the assay to be useful for the determination of the CNV and/or source contribution, and obviates the need to generate sequence reads that must be aligned with a reference sequence.

These and other aspects, features and advantages will be provided in more detail as described herein.

BRIEF DESCRIPTION OF THE FIGURES

FIG. 8 is a summary of patient and sample information and data for a subset of a second cohort of pregnant subjects.

DEFINITIONS

Figure 1:
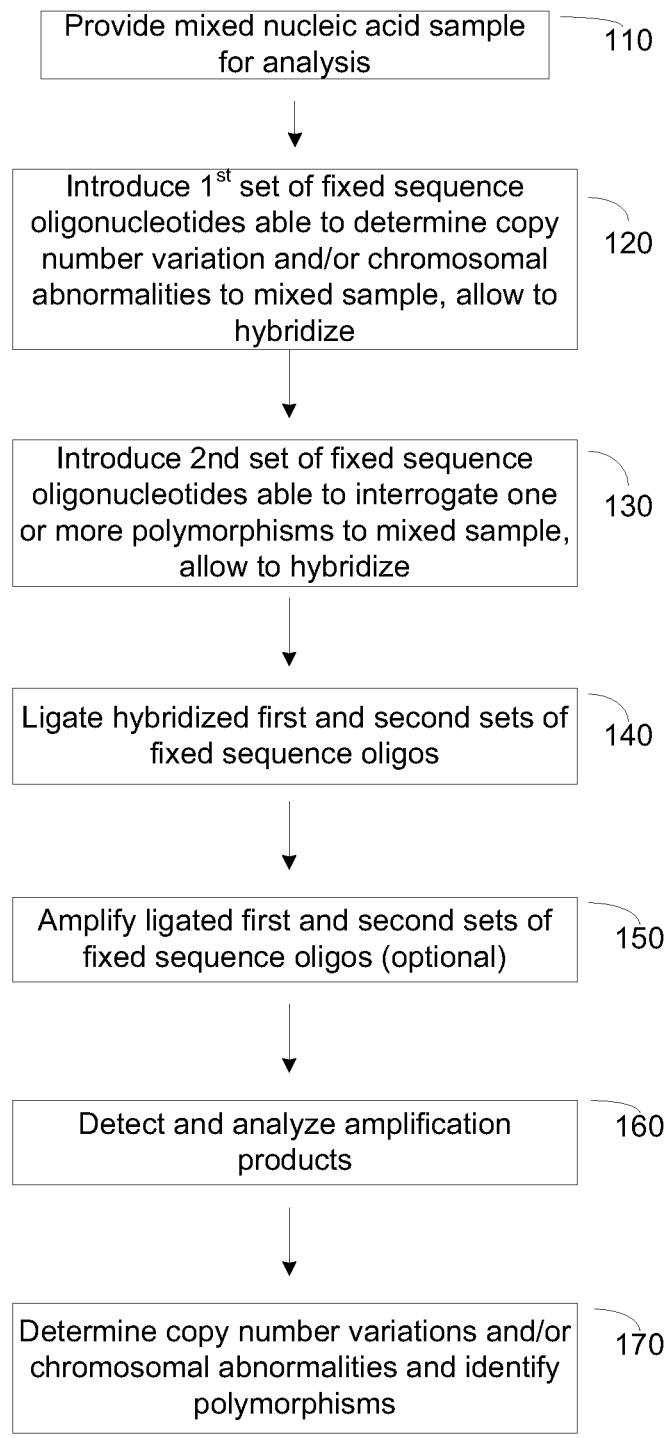
FIG. 1 is a simplified flow chart of the general steps utilized in the assay systems of the invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication method performed in vitro as compared to its starting amount in a mixed sample.

The term "amplification product" as used herein refers to the product resulting from an amplification reaction using the contiguous ligation product as a template, or the product resulting from an amplification reaction using a molecule complementary to the contiguous ligation product as a template.

The term "chromosomal abnormality" refers to any genetic variation that affects all or part of a chromosome larger than a single locus. The genetic variants may include but not be limited to any CNV such as amplifications or deletions, translocations, inversions, and mutations. Examples of chromosomal abnormalities include, but are not limited to, Down Syndrome (Trisomy 21), Edwards Syndrome (Trisomy 18), Patau Syndrome (Trisomy 13), Klinefelter's Syndrome (XXY), Triple X syndrome, XYY syndrome, Trisomy 8, Trisomy 16, Turner Syndrome, Robertsonian translocation, DiGeorge Syndrome and Wolf-Hirschhorn Syndrome.

The terms "complementary" or "complementarity" are used in reference to nucleic acid molecules (i.e., a sequence of nucleotides) that are related by base-pairing rules. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Stringent hybridization conditions will typically include salt concentrations of less than about 1 M, more usually less than about 500 mM and preferably less than about 200 mM. Hybridization temperatures are generally at least about 2° C. to about 6° C. lower than melting temperatures ($T_m$).

The term "copy number variation" or "CNV" as used interchangeably herein are alterations of the DNA of a genome that results in a cell having an abnormal number of copies of one or more loci in the DNA. CNVs that are clinically relevant can be limited to a single gene or include a contiguous set of genes. A CNV can also correspond to relatively large regions of the genome that have been deleted, inverted or duplicated on certain chromosomes, up to an including one or more additional copies of a complete chromosome. The term CNV as used herein does not refer to any sequence-related information, but rather to quantity or "counts" of genetic regions present in a sample.

The term "correction index" refers to an index that may contain additional nucleotides that allow for identification and correction of amplification, sequencing or other experimental errors including the detection of deletion, substitution, or insertion of one or more bases during sequencing as well as nucleotide changes that may occur outside of sequencing such as oligo synthesis, amplification, and any other aspect of the assay. These correction indices may be stand-alone indices that are separate sequences, or they may be embedded within other regions to assist in confirming accuracy of the experimental techniques used, e.g., a correction index may be a subset of sequences used for universal amplification or a subset of nucleotides of a sample locus.

The term "diagnostic tool" as used herein refers to any composition or assay of the invention used in combination as, for example, in a system in order to carry out a diagnostic test or assay on a patient sample.

The term "disease trait" refers to a monogenic or polygenic trait associated with a pathological condition, e.g., a disease, disorder, syndrome or predisposition.

The term "genomic region" as used herein refers to any region of one or more loci that are normally found in a contiguous fashion in a genome. A genomic region may vary in size up to and including an entire chromosome.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "informative locus" as used herein refers to a locus that is homozygous for one cell source and heterozygous for a second cell source on a particular chromosome or portion of a chromosome interrogated for purposes of determining a CNV of all or part of that chromosome. Informative loci for use in the assay system of the invention include loci used for interrogation of a reference chromosome as well as loci used for interrogation of a chromosome that is putatively aneuploid in a cell source. Informative loci can also distinguish copy number of loci in cell sources from different individuals within a single individual (e.g., detection of transplant donor cells in a transplant recipient or detection of a fetal DNA within a maternal mixed sample).

The terms "locus" and "loci" as used herein refer to a locus of known location in a genome.

The term "major source" refers to a source of nucleic acids in a sample from an individual that is representative of the predominant genomic material in that individual.

The term "maternal sample" as used herein refers to any sample taken from a pregnant mammal which comprises both fetal and maternal cell free genomic material (e.g., DNA). Preferably, maternal samples for use in the invention are obtained through relatively non-invasive means, e.g., phlebotomy or other standard techniques for extracting peripheral samples from a subject.

The term "melting temperature" or $T_m$ is commonly defined as the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 16.6(\log 10[Na+]) 0.41(\%[G+C]) - 675/n - 1.0$ m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual*, 3rd Ed., Cold Spring Harbor Laboratory Press (2001)). Other references include more sophisticated computations, which take structural as well as sequence characteristics into account for the calculation of $T_m$.

"Microarray" or "array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., sequence analysis, of one or more biological molecules using a microarray.

The term "minor source" refers to a source of nucleic acids within an individual that is present in limited amounts and which is distinguishable from the major source due to differences in its genomic makeup and/or expression. Examples of minor sources include, but are not limited to, fetal cells in a pregnant female, cancerous cells in a patient with a malignancy, cells from a donor organ in a transplant patient, nucleic acids from an infectious organism in an infected host, and the like.

The term "mixed sample" as used herein refers to any sample comprising cell free genomic material (e.g., DNA) from two or more cell types of interest, one being a major source and the other being a minor source within a single individual. Exemplary mixed samples include a maternal sample (e.g., maternal blood, serum or plasma comprising both maternal and fetal DNA), and a peripherally-derived somatic sample (e.g., blood, serum or plasma comprising different cell types, e.g., hematopoietic cells, mesenchymal cells, and circulating cells from other organ systems). Mixed samples include samples with genomic material from both a major and a minor source in an individual, which may be e.g., normal and atypical somatic cells, or cells that comprise genomes from two different individuals, e.g., a sample with both maternal and fetal genomic material or a sample from a transplant patient that comprises cells from both the donor and recipient.

The term "monogenic trait" as used herein refers to any trait, normal or pathological, that is associated with a mutation or polymorphism in a single gene. Such traits include traits associated with a disease, disorder, or predisposition caused by a dysfunction in a single gene. Traits also include non-pathological characteristics (e.g., presence or absence of cell surface molecules on a specific cell type).

The term "non-maternal" allele means an allele with a polymorphism and/or mutation that is found in a fetal allele (e.g., an allele with a de novo SNP or mutation) and/or a paternal allele, but which is not found in the maternal allele.

By "non-polymorphic", when used with respect to detection of selected loci, is meant a detection of such locus, which may contain one or more polymorphisms, but in which the detection is not reliant on detection of the specific polymorphism within the region. Thus a selected locus may contain a polymorphism, but detection of the region using the assay system of the invention is based on occurrence of the region rather than the presence or absence of a particular polymorphism in that region.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

According to the present invention, a "nucleotide" may be unlabeled or detectably labeled by well known techniques. Fluorescent labels and their attachment to oligonucleotides are described in many reviews, including Haugland, *Handbook of Fluorescent Probes and Research Chemicals*, 9th Ed., Molecular Probes, Inc., Eugene Oreg. (2002); Keller and Manak, *DNA Probes*, 2nd Ed., Stockton Press, New York (1993); Eckstein, Ed., *Oligonucleotides and Analogues: A Practical Approach*, IRL Press, Oxford (1991); Wetmur, *Critical Reviews in Biochemistry and Molecular Biology*, 26:227-259 (1991); and the like. Other methodologies applicable to the invention are disclosed in the following sample of references: Fung et al., U.S. Pat. No. 4,757,141; Hobbs, Jr., et al., U.S. Pat. No. 5,151,507; Cruickshank, U.S. Pat. No. 5,091,519; Menchen et al., U.S. Pat. No. 5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580: Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluroescently labeled nucleotides include [R6G]dUTP, [TAMRA]dUTP, [R110]dCTP, [R6G]dCTP, [TAMRA] dCTP, [JOE]ddATP, [R6G]ddATP, [FAM]ddCTP, [R110] ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosomee Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg.

The terms "oligonucleotides" or "oligos" as used herein refer to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more. Suitable nucleic acid molecules may be prepared by the phosphoramidite method described by Beaucage and Carruthers (Tetrahedron Lett., 22:1859-1862 (1981)), or by the triester method according to Matteucci, et al. (J. Am. Chem. Soc., 103:3185 (1981)), both incorporated herein by reference, or by other chemical methods such as using a commercial automated oligonucleotide synthesizer.

The term "polygenic trait" as used herein refers to any trait, normal or pathological, that is associated with a mutation or polymorphism in more than a single gene. Such traits include traits associated with a disease, disorder, syndrome or predisposition caused by a dysfunction in two or more genes. Traits also include non-pathological characteristics associated with the interaction of two or more genes.

As used herein the term "polymerase" refers to an enzyme that links individual nucleotides together into a long strand, using another strand as a template. There are two general types of polymerase—DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes or sequence variants in a locus, including but not limited to single nucleotide polymorphisms (SNPs), methylation differences, short tandem repeats (STRs), single gene polymorphisms, point mutations, trinucleotide repeats, indels and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a locus to a capture oligonucleotide for detection of a specific locus.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "sample index" refers generally to a series of unique nucleotides (i.e., each sample index is unique to a sample in a multiplexed assay system for analysis of multiple samples). The sample index can thus be used to assist in locus identification for multiplexing of different samples in a single reaction vessel, such that each sample can be identified based on its sample index. In a preferred aspect, there is a unique sample index for each sample in a set of samples, and the samples are pooled during sequencing. For example, if twelve samples are pooled into a single sequencing reaction, there are at least twelve unique sample indexes such that each sample is labeled uniquely.

The term "selected locus" as used herein refers to a locus corresponding to a loci interrogated, e.g., for copy number, the presence or absence of one or more polymorphism, presence or absence of an infectious organism, etc. Such selected loci may be directly isolated and amplified from the sample for detection, e.g., based on hybridization and/or other sequence-based techniques, or they may be amplified using the sample as a template prior to detection of the sequence. Nucleic acids regions for use in the assay systems of the present invention may be selected on the basis of DNA level variation between individuals, based upon specificity for a particular chromosome, based on CG content and/or required amplification conditions of the selected loci, or other characteristics that will be apparent to one skilled in the art upon reading the present disclosure.

The terms "sequencing", "sequence determination" and the like as used herein refers generally to any and all biochemical methods that may be used to determine the order of nucleotide bases in a nucleic acid.

The term "source contribution" as used herein refers to the relative contribution of two or more sources of nucleic acids within an individual. The contribution from a single is generally determined as a percent of the nucleic acioods from a sample, although any relative measurement can be used.

The term "specifically binds", "specific binding" and the like as used herein, when referring to a binding partner (e.g., a nucleic acid probe or primer, antibody, etc.) that results in the generation of a statistically significant positive signal under the designated assay conditions. Typically the interaction will subsequently result in a detectable signal that is at least twice the standard deviation of any signal generated as a result of undesired interactions (background).

The term "status" as used herein in relationship to a gene refers to the sequence status of the alleles of a particular gene, including the coding regions and the non-coding regions that affect the translation and/or protein expression from that gene. The status of a gene associated with an autosomal dominant disease such as achondroplasia (e.g., the gene encoding the fibroblast growth factor receptor) or Huntington's disease (e.g., the Huntingtin gene), or for an X-linked disease in the case of a male fetus, can be classified as affected i.e., one allele possesses mutation(s) that is causative of the diseases or disorder, or non-affected, i.e. both alleles lack such mutations(s). The status of a gene associated with an autosomal recessive disease or a maternal gene associated with an X-linked recessive disorder, may be classified as affected, i.e., both alleles possess mutation(s) causative of the diseases or disorder; carrier, i.e. one allele possesses mutation(s) causative of the diseases or disorder; or non-affected, i.e. both alleles lack such mutations(s). The status of a gene may also indicate the presence or absence of a particular allele associated with a risk of developing a polygenic disease, e.g., a polymorphism that is protective against a particular disease or disorder or a polymorphism associated with an enhanced risk for a particular disease or disorder.

DETAILED DESCRIPTION OF THE INVENTION

The assay systems and methods described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W. H. Freeman, New York (1995); Gait, "*Oligonucleotide Synthesis: A Practical Approach*" IRL Press, London (1984); Nelson and Cox, *Lehninger, Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "an," and "the" include plural referents unless the context clearly dictates otherwise. Thus, for example, reference to "a locus" refers to one, more than one, or mixtures of such regions, and reference to "an assay" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The present invention provides single assay systems with the ability to detect copy number variations, polymorphisms and nucleic acids associated with disease states (for example, nucleic acids from pathogens, or associated with cancer, diabetes, Alzheimers Disease, and the like) in a mixed sample from a single individual. The assay allows the identification of genetic variation in one or more minor sources in a mixed sample using information about the copy number of selected loci in the sample and information about the percentage contribution of nucleic acids from the major and the one or more minor sources in the sample. These methods are useful for any mixed sample containing genomic material (e.g., DNA) from a major and a minor source that are present in a single individual.

The use of selected loci in the assay methods of the invention provides direct detection of loci for determination of copy number variation in one or more sources within the mixed sample. A distinct advantage of the invention is that the selected loci corresponding to copy number variation and/or polymorphisms can be further analyzed using a variety of detection and quantification techniques, including but not limited to hybridization techniques, digital PCR and high throughput sequencing determination techniques. Probes can be designed against any number of selected loci for any chromosome. Although amplification prior to the identification and quantification of the selected loci is not mandatory, limited amplification of the mixed sample prior to detection may be used to expand the overall number of nucleic acids within the starting materials.

FIG. 1 is a simplified flow chart of the general steps utilized in the assay systems of the invention. FIG. 1 shows method 100, where in a first step 110, a mixed nucleic acid sample is provided for analysis. The mixed sample can be prepared from virtually any sample as such techniques are known to those of skill in the art (see, e.g., Tietz Textbood of Clinical Chemistry and Molecular Diagnostics, 4th Ed., Chapter 2, Burtis, C. Ashwood E. and Bruns, D, eds. (2006); Chemical Weapons Convention Chemicals Analysis: Sample Collection, Preparation and Analytical Methods, Mesilaakso, M., ed., (2005); Pawliszyn, J., Sampling and Sample Preparation for Field and Laboratory, (2002); Venkatesh Iyengar, G., et al., Element Analysis of Biological Samples: Priniciples and Practices (1998); Drielak, S., Hot Zone Forensics: Chemical, Biological, and Radiological Evidence Collection (2004); Wells, D., High Throughput Bioanalytical Sample Preparation (Progress in Pharmaceutical and Biomedical Analysis) (2002)), each of which is incorporated by reference). Depending on the type of mixed sample chosen, additional processing and/or purification steps may be performed to obtain nucleic acid fragments of a desired purity or size, using processing methods including but not limited to sonication, nebulization, gel purification, PCR purification systems, nuclease cleavage, or a combination of these methods. In a preferred aspect, samples comprising cell-free DNA (cfDNA) are used.

At step 120, a first set of fixed sequence oligonucleotides are introduced to the mixed nucleic acid sample, under conditions that allow the first set of fixed sequence oligonucleotides to hybridize to the mixed nucleic acid sample. The first set of fixed sequence oligonucleotides comprise nucleic acid sequences that are complementary to one or more selected loci in the mixed sample, which as will be described in detail herein are useful in determining copy number variations and/or chromosomal abnormalities. The nucleic acid sequences capable of determining copy number variations and/or chromosomal abnormalities include sequences that allow for identification of chromosomal abnormalities such as amplifications or deletions, aneuploidies, translocations, or inversions.

At step 130, a second set of fixed sequence oligonucleotides are introduced to the mixed nucleic acid sample and first set of fixed sequence oligonucleotides under conditions that allow the second set of fixed sequence oligonucleotides to hybridize to the mixed nucleic acid sample. The second set of fixed sequence oligonucleotides comprise nucleic acid sequences that are complementary to one or more selected loci in the mixed sample, able to detect polymorphisms. Washing steps optionally may be included between steps 120 and 130, and 130 and 140.

At step 140, the first and second sets of fixed sequence oligonucleotides that have hybridized to adjacent regions of the selected loci in the mixed sample are ligated, and at step 150, the ligated oligonucleotides are amplified. The ligated and amplified oligonucleotides are then detected and analyzed, which allows for determination of copy number variations or chromosomal abnormalities and identification of polymorphisms at step 160.

The sets of fixed sequence nucleic acids are designed to hybridize to at least two separate regions in a selected locus. In preferred aspects, two or more separate oligos are used to hybridize to these regions to provide adjacent nucleic acids complementary to the selected locus. In some aspects, however, a single probe can be used which comprises two or more distinct non-adjacent regions that are complementary to the selected loci including precircular probes such as so-called "padlock probes" or "molecular inversion probes (MIPs)".

The present invention provides an improved system over more random techniques such as massively parallel sequencing, shotgun sequencing, and the use of random digital PCR which have been used by others to detect CNVs. These aforementioned approaches rely upon sequencing of all or a statistically significant population of DNA fragments in a sample, followed by mapping of these fragments or otherwise associating the fragments to their appropriate chromosomes. The identified fragments are then compared against each other or against some other reference (e.g., normal chromosomal makeup) to determine CNVs on particular chromosomes. These methods are inherently inefficient as compared to the present invention, as the primary chromosomes of interest only constitute a minority of data that is generated from the detection of such DNA fragments in the mixed samples.

The assays of the present invention provide targeted detection of selected loci, which provides information on both the content of the selected locus (i.e., presence of a polymorphic region) and information on the frequency of the selected locus in a sample (with or without detecting any putative polymorphisms in that region). This key feature provides the ability to detect both copy number of selected loci and the presence or absence of polymorphisms in selected loci as a single data set from performance of a multiplexed assay of the invention.

Techniques that are dependent upon a very broad sampling of DNA in a sample are providing a very broad coverage of the DNA analyzed, but in fact are sampling the DNA contained within a sample on a 1× or less basis (i.e., subsampling). In contrast, the amplification of selected loci used in the present assays provides depth of coverage of particular loci of interest, and provides a "super-sampling" of such selected loci with an average sequence coverage of preferably 2× or more, more preferably sequence coverage of 100× of more, even more preferably sequence coverage of 1000× or more of the selected loci (including from the one or more minor sources) present in the initial mixed sample.

A distinct advantage of the invention is that the amplification products resulting from the assays can be analyzed using a variety of detection and quantification techniques, including but not limited to hybridization techniques, digital PCR and high throughput sequencing determination techniques.

The methods of the invention provide a more efficient and economical use of data, and the substantial majority of sequences analyzed following sample amplification result in affirmative information about the sequence identity and frequency of selected loci in the mixed sample. Thus, unlike techniques relying on massively parallel sequencing or random digital "counting" of chromosome regions and subsequent identification of relevant data from such counts, the assay system of the invention provides a much more efficient use of data collection than the random approaches taught by others in the art.

Assay Methods

The assay systems of the invention utilize a general scheme as described above, though many different configurations and variations can be employed, a few of which are described below and more of which are exemplified in U.S. Ser. No. 61/371,605 filed Aug. 6, 2010, incorporated by reference herein in its entirety.

Figure 2:
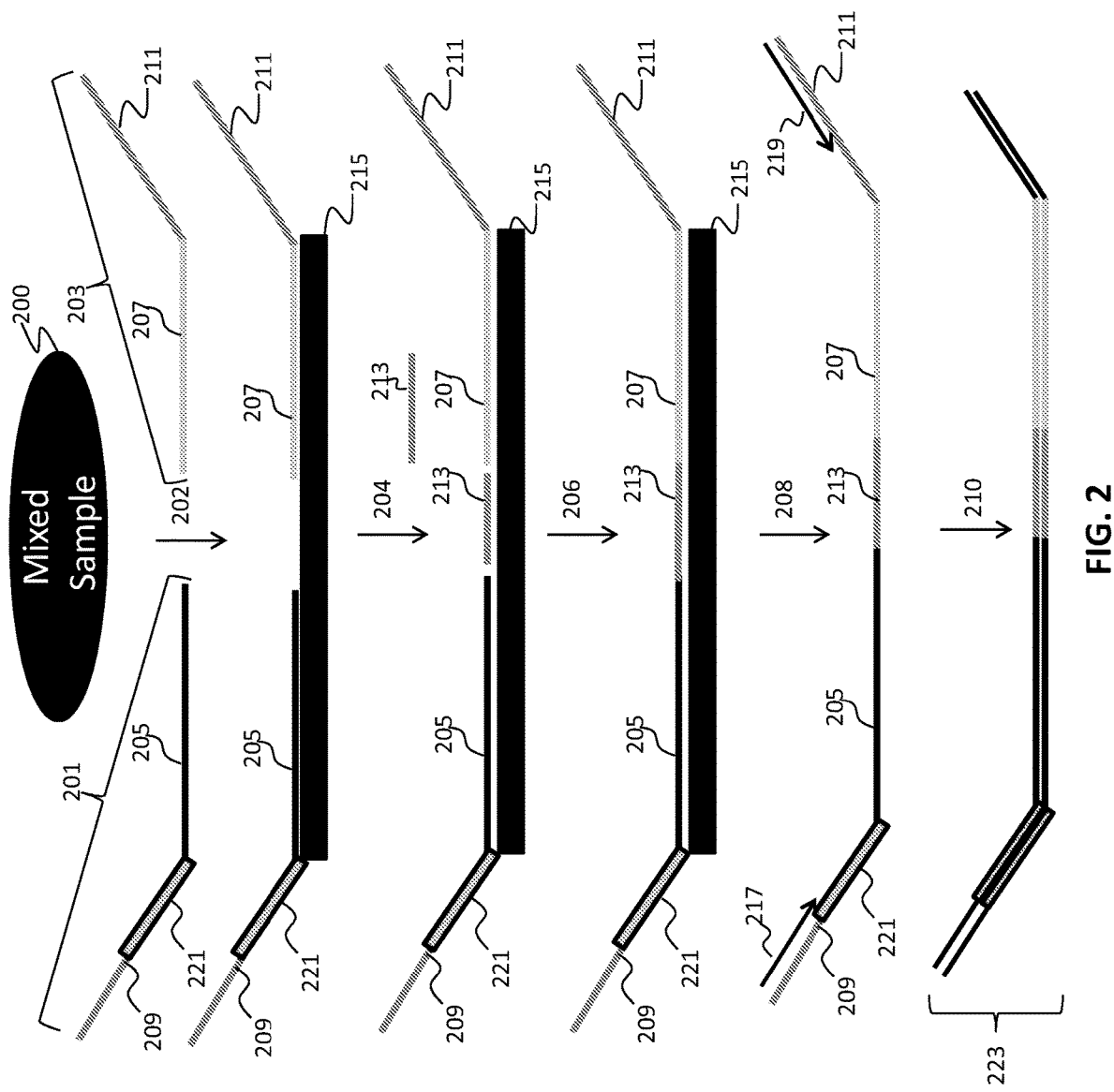
FIG. 2 illustrates a first general schematic for a ligation-based assay system of the invention.

FIG. 2 illustrates a first general schematic for a ligation-based assay system of the invention. The fixed sequence oligonucleotides 201, 203 comprise universal primer regions 209 and 211, respectively, and regions complementary to the selected locus 205 and 207, respectively. However, in addition, the assay system in FIG. 2 employs a sample index region 221 on the first fixed sequence oligonucleotide 201. In certain aspects, all or a portion of the sequences of the selected loci are directly detected using the described techniques, e.g., by sequence determination or hybridization techniques. In the example of FIG. 2, a sample index is associated with the first fixed sequence oligonucleotide 201. The detection of the indices can identify a sequence from a specific sample in a highly multiplexed assay system.

At step 202, the fixed sequence oligonucleotides 201, 203 are introduced in step 202 to the mixed sample 200 and allowed to specifically bind to the selected locus 215. Following hybridization, the unhybridized fixed sequence oligonucleotides are preferably separated from the remainder of the genetic sample (by, e.g., washing—not shown). A bridging oligo is then introduced and allowed to hybridize in step 204 to the region of the locus 215 between the first 201 and second 203 fixed sequence oligonucleotides. The bound oligonucleotides are ligated at step 206 to create a contiguous nucleic acid spanning and complementary to the locus of interest. In certain aspects of the invention, the bridging oligonucleotides of are between 2-45 nucleotides in length. In a specific aspect, the bridging oligonucleotides are between 3-9 nucleotides in length. In yet another specific aspect, the oligonucleotides are between 10-30 nucleotides in length.

Following ligation, the ligation product is eluted from the gDNA template. Universal primers 217, 219 are introduced in step 208 to amplify the ligated first and second fixed sequence oligonucleotides to create 210 amplification products 223 that comprise the sequence of the locus of interest. These products 223 are isolated, detected, identified and quantified to provide information regarding the presence and amount of the selected loci in the mixed sample. Preferably, the amplification products are detected and quantified through sequence determination. In specific aspects, it is desirable to determine the sequences of both the sample index and the amplification products, for example, to provide identification of the sample as well as the locus. The indices such as the sample index shown here envisioned in the invention may be associated with the first fixed sequence oligonucleotides, the second fixed sequence oligonucleotides or both. Alternatively or in addition, indices may be associated with primers that are used to amplify the ligated first and second fixed sequence oligonucleotides, which also serves to incorporate indices into the amplification products.

In preferred aspects and as shown in FIG. 2, indices representative of the mixed sample from which a nucleic acid may be isolated are used to identify the source of the selected loci in a multiplexed assay system. In such aspects, the nucleic acids are uniquely identified with the sample index. Uniquely identified oligonucleotides may then be combined into a single reaction vessel with nucleic acids from other mixed samples prior to sequencing. In such a case, the sequencing data is segregated by the unique sample index to determine the frequency of each target locus for each mixed sample and to determine whether there is a chromosomal abnormality in an individual sample.

In aspects of the invention using sample indices, the fixed sequence oligonucleotides preferably are designed so that sample indices comprising identifying information are located between the universal primer regions 209 and 211 and the regions complementary to the selected loci in the sample 205 and 207. Alternatively, the indices and universal amplification sequences can be added to the ligated first and second fixed sequence oligos (and the bridging oligo, if present) by including these indices in the primers used to amplify the ligation products for separate samples. In either case, preferably the indices are encoded upstream of the locus-specific sequences but downstream of the universal primers so that they are preserved upon amplification.

Figure 3:
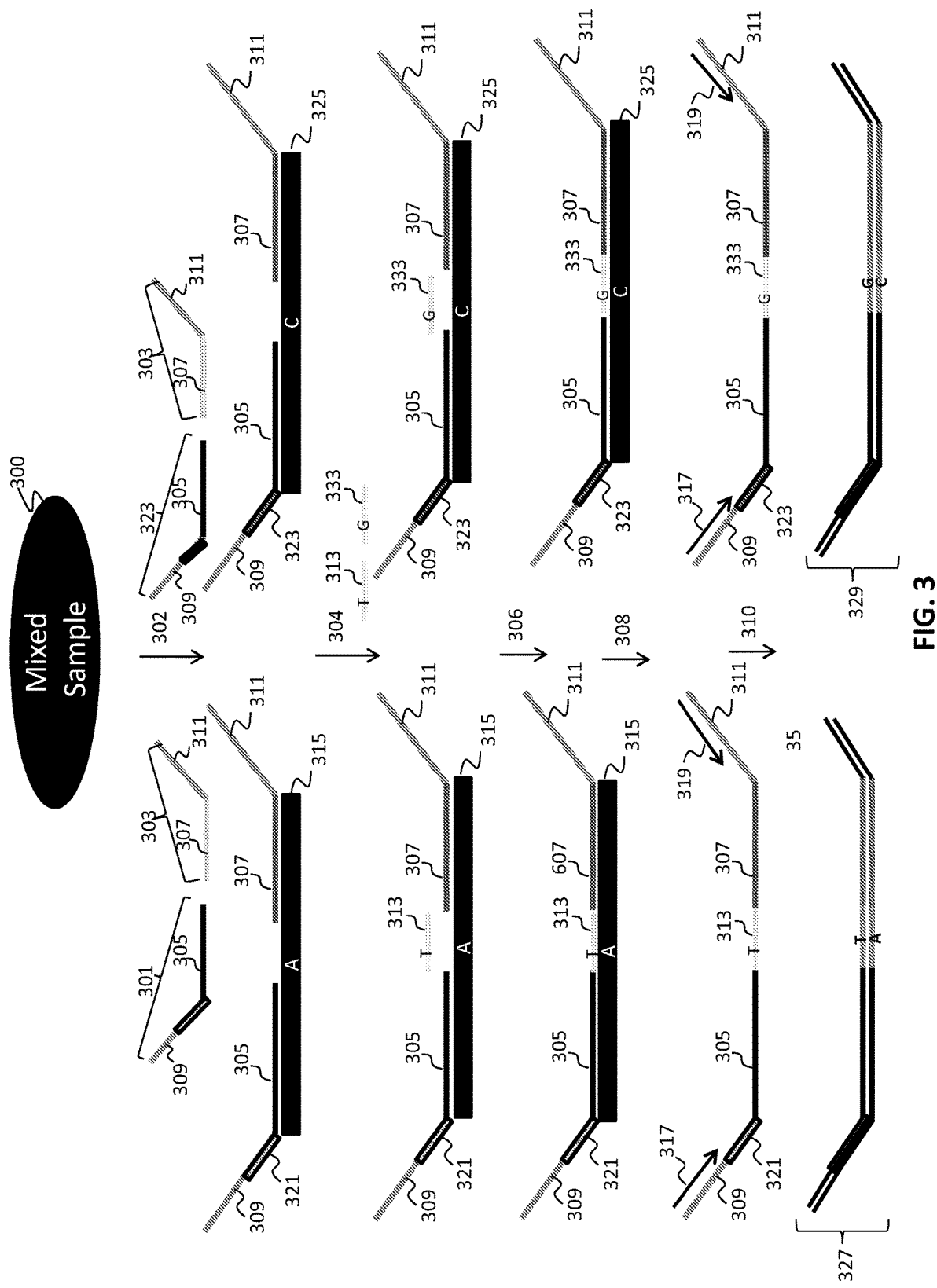
FIG. 3 illustrates a second general schematic for a ligation-based assay system of the invention.

FIG. 3 exemplifies methods of the assay system in which one or more bridging olignucleotides are employed and exemplifies how polymorphisms may be detected and identified. In FIG. 3, two fixed sets of sequence oligonucleotides are used which comprise substantially the same universal primers 309, 311 and sequence-specific regions 305, 307, but comprise different sample indices, 321, 323 on the fixed sequence oligonucleotides of the set where the different indices correspond to different base sequences for the single nucleotide polymorphism present in a particular sample. The ligation reactions are carried out with material from the same mixed sample 300, but in separate tubes with the different allele-specific oligo sets. Bridging oligonucleotides corresponding to two possible nucleotides for this SNP in the selected loci 313, 333 are used to detect of the selected locus in each ligation reaction. Two allele indices 321, 323 that are indicative of the particular polymorphic alleles are incorporated into the amplification products so that sequence determination of the actual sequence of the ligated first, second and bridging oligonucleotides are not necessarily needed, although the sequences of the entire ligation products may still be determined to identify polymorphisms and/or provide confirmation.

Each of the fixed sequence oligonucleotides comprises a region complementary to the selected locus 305, 307, and universal primer regions 309, 311 used to amplify the different selected loci following initial selection and/or isolation of the selected loci from the mixed sample. The universal primer regions are located at the ends of the fixed sequence oligonucleotides 301, 303, and 323 flanking the indices and the regions complementary to the nucleic acid of interest, thus preserving the nucleic acid-specific sequences and the sample indices in the products of any universal amplification methods. The fixed sequence oligonucleotides 301, 303, 323 are introduced at step 302 to an aliquot of the genetic sample 300 and allowed to specifically bind to the selected loci 315 or 325. Following hybridization, the unhybridized fixed sequence oligonucleotides are preferably separated from the remainder of the genetic sample by, e.g., washing (not shown).

The bridging oligos corresponding to an A/T SNP 313 or a G/C SNP 333 are introduced and allowed to bind in step 304 to the region of the selected locus 315 or 325 between the first 305 and second 307 nucleic acid-complementary regions of the fixed sequence oligonucleotides. Alternatively, the bridging oligos 313, 333 can be introduced to the sample simultaneously with the fixed sequence oligonucleotides. The bound oligonucleotides are ligated in step 306 in the single reaction mixture to create a contiguous nucleic acid spanning and complementary to the selected locus.

Following ligation, the separate reactions may preferably be combined for the universal amplification and detection steps. Universal primers 317, 319 are introduced to the combined reactions at step 308 to amplify the ligated template regions and create at step 310 ligated first and second fixed sequence oligos and bridging oligo products 327, 329 that comprise the sequence of the selected locus representing both SNPs in the selected locus. These ligation products 327, 329 are detected and quantified through sequence determination of the ligation product, through the sample index and/or the region of the product containing the SNP in the selected locus.

Figure 4:
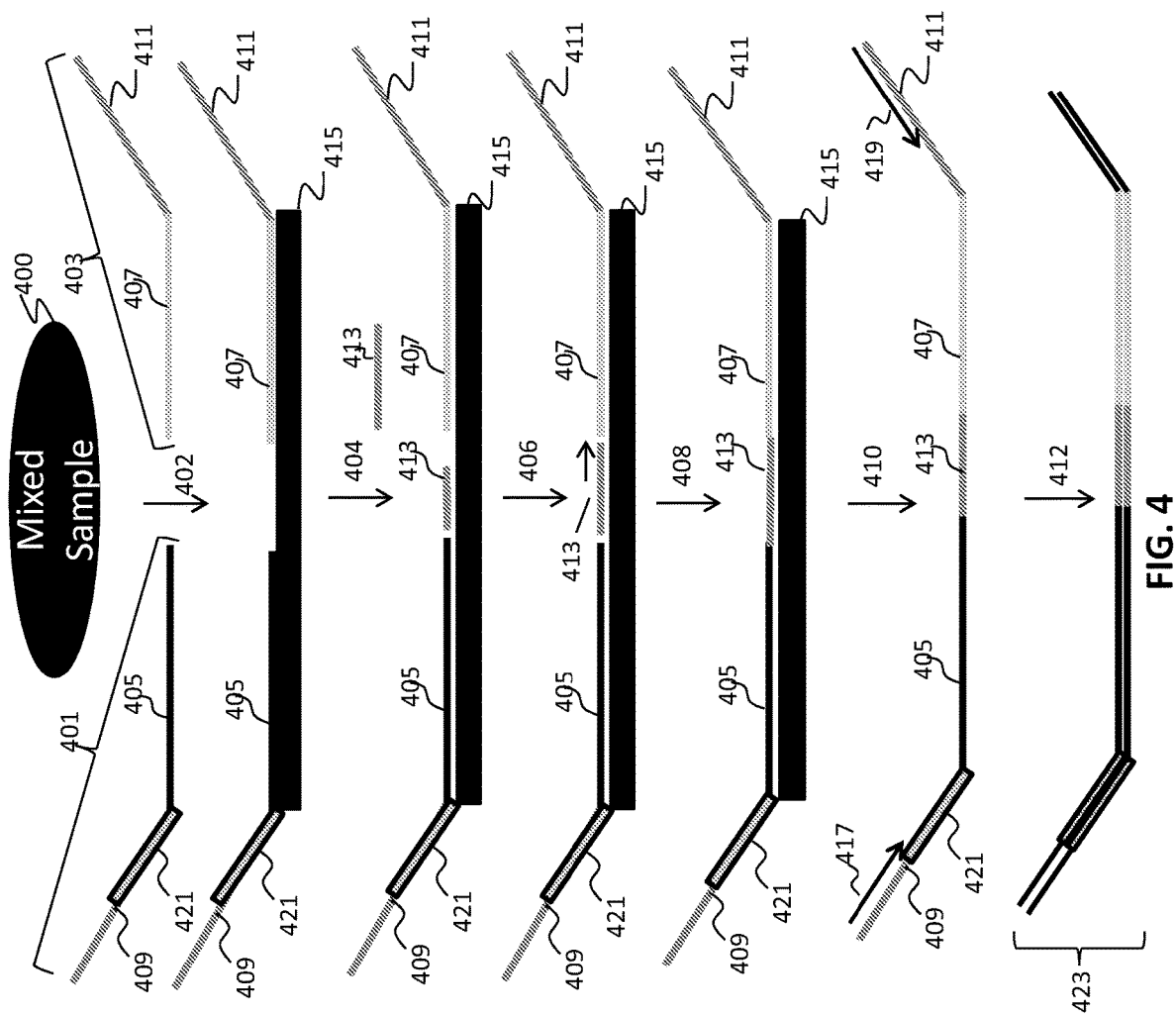
FIG. 4 is a third general schematic for a ligation-based assay system of the invention.

In an alternative configuration of the methods of the assay systems of the invention, the bridging oligo may hybridize to a region that is not directly adjacent to the region complementary to one or both of the fixed sequence oligos, and an intermediate step requiring extension of one or more of the oligos is necessary prior to ligation. For example, as illustrated in FIG. 4, each set of oligonucleotides preferably contains two oligonucleotides 401, 403 of fixed sequence and one or more bridging oligonucleotides 413. Each of the fixed sequence oligonucleotides comprises a region complementary to the selected locus 405, 407, and primer sequences, preferably universal primer sequences, 409, 411, i.e., oligo regions complementary to universal primers. The primer sequences 409, 411 are located at or near the ends of the fixed sequence oligonucleotides 401, 403, and thus preserve the nucleic acid-specific sequences in the products of any universal amplification methods. The fixed sequence oligonucleotides 401, 403 are introduced at step 402 to the mixed sample 400 and allowed to specifically bind to the complementary portions of the locus of interest 415. Following hybridization, the unhybridized fixed sequence oligonucleotides are preferably separated from the remainder of the genetic sample (not shown).

The bridging oligonucleotide is then introduced at step 404 and allowed to bind to the region of the selected locus 415 between the first 401 and second 403 fixed sequence oligonucleotides. Alternatively, the bridging oligo can be introduced simultaneously with the fixed sequence oligonucleotides. In this exemplary aspect, the bridging oligo hybridizes to a region directly adjacent to the first fixed sequence oligo region 405, but is separated by one or more nucleotides from the complementary region of the second fixed sequence oligonucleotide 407. Following hybridization of the fixed sequence and bridging oligos, the bridging oligo 413 is extended at step 406, e.g., using a polymerase and dNTPs, to fill the gap between the bridging oligo 413 and the second fixed sequence oligo 403. Following extension, the bound oligonucleotides are ligated at step 408 to create a contiguous nucleic acid spanning and complementary to the locus of interest 415. After ligation, universal primers 417, 419 are introduced at step 410 to amplify the ligated first, second and bridging oligos to create at step 412 amplification products 423 that comprise the sequence of the selected locus of interest. Amplification products 423 are optionally isolated, detected, and quantified to provide information on the presence and amount of the selected locus(s) in the mixed sample.

Detecting Copy Number Variations

The present invention provides methods for identifying copy number variation at one or more loci and the presence or absence of one or more polymorphisms. This can be performed using amplification methods for identification of loci corresponding to specific chromosomes of interest loci corresponding to single gene sequences.

The assay systems utilize nucleic acid probes designed to identify, and preferably to isolate, selected loci in a mixed sample. Certain of the probes identify sequences of interest in selected loci interrogated for copy number (i.e. loci frequency), and other probes identify sequences that correspond to polymorphisms of interest (i.e. loci content) in nucleic acids corresponding to a major source or minor source in a mixed sample.

In specific aspects, the assay systems of the invention employ one or more selective amplification steps (e.g., using one or more primers that specifically hybridize to a selected locus) for isolating, amplifying or analyzing substantially all of the selected loci analyzed. This is in direct contrast to the random amplification approach used by others employing, e.g., massively parallel sequencing, as such amplification techniques generally involve random amplification of all or a substantial portion of the genome. In addition, the initial sample can optionally be enriched using methods such as general amplification to increase the copy number of nucleic acids in the mixed sample. Preferably the hybridization, ligation, and amplification steps used to identify the loci of interest are performed directly on the mixed sample.

In a general aspect, the user of the invention analyzes multiple selected loci on different chromosomes. When multiple loci are analyzed for a sample, a preferred embodiment is to amplify all of the selected loci for each sample in one reaction vessel. The frequencies of the multiple selected loci are used to determine whether a chromosomal abnormality exists, and optionally to identify polymorphisms in the selected loci.

In preferred aspects, multiple selected loci from two or more samples may be amplified in a single reaction vessel, and the information simultaneously analyzed in a single data set, e.g., through sequence determination. The resulting data is then analyzed to separate the results for the different sample and used to determine the presence of absence of CNV and the source contribution in individual samples.

In one aspect, chromosomal abnormalities are identified in the assay system of the invention using multiple selected loci on multiple chromosomes, and the frequency of the selected loci on the multiple chromosomes compared to identify an increase likelihood of aneuploidy based on the ratios frequencies of the multiple loci on the chromosomes. Normalization or standardization of the frequencies can be performed for one or more selected loci.

In another aspect, the assay system sums the frequencies of the selected loci on two or more chromosomes and then compares the sum of the selected loci on one chromosome against another chromosome to determine whether a chromosomal aneuploidy exists. In another aspect, the assay system analyzes subsets of selected loci frequencies on two or more chromosomes to determine whether a chromosomal aneuploidy exists for one of the two chromosomes. The comparison can be made either within the same or different chromosomes.

In certain aspects, the data used to determine the frequency of the selected loci may exclude outlier data that appear to be due to experimental error, or that have elevated or depressed levels based on an idiopathic genetic bias within a particular sample. In one example, the data used for summation may exclude DNA regions with a particularly elevated frequency in one or more samples. In another example, the data used for summation may exclude selected loci that are found in a particularly low abundance in one or more samples.

In another aspect subsets of selected loci can be chosen to yield a statistically significant result when determining whether a chromosomal abnormality exists. Multiple analyses of different subsets of selected loci can be performed within a mixed sample to yield more statistical power. For example, if there are 100 selected loci for chromosome 21 and 100 selected loci for chromosome 18, a series of analyses could be performed that evaluate fewer than 100 regions for each of the chromosomes. In this example, selected loci are not being selectively excluded.

The quantity of different nucleic acids detectable on certain chromosomes may vary depending upon a number of factors, including general representation of loci in different cell sources in mixed samples, degradation rates of the different nucleic acids representing different loci in mixed samples, sample preparation methods, and the like. Thus, in another aspect, the quantity of particular loci on a chromosome is summed to determine the loci quantity for different chromosomes in the sample. The loci frequencies are summed for a particular chromosome, and the sum of the loci are used to determine aneuploidy. This aspect of the invention sums the frequencies of the individual loci on each chromosome and then compares the sum of the loci on one chromosome against one or more other chromosomes to determine whether a chromosomal abnormality exists.

The nucleic acids analyzed using the assay systems of the invention are preferably selectively amplified and optionally isolated from the mixed sample using primers specific to the locus of interest (e.g., to a locus of interest in a mixed sample). The primers for selective amplification may be chosen for various reasons, but are preferably designed to 1) efficiently amplify a region from the chromosome of interest; 2) have a predictable range of expression from maternal and/or fetal sources in different mixed samples; and 3) be distinctive to the particular chromosome, i.e., not amplify homologous regions on other chromosomes. The following are exemplary techniques that may be employed in the assay system or the invention.

The assay system of the invention detects both aneuploidies and specific chromosomal abnormalities through identification and quantification of specific loci of interest. Such chromosomal abnormalities include, but are not limited to, deletion mutations, insertion mutations, copy number polymorphisms, copy number variants, chromosome 22q11 deletion syndrome, 11q deletion syndrome on chromosome 11, 8p deletion syndrome on chromosome 8, and the like. Generally, at least two selected loci present on the same or separate chromosomes are analyzed, and at least one of the selected loci is associated with the fetal allelic abnormality. The sequences of the two selected loci and number of copies of the two selected loci are then compared to determine whether the chromosomal abnormality is present, and if so, the nature of the abnormality.

While much of the description contained herein describes detecting aneuploidy by counting the abundance of selected loci on one or more putative aneuploid chromosomes and the abundance of selected loci on one or more normal chromosomes, the same techniques may be used to detect copy number variations where such copy number variation occurs on only a portion of a chromosome. In detection of copy number variations, multiple selected loci within the putative copy number variation location are compared to multiple selected loci outside of the putative copy number variation location. For instance, one may detect a chromosome 22q11 deletion syndrome in a fetus in a maternal sample by selecting two or more loci within the 22q11 deletion and two or more loci outside of the 22q11 deletion. The loci outside of the 22q11 deletion may be on another region of Chromosome 22 or may be on a completely different chromosome. The abundance of each loci is determined by the methods described in this application.

In some aspects a universal amplification may be used for amplifying the selected loci. In some aspects, the selected loci for each sample are assayed in a single reaction in a single vessel. In other aspects, loci from multiple samples can be assayed in a single reaction in a single vessel.

Certain aspects of the invention can detect a deletion, including the boundaries of such deletions. In some aspects, at least 24 selected loci may be used within the region of the putative deletion and at least 24 selected loci may be used outside of the region of the putative deletion. In another aspect at least 48 selected loci may be used within the region of the putative deletion and at least 48 selected loci may be used outside of the region of the putative deletion. In another aspect at least 48 selected loci may be used within the region of the putative deletion and at least 96 selected loci may be used outside of the region of the putative deletion. In another aspect at least 48 selected loci may be used within the region of the putative deletion and at least 192 selected loci may be used outside of the region of the putative deletion. In a preferred aspect at least 384 selected loci may be used within the region of the putative deletion and at least 384 selected loci may be used outside of the region of the putative deletion. The selected loci within the region of the putative and the selected loci outside of the region of the putative deletion are summed. These sums are then compared to each other to determine the presence or absence of a deletion. Optionally, a ratio of the sums is computed and that ratio may be compared to an average ratio created from a normal population. When the ratio for one or more selected loci falls statistically outside of an expected ratio, a deletion is detected. The threshold for positively identifying a deletion may be twice or more, preferably four or more times the variation calculated in the normal population. When a plurality of selected loci are sued within and outside the region of the putative deletion, boundaries of the deletion may be identified.

Polymorphisms Associated with Diseases or Predispositions

The assay systems of the invention can also be utilized to detect polymorphisms, such as those associated with an autosomal dominant or recessive disease or mutation. Given the multiplexed nature of the assay systems of the invention, detection takes place in the same assay as the detection of chromosomal abnormalities. Thus a single assay system can provide diagnostic information on different classes of genetic mutations. Accordingly, as the preferred assay systems of the invention are highly multiplexed and able to interrogate hundreds or even thousands of selected loci within a mixed sample, in certain aspects it is desirable to interrogate the sample for marker loci within the mixed sample, e.g., loci associated with genetic risk or that identify the presence or absence of infectious organisms. Thus, the assay systems provide detection of such marker loci in conjunction with the detection of selected loci for copy number determination in a mixed sample.

Thus, the assay system of the invention can be used to detect polymorphisms in a mixed sample, where such polymorphisms are associated with genes associated with autosomal recessive disorders, mutations associated with autosomal dominant disorders; polymorphisms associated with risk of developing a disease and/or disease progression (e.g., metastasis) and prognosis indicators.

In other specific aspects, the assay system of the invention can be used to detect fetal mutations or polymorphisms in a maternal sample, where such mutations or polymorphisms are associated with polygenic disorders such as coronary heart disease, diabetes, hypertension, congenital heart defects, and epilepsy. Examples include mutations in genes associated with predispositions such as mutations in cancer susceptibility genes, (e.g. mutations ion BRCAI or II or in p53); polymorphisms associated with increased risk of developing later onset diseases, such as the apoE3 gene polymorphism associated with Alzheimer's risk, In addition to detection of chromosomal abnormalities and single gene mutations or polymorphisms associated with monogenic or polygenic disease, disorders or predispositions, the assay systems of the invention may identify infectious agents in the mixed sample.

Selected Amplification

Numerous selective amplification methods can be used to provide the amplified nucleic acids that are analyzed in the assay systems of the invention, and such methods are preferably used to increase the copy numbers of selected loci in a mixed sample in a manner that allows preservation of information concerning the initial content of the selected loci in the mixed sample. Although not all combinations of amplification and analysis are described herein in detail, it is well within the skill of those in the art to utilize different amplification methods and/or analytic tools to isolate and/or analyze the nucleic acids of region consistent with this specification, and such variations will be apparent to one skilled in the art upon reading the present disclosure.

Such amplification methods include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al., Nucleic Acids Res. 20(7):1691-6 (1992), and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some aspects DNA is amplified by multiplex locus-specific PCR. In a preferred aspect the DNA is amplified using adaptor-ligation and single primer PCR. Other available methods of amplification, such as balanced PCR (Makrigiorgos, et al., Nature Biotechnol, 20:936-9 (2002)) and isothermal amplification methods such as nucleic acid sequence based amplification (NASBA) and self-sustained sequence replication (Guatelli et al., PNAS USA 87:1874 (1990)). Based on such methodologies, a person skilled in the art readily can design primers in any suitable regions 5' and 3' to a locus of interest. Such primers may be used to amplify DNA of any length so long that the DNA comprises the selected loci of interest.

The length of an amplified selected locus from a genomic region of interest is long enough to provide enough sequence information to distinguish the amplified locus from other loci that are amplified and/or selected. Generally, an amplified nucleic acid corresponding to a selected locus is at least about 16 nucleotides in length, and more typically, an amplified nucleic acid corresponding to a selected locus is at least about 20 nucleotides in length. In a preferred aspect of the invention, an amplified nucleic acid corresponding to a selected locus is at least about 30 nucleotides in length. In a more preferred aspect of the invention, an amplified nucleic acid corresponding to a selected locus is at least about 32, 40, 45, 50, or 60 nucleotides in length. In other aspects of the invention, an amplified nucleic acid corresponding to a selected locus can be about 100, 150 or up to 200 in length.

In certain aspects, selective amplification comprises an initial linear amplification step, which can be particularly useful if the starting amount of DNA from the mixed sample is quite limited, e.g., where the cell-free DNA in a sample is available in limited quantities. This mechanism increases the amount of DNA molecules that are representative of the original DNA content, and helps to reduce sampling error where accurate quantification of the DNA or a fraction of the DNA (e.g., fetal DNA contribution in a maternal sample) is needed.

Thus, in one aspect, a limited number of cycles of sequence-specific linear amplification are performed on the starting mixed sample comprising cfDNA. The number of cycles is generally less than that used for a typical PCR amplification, e.g., 5-30 cycles or fewer. Primers or probes may be designed to amplify specific genomic segments or regions comprising selected loci. The primers or probes may be modified with an end label at the 5' end (e.g. with biotin) or elsewhere along the primer or probe such that the amplification products can be purified or attached to a solid substrate (e.g., bead or array) for further isolation or analysis. In a preferred aspect, the primers are multiplexed such that a single reaction yields multiple DNA fragments from different regions. Amplification products from the linear amplification could then be further amplified with standard PCR methods or with additional linear amplification.

For example, cfDNA can be isolated from blood, plasma, or serum from a pregnant woman, and incubated with primers against a set number of selected loci that correspond to chromosomes of interest. Preferably, the number of primers used for initial linear amplification will be 12 or more, more preferably 24 or more, more preferably 36 or more, even more preferably 48 or more, and even more preferably 96 or more. Each of the primers corresponds to a single selected locus, and is optionally tagged for identification and/or isolation. A limited number of cycles, preferably 10 or fewer, are performed with linear amplification. The amplification products are subsequently isolated, e.g., when the primers are linked to a biotin molecule the amplification products can be isolated via binding to avidin or streptavidin on a solid substrate. The amplification products are then subjected to further biochemical processes such as further amplification with other primers and/or detection techniques such as sequence determination and hybridization.

Efficiencies of linear amplification may vary between sites and between cycles so that in certain systems normalization may be used to ensure that the products from the linear amplification are representative in frequency and sequence of the nucleic acids in the mixed sample. One practicing the assay system of the invention can utilize information from multiple aliquots of a sample to determine variation in the quantity of different amplification products representing the selected loci, including variation in different selected loci and/or between selected loci following the limited initial linear amplification. Such information can be used to determine the initial levels of selected loci in the sample DNA content, allowing for normalization of the frequency of selected loci.

Universal Amplification

In preferred aspects of the invention, the selectively amplified loci are preferably further amplified through universal amplification of all or substantially all of the various selected loci using the assay systems of the invention. Universal primer regions are added to the fixed sequence oligonucleotides so that the selectively amplified loci may be further amplified in a single universal amplification reaction. These universal primer sequences may be added to the nucleic acids regions during the selective amplification process, i.e., the primers for selective amplification comprise universal primer sequences. Alternatively, adapters comprising universal amplification sequences can be added to the ends of the selectively amplified selected loci as adapters following initial amplification and after isolation of the selectively amplified selected loci from the mixed sample.

In one exemplary aspect, selected lociare initially amplified from a mixed sample using primers complementary to selected loci of interest, followed by a universal amplification step to increase the number of loci for analysis. Introduction of primer regions to the initial amplification products from a mixed sample allows subsequent controlled universal amplification of all or a portion of selected nucleic acids prior to or during analysis, e.g. sequence determination.

Bias and variability can be introduced during DNA amplification, such as that seen during polymerase chain reaction (PCR). In cases where an amplification reaction is multiplexed, there is the potential that different selected loci will amplify at different rates or efficiency. This may be due in part to some primers in a multiplex reaction having better efficiency (i.e. more favorable hybridization kinetics), due to experimental conditions that favor some primers over others such as sequence content of the primer and template DNA, buffer conditions, and other conditions. Universal DNA amplification in a multiplexed assay system generally introduces less bias and variability between amplified loci.

Accordingly, in a one aspect, a small number (e.g., 1-10, preferably 3-5) of cycles of selected amplification using loci specific sequences is performed, followed by universal amplification using universal primers. The number of cycles using universal primers will vary, but will preferably be at least 10 cycles, more preferably at least 5 cycles, even more preferably 20 cycles or more. By moving to universal amplification following a lower number of amplification cycles, the bias of having certain loci amplify at greater rates than others is reduced.

Optionally, the assay system will include a step between the selected amplification process and universal amplification process to remove any nucleic acids that are not selectively amplified in the selective amplification reaction.

The whole product or an aliquot of the product from the selected amplification may be used for the universal amplification reaction. The same or different conditions (e.g., polymerase, buffers, and the like) may be used in the amplification steps, e.g., to ensure that bias and variability are not inadvertently introduced due to experimental conditions. In addition, variations in primer concentrations may be used to differentially limit the number of sequence-specific amplification cycles for some selected loci as compared to other selected loci.

In certain aspects, the universal primer regions of the primers or adapters used in the assay system are designed to be compatible with conventional multiplexed assay methods that utilize general priming mechanisms to analyze large numbers of nucleic acids simultaneously in one reaction in one vessel. Such "universal" priming methods allow for efficient, high volume analysis of the quantity of selected loci present in a mixed sample, and allow for comprehensive quantification of the presence of selected loci within such a mixed sample for the determination of aneuploidy.

Examples of such assay methods include, but are not limited to, multiplexing methods used to amplify and/or genotype a variety of samples simultaneously, such as those described in Oliphant et al., U.S. Pat. No. 7,582,420.

Some aspects utilize coupled reactions for multiplex detection of nucleic acid sequences where oligonucleotides from an early phase of each process contain sequences which may be used by oligonucleotides from a later phase of the process. Exemplary processes for amplifying and/or detecting nucleic acids in samples can be used, alone or in combination, including but not limited to the methods described below, each of which are incorporated by reference in their entirety.

In certain aspects, the assay system of the invention utilizes one of the following combined selective and universal amplification techniques: (1) ligase detection reaction ("LDR") coupled with polymerase chain reaction ("PCR"); (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used by oligonucleotides from a later phase of the process.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe LDR coupled PCR for nucleic acid detection.

Barany et al., U.S. Pat. Nos. 7,556,924 and 6,858,412, describe the use of precircle probes (also called "padlock probes" or "multi-inversion probes") with coupled LDR and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping.

Ronaghi et al., U.S. Pat. No. 7,622,281 describes amplification techniques for labeling and amplifying a nucleic acid using an adapter comprising a unique primer and a barcode.

In a preferred aspect, the amplification products are multiplexed, as described previously. In a preferred aspect, the multiplex amplification products are quantified by analysis of the amplification products. In a preferred aspect, a representational sample of individual molecules from the amplification processes is isolated from the rest of the sample for further analysis. To obtain a representational sample of individual molecules, the average number of molecules per locus must exceed the sampling noise created by the multiplexed reaction. In one aspect, the average number per locus is greater than 100. In another aspect, the average number per locus is greater than 500. In another aspect the average number per locus is greater than 1000.

Individual molecules from the amplification product are preferably isolated physically from the other molecules in a manner that allows the different amplification products to be distinguished from one another in analysis. In a preferred aspect, this isolation occurs on a solid substrate. Each isolated molecule may be associated with a particular identifiable or physical address either prior to analysis, or the address may become known for the particular amplification products based on the outcome of the analysis. The substrate may be a planar surface or three-dimensional surface such as a bead.

Once isolated, the individual amplification product may be further amplified to make multiple identical copies of that molecule at the same known or identifiable location. The amplification may occur before or after that location becomes an identifiable or physical address. The amplification product and/or its copies (which may be identical or complementary to the amplification product) are then analyzed based on the sequence of the amplification product or its copies to identify the particular locus and/or allele it represents.

In a preferred aspect, the entire length of the amplification product or a portion of the amplification product may be analyzed using sequence determination. The number of bases that need to be determined must be sufficient to uniquely identify the amplification product as belonging to a specific locus and/or allele. In one preferred aspect, the locus is analyzed through sequence determination of the amplification product.

Numerous methods of sequence determination are compatible with the assay systems of the inventions. Exemplary methods for sequence determination include, but are not limited to, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Sequence information may be determined using methods that determine many (typically thousands to billions) of nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSee™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

Alternatively, in another aspect, the entire length of the amplification product or a portion of the amplification product may be analyzed using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Variation Minimization within and Between Samples

One challenge with the detection of chromosomal abnormalities by detection in a mixed sample is that the nucleic acids from the minor source may be present in much lower abundance than the nucleic acids from normal the major source. In the case of a maternal sample containing fetal and maternal cfDNA, the cell free fetal DNA as a percentage of the total cfDNA may vary from less than one to forty percent, and most commonly is present at or below twenty percent and frequently at or below ten percent. In the detection of an aneuploidy such as Trisomy 21 (Down Syndrome) in the fetal DNA of such maternal sample, the relative increase in Chromosome 21 is 50% in the fetal DNA and thus as a percentage of the total DNA in a maternal sample where, as an example, the fetal DNA is 5% of the total, the increase in Chromosome 21 as a percentage of the total is 2.5%. If one is to detect this difference robustly through the methods described herein, the variation in the measurement of Chromosome 21 has to be much less than the percent increase of Chromosome 21 contributed by a third chromosome 21 from the fetal DNA.

The variation between levels found between samples and/or for loci within a sample may be minimized by using a combination of analytical methods, many of which are described in this application. For instance, variation is lessened by using an internal reference in the assay. An example of an internal reference is the use of a chromosome present in a "normal" abundance (e.g., disomy for an autosome) to compare against a chromosome present in putatively abnormal abundance, such as aneuploidy, in the same sample. While the use of one such "normal" chromosome as a reference chromosome may be sufficient, it is also possible to use two to many normal chromosomes as the internal reference chromosomes to increase the statistical power of the quantification.

One method of using an internal reference is to calculate a ratio of abundance of the putatively abnormal chromosomes to the abundance of the normal chromosomes in a sample, called a chromosomal ratio. In calculating the chromosomal ratio, the abundance or counts of each of the selected loci for each chromosome are summed together to calculate the total counts for each chromosome. The total counts for one chromosome are then divided by the total counts for a different chromosome to create a chromosomal ratio for those two chromosomes.

Alternatively, a chromosomal ratio for each chromosome may be calculated by first summing the counts of each of the selected loci for each chromosome, and then dividing the sum for one chromosome by the total sum for two or more chromosomes. Once calculated, the chromosomal ratio is then compared to the average chromosomal ratio from a normal population.

The average may be the mean, median, mode or other average, with or without normalization and exclusion of outlier data. In a preferred aspect, the mean is used. In developing the data set for the chromosomal ratio from the normal population, the normal variation of the measured chromosomes is calculated. This variation may be expressed a number of ways, most typically as the coefficient of variation, or CV. When the chromosomal ratio from the sample is compared to the average chromosomal ratio from a normal population, if the chromosomal ratio for the sample falls statistically outside of the average chromosomal ratio for the normal population, the sample contains an aneuploidy. The criteria for setting the statistical threshold to declare an aneuploidy depend upon the variation in the measurement of the chromosomal ratio and the acceptable false positive and false negative rates for the assay. In general, this threshold may be a multiple of the variation observed in the chromosomal ratio. In one example, this threshold is three or more times the variation of the chromosomal ratio. In another example, it is four or more times the variation of the chromosomal ratio. In another example it is five or more times the variation of the chromosomal ratio. In another example it is six or more times the variation of the chromosomal ratio. In the example above, the chromosomal ratio is determined by summing the counts of selected loci by chromosome. Typically, the same number of selected loci for each chromosome is used. An alternative method for generating the chromosomal ratio would be to calculate the average counts for the loci for each chromosome. The average may be any estimate of the mean, median or mode, although typically an average is used. The average may be the mean of all counts or some variation such as a trimmed or weighted average. Once the average counts for each chromosome have been calculated, the average counts for each chromosome may be divided by the other to obtain a chromosomal ratio between two chromosomes, the average counts for each chromosome may be divided by the sum of the averages for all measured chromosomes to obtain a chromosomal ratio for each chromosome as described above. As highlighted above, the ability to detect an aneuploidy in a maternal sample where the putative DNA is in low relative abundance depends greatly on the variation in the measurements of different selected loci in the assay. Numerous analytical methods can be used which reduce this variation and thus improve the sensitivity of this method to detect aneuploidy. One method for reducing variability of the assay is to increase the number of selected loci used to calculate the abundance of the chromosomes. In general, if the measured variation of a single selected locus of a chromosome is X % and Y different selected loci are measured on the same chromosome, the variation of the measurement of the chromosomal abundance calculated by summing or averaging the abundance of each selected locus on that chromosome will be approximately X % divided by $Y^{1/2}$. Stated differently, the variation of the measurement of the chromosome abundance would be approximately the average variation of the measurement of each selected locus' abundance divided by the square root of the number of loci.

In a preferred aspect of this invention, the number of selected loci measured for each chromosome is at least 24. In another preferred aspect of this invention, the number of selected loci measured for each chromosome is at least 48. In another preferred aspect of this invention, the number of selected loci measured for each chromosome is at least 100.

In another preferred aspect of this invention the number of selected loci measured for each chromosome is at least 200. There is incremental cost to measuring each locus and thus it is important to minimize the number of selected loci. In a preferred aspect of this invention, the number of selected loci measured for each chromosome is less than 2000. In a preferred aspect of this invention, the number of selected loci measured for each chromosome is less than 1000. In a most preferred aspect of this invention, the number of selected loci measured for each chromosome is at least 48 and less than 1000. In one aspect, following the measurement of abundance for each selected locus, a subset of the selected loci may be used to determine the presence or absence of aneuploidy. There are many standard methods for choosing the subset of selected loci. These methods include outlier exclusion, where the selected loci with detected levels below and/or above a certain percentile are discarded from the analysis. In one aspect, the percentile may be the lowest and highest 5% as measured by abundance. In another aspect, the percentile may be the lowest and highest 10% as measured by abundance. In another aspect, the percentile may be the lowest and highest 25% as measured by abundance.

Another method for choosing the subset of selected loci includes the elimination of regions that fall outside of some statistical limit. For instance, selected loci that fall outside of one or more standard deviations of the mean abundance may be removed from the analysis. Another method for choosing the subset of selected loci may be to compare the relative abundance of a selected locus to the expected abundance of the same selected locus in a healthy population and discard any selected loci that fail the expectation test. To further minimize the variation in the assay, the number of times each selected locus is measured may be increased. As discussed, in contrast to the random methods of detecting aneuploidy where the genome is measured on average less than once, the assay systems of the present invention intentionally measures each selected locus multiple times. In general, when counting events, the variation in the counting is determined by Poisson statistics, and the counting variation is typically equal to one divided by the square root of the number of counts. In a preferred aspect of the invention, the selected loci are each measured on average at least 100 times. In a preferred aspect to the invention, the selected loci are each measured on average at least 500 times. In a preferred aspect to the invention, the selected loci are each measured on average at least 1000 times. In a preferred aspect to the invention, the selected loci are each measured on average at least 2000 times. In a preferred aspect to the invention, the selected loci are each measured on average at least 5000 times.

In another aspect, subsets of loci can be chosen randomly but with sufficient numbers of selected loci to yield a statistically significant result in determining whether a chromosomal abnormality exists. Multiple analyses of different subsets of loci can be performed within a mixed sample to yield more statistical power. In this example, it may or may not be necessary to remove or eliminate any selected loci prior to the random analysis. For example, if there are 100 selected loci for chromosome 21 and 100 selected loci for chromosome 18, a series of analyses could be performed that evaluate fewer than 100 loci for each of the chromosomes.

In addition to the methods above for reducing variation in the assay, other analytical techniques, many of which are described earlier in this application, may be used in combination. In general, the variation in the assay may be reduced when all of the selected loci for each sample are interrogated in a single reaction in a single vessel. Similarly, the variation in the assay may be reduced when a universal amplification system is used. Furthermore, the variation of the assay may be reduced when the number of cycles of amplification is limited.

Use of Assay Systems for Detection in Mixed Samples from Cancer Patients

The assay system allow the detection of quantitative and qualitative tumor-specific alterations of cfDNA, such as DNA strand integrity, frequency of mutations, abnormalities of microsatellites, and methylation of genes, as diagnostic, prognostic, and monitoring markers in cancer patients. The ability to combine such detection of single gene alterations (including point mutations, indels and copy number variation) with CNV detection provides a powerful method for assisting with clinical diagnosis, treatments, outcome prediction and progression monitoring in patients with or suspected of having a malignancy.

In some aspects, the assay system of the invention is used for diagnostic purposes e.g., to detect the presence and/or nature of a malignancy in a patient or to provide a quantitative estimate of tumor load in a patient. Circulating tumor DNA and microRNAs have been associated with certain cancers, such as lung cancer (Roth C et al., Mol Oncol. 2011 June; 5(3):281-91. Epub 2011 Feb. 24). Copy number variations have also been detected in certain cancers, such as amplified HER2 and estrogen receptor in the cfDNA in breast cancer patients. (Page K., Br J Cancer. 2011 Apr. 12; 104(8):1342-8. Epub 2011 Mar. 22).

In other aspects of the invention, the assay system is used in cancer patients to monitor a response to treatment and/or to follow progress of the disease, e.g., to measure single gene alterations and cfDNA in patients receiving chemoradiotherapy (CRT). For certain cancers, it has been shown that cfDNA integrity index can be significantly and independently associated with tumor response to treatment. Agostini M et al., Ann Surg Oncol. 2011 Mar. 17. Also, the presence or absence of certain genetic alterations and/or differences in copy number variation has been associated with response to chemotherapy and/or prognosis of a disease. See, e.g., Savas S., Acta Oncol. 2010 November; 49(8):1217-26. Epub 2010 Jul. 29, which describes useful genetic variations for determination of treatment response and survival in cancer. For example, the detection of cfDNA levels combined with detection of mutations in the K-RAS gene and/or the p53 gene provide a powerful, relatively non-invasive tool in measuring the prognosis of various cancers, including ovarian cancer, endometrial cancer and lymphomas. Dobrzycka B et al., Ann Oncol. 2011 May; 22(5):1133-40. Epub 2010 Nov. 23; Dobrzycka B et al., Int J Cancer. 2010 Aug. 1; 127(3):612-21; Hosny G et al., Cancer Lett. 2009 Mar. 18; 275(2):234-9. Epub 2008 Nov. 28. Such analysis can be further assisted using tools such as Varietas, a functional database portal for identification of genetic variation and association with treatment outcomes and prognosis. Paananen J et al., Database (Oxford). 2010 Jul. 29; 2010:baq016.

Use of Assay Systems for Detection of Mixed Samples from Transplant Patients

The assay systems of the invention can be used to monitor organ health in a transplant patient using a combination of detection of cfDNA and detection of SNPs or mutations in one or more single genes. Transplanted organs have genomes that are distinct from the genome of a recipient patient, and organ health can be detected using assay system. For example, acute cellular rejection has been shown to be associated with significantly increased levels of cell-free DNA from the donor genome in heart transplant recipients. Snyder™ et al., Proc Natl Acad Sci USA. 2011 Apr. 12; 108(15):6229-34. Epub 2011 Mar. 28. In addition, chemokines and adhesion molecules mediate allograft rejection by recruiting leukocytes into the allograft, and SNPs located in interleukin (IL)-8, CXCR1, CXCR2, have been shown to correlate with allograft outcomes. Ro H. et al., Transplantation. 2011 Jan. 15; 91(1):57-64. Thus, the assay systems of the invention can provide noninvasive tests for monitoring solid organ transplant recipients, and can aid in identification of early signs of rejection without the necessity of organ biopsies or other more onerous diagnostic or prognostic techniques.

Use of Assay Systems for Detection in Maternal Samples

In certain specific aspects, determining the relative percentage of fetal DNA in a maternal sample may be beneficial in analyzing the amplification products, as the percentage of fetal DNA in the sample provides important information on the expected statistical presence of chromosomes, and variation from that expectation may be indicative of fetal aneuploidy. This may be especially helpful in circumstances where the level of fetal DNA in a maternal sample is low, as the percent fetal contribution can be used in determining the quantitative statistical significance in the variations of levels of identified selected loci in a maternal sample. In other aspects, the determining of the relative percent fetal cfDNA in a maternal sample may be beneficial in estimating the level of certainty or power in detecting a fetal aneuploidy.

In some specific aspects, the relative fetal contribution of maternal DNA at the allele of interest can be compared to the paternal contribution at that allele to determine approximate fetal DNA concentration in the sample. In other specific aspects, the relative quantity of solely paternally-derived sequences (e.g., Y-chromosome sequences or paternally-specific polymorphisms) can be used to determine the relative concentration of fetal DNA in a maternal sample.

Another exemplary approach to determining the percent fetal contribution in a maternal sample is through the analysis of DNA fragments with different patterns of DNA methylation between fetal and maternal DNA. In a preferred aspect, the amplified DNA from cell-free DNA is by polymerase chain reaction (PCR). Other mechanisms for amplification can be used as well, including those described in more detail herein, as will be apparent to one skilled in the art upon reading the present disclosure.

In circumstances where the fetus is male, percent fetal DNA in a sample can be determined through detection of Y-specific loci and comparison to calculated maternal DNA content. Quantities of an amplified Y-specific locus, such as a region from the sex-determining region Y gene (SRY), which is located on the Y chromosome and is thus representative of fetal DNA, can be determined from the sample and compared to one or more amplified selected loci which are present in both maternal DNA and fetal DNA and which are preferably not from a chromosome believed to potentially be aneuploid in the fetus, e.g., an autosomal region that is not on chromosome 21 or 18. Preferably, this amplification step is performed in parallel with the selective amplification step, although it may be performed either before or after the selective amplification depending on the nature of the multiplexed assay.

In particular aspects, the percentage of cell-free fetal DNA in a maternal sample can determined by PCR using serially diluted DNA isolated from the maternal sample, which can accurately quantify the number of genomes comprising the amplified genes. PCR using serially diluted DNA isolated from the maternal sample may be preferred when determining percent fetal DNA with a male fetus. For example, if the blood sample contains 100% male fetal DNA, and 1:2 serial dilutions are performed, then on average the Y-linked signal will disappear 1 dilution before the autosomal signal, since there is 1 copy of the Y-linked gene and 2 copies of the autosomal gene.

In a specific aspect, the percentage of free fetal DNA in maternal plasma is calculated for a male fetus using the following formula: percentage of free fetal DNA=(No. of copies of Y-linked gene×2×100)/(No. of copies of autosomal gene), where the number of copies of each gene is determined by observing the highest serial dilution in which the gene was detected. The formula contains a multiplication factor of 2, which is used to normalize for the fact that there is only 1 copy of the Y-linked gene compared to two copies of the autosomal gene in each genome, fetal or maternal.

Determination of Minor Source DNA Content in a Mixed Sample

In certain aspects of the invention, determination of the contribution of DNA form a minor source may be useful in determining copy number variation of loci in those samples. For example, in each maternally-derived sample, the DNA from a fetus will inherit approximately 50% of genetic loci inherited from the mother and 50% of genetic loci from the father. Determining the loci contributed to the fetus from non-maternal sources allows the estimation of fetal DNA in a maternal sample, and thus provides information used to calculate the statistically significant differences in chromosomal frequencies for chromosomes of interest.

In certain aspects, the determination of minor source polymorphisms requires targeted SNP and/or mutation analysis to identify the presence of the minor source DNA in a mixed sample. The information needed for this calculation can be provided using the assay of the invention. In some aspects, the use of prior genotyping is helpful, e.g., genotyping of the donor of a transplant, genotyping of the father and mother in a maternal sample. But generally this information pertaining to the prior genotyping is not necessary prior to performing the assay, and the genotyping is performed simultaneously with the determination of copy number of selected loci within a mixed sample.

In one preferred aspect, the percent minor source nucleic acids in a mixed sample can be quantified using multiplexed SNP detection without using prior genotypic knowledge. In this aspect, two or more selected polymorphic loci with a known SNP in each region are used. In a preferred aspect, the selected polymorphic loci are loci amplified. In a preferred aspect, the amplification is universal. In a preferred embodiment, the selected polymorphic loci are amplified in one reaction in one vessel. Each allele of the selected polymorphic loci in the maternal sample is determined and quantified. In a preferred aspect, high throughput sequencing is used for such determination and quantification. Loci are identified where the major and minor source genotypes are different, e.g., the donor genotype is homozygous and the recipient genotype is heterozygous. This identification is done by observing a high relative frequency of one allele (>80%) and a low relative frequency (<20% and >0.15%) of the other allele for a particular selected locus. The use of multiple loci is particularly advantageous as it reduces the amount of variation in the measurement of the abundance of the alleles. All or a subset of the loci that meet this requirement are used to determine minor source nucleic acid concentration through statistical analysis. In one aspect, concentration is determined by summing the low frequency alleles from two or more loci together, dividing by the sum of the high frequency alleles and multiplying by two. In another aspect, the percent minor source nucleic acid is determined by averaging the low frequency alleles from two or more loci, dividing by the average of the high frequency alleles and multiplying by two.

For many alleles, major and minor source nucleic acid sequences may be homozygous and identical, and as this information is not distinguishing it is not useful in the determination of minor source nucleic acid in a mixed sample. The present invention utilizes allelic information where there is a distinguishable difference between the cell sources (e.g., a fetal allele containing at least one allele that differs from the maternal allele) in calculations of minor source nucleic acid percentages. Data pertaining to allelic regions that are the same for the major and minor source are thus not selected for analysis, or are removed from the pertinent data prior to determination of percentage so as not to swamp out the useful data.

Exemplary methods for quantifying fetal DNA in maternal plasma can be found, e.g., in Chu et al., *Prenat Diagn* 2010; 30:1226-1229, which is incorporated herein by reference.

In one aspect, selected loci may be excluded if the amount or frequency of the region appears to be an outlier due to experimental error, or from idiopathic genetic bias within a particular sample. In another aspect, selected nucleic acids may undergo statistical or mathematical adjustment such as normalization, standardization, clustering, or transformation prior to summation or averaging. In another aspect, selected nucleic acids may undergo both normalization and data experimental error exclusion prior to summation or averaging.

In a preferred aspect, 12 or more loci are used for the analysis. In another preferred aspect, 24 or more loci are used for the analysis. In another preferred aspect, 48 or more loci are used for the analysis. In another aspect, one or more indices are used to identify the sample In a specific aspect, minor source contribution can be quantified using tandem SNP detection. Techniques for identifying tandem SNPs in DNA extracted from, e.g., a maternal sample are disclosed in Mitchell et al, U.S. Pat. No. 7,799,531 and U.S. patent application Ser. Nos. 12/581,070, 12/581,083, 12/689,924, and 12/850,588. These describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample, as described in the Mitchell et al. disclosures, and used to determine the percent fetal contribution in the maternal sample.

As a sample which has not previously been tested for fetal sex has an approximate 50% likelihood that the fetus will be male, Y-specific sequences will only be applicable in half of such samples. In a specific aspect, the polymorphic loci used for determination of fetal source contribution are not on the Y chromosome.

Once the percent cfDNA has been calculated for the minor source, this data may be combined with methods for aneuploidy detection to determine the likelihood that a mixed sample may contain an aneuploidy. In one aspect, an aneuploidy detection method that utilizes analysis of random DNA segments is used, such as that described in, e.g., Quake, U.S. patent application Ser. No. 11/701,686; Shoemaker et al., U.S. patent application Ser. No. 12/230,628. In a preferred aspect, aneuploidy detection methods that utilize analysis of selected loci in a mixed sample include both regions for determination of minor source DNA content as well as non-polymorphic regions from two or more chromosomes to detect a chromosomal abnormality in a single reaction. The single reaction helps to minimize the risk of contamination or bias that may be introduced during various steps in the assay system which may otherwise skew results when utilizing minor source DNA content to help determine the presence or absence of a chromosomal abnormality. In other aspects, a selected locus or regions may be utilized both for determination of minor source DNA content as well as detection of minor source chromosomal abnormalities. Utilizing the same regions for both DNA content and detection of chromosomal abnormalities may further help minimize any bias due to experimental error or contamination.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: General Aspects of the Assay Systems of the Invention

A number of assay formats were tested to demonstrate the ability to perform selective amplification and detection of independent loci to demonstrate multiplexed, ligation-based detection of a large number (e.g., 96 or more) of loci of interest. These loci included loci that were indicative of the presence of a particular chromosome or the presence or absence of a mutation or polymorphism in a particular allele.

These assays were designed based on human genomic sequences, and each interrogation consisted of two fixed sequence oligos per selected locus interrogated in the assay. The first oligo, complementary to the 3' region of a genomic region, comprised the following sequential (5' to 3') oligo elements: a universal PCR priming sequence common to all assays: TACACCGGCGTTATGCGTCGAGAC (SEQ ID NO:1); a nine nucleotide identification index specific to the selected locus; a 9 base locus- or locus/allele-specific sequence that acts as a locus index in the first SNP-independent set and a locus/allele index in the polymorphism-specific second set; a hybridization breaking nucleotide which is different from the corresponding base in the genomic locus; and a 20-24 bp sequence complementary to the selected genomic locus. In cases where a SNP or mutation was detected in this portion of the selected genomic locus, the allele-specific interrogation set consisted of two first fixed sequence tandem ligation primers, each with a different locus/allele index and a different allele-specific base at the SNP position. These first oligos were designed for each selected nucleic acid to provide a predicted uniform $T_m$ with a two degree variation across all interrogations in the assay set.

The second fixed sequence oligo, complementary to the 5' region of the genomic loci, comprised the following sequential (5' to 3') elements: a 20-24b sequence complimentary to the 5' region in the genomic locus; a hybridization breaking nucleotide different from the corresponding base in the genomic locus; and a universal PCR priming sequence which was common to all third oligos in the assay set: ATTGCGGGGACCGATGATCGCGTC (SEQ ID NO:2).

In cases where a SNP or mutation was detected in the selected genomic locus, the allele-specific interrogation set consisted of two tandem ligation primers, each with a different locus/allele index and a different allele-specific base at the mutation/SNP position. This second fixed sequence oligo was designed for each selected nucleic acid to provide a predicted uniform $T_m$ with a two degree variation across all interrogations in the assay set that was substantially the same $T_m$ range as the first oligo set.

In certain tested aspects, one or more bridging oligos were used that were complementary to the genomic locus sequence between the region complementary to the first and second fixed sequence oligos used for each selected locus. In specific aspects tested, more than one bridging oligo was used to span the gap between the fixed sequence oligonucleotides, and the one or more bridging oligo may optionally be designed to identify one or more mutations or SNPs in the sequence. The length of the bridging oligonucleotides used in the assay systems varied from 5 to 36 base pairs.

All oligonucleotides used in the tandem ligation formats were synthesized using conventional solid-phase chemistry. The second fixed sequence oligos and the bridging oligonucleotides were synthesized with 5' phosphate moieties to enable ligation to 3' hydroxyl termini of adjacent oligonucleotides.

Example 2: Preparation of DNA for Use in Tandem Ligation Procedures

Genomic DNA from a Caucasian male (NA12801) or a Caucasian female (NA11995) was obtained from Coriell Cell Repositories (Camden, N.J.) and fragmented by acoustic shearing (Covaris, Woburn, Mass.) to a mean fragment size of approximately 200 bp.

The Coriell DNA was biotinylated using standard procedures. Briefly, the Covaris fragmented DNA was end-repaired by generating the following reaction in a 1.5 ml microtube: 5 µg DNA, 12 µl 10×T4 ligase buffer (Enzymatics, Beverly Mass.), 50 U T4 polynucleotide kinase (Enzymatics, Beverly Mass.), and $H_2O$ to 120 µl. This was incubated at 37° C. for 30 minutes. The DNA was diluted using 10 mM Tris 1 mM EDTA pH 8.5 to desired final concentration of ~2 ng/µl.

5 µl DNA was placed in each well of a 96-well plate, and the plate sealed with an adhesive plate sealer and spun for 10 seconds at 250×g. The plate was then incubated at 95° C. for 3 minutes, cooled to 25° C., and spun again for 10 seconds at 250×g. A biotinylation master mix was prepared in a 1.5 ml microtube to final concentration of: 1×TdT buffer (Enzymatics, Beverly, Mass.), 8 U TdT (Enzymatics, Beverly, Mass.), 250 µM $CoCl_2$, 0.01 nmol/µl biotin-16-dUTP (Roche, Nutley N.J.), and $H_2O$ to 1.5 ml. 15 µl of the master mix was aliquoted into each well of a 96 well plate, and the plate sealed with adhesive plate sealer. The plate was spun for 10 seconds at 250×g and incubated for 37° C. for 60 minutes. Following incubation, the plate was spun again for 10 seconds at 250×g, and 7.5 µl precipitation mix (1 µg/µl Dextran Blue, 3 mM NaOAC) was added to each well.

The plate was sealed with an adhesive plate sealer and mixed using an IKA plate vortexer for 2 minutes at 3000 rpm. 27.5 µl of isopropanol was added into each well, the plate sealed with adhesive plate sealer, and vortexed for 5 minutes at 3000 rpm. The plate was spun for 20 minutes at 3000×g, the supernatant was decanted, and the plate inverted and centrifuged at 10×g for 1 minute onto an absorbent wipe. The plate was air-dried for 5 minutes, and the pellet resuspended in 30 µl 10 mM Tris pH8.0, 1 mM EDTA.

Example 3: Exemplary Assay Formats Using Tandem Ligation

Numerous tandem ligation assay formats using the biotinylated DNA were tested to illustrate proof of concept for the assay systems of the invention, and demonstrated the ability to perform highly multiplexed, targeted detection of a large number of independent loci using the series of different assay formats. The exemplary assay systems of the invention were designed to comprise 96 or more interrogations per loci in a genetic sample, and in cases where SNPs were detected the assay formats utilized 192 or more separate interrogations, each utilizing the detection of different alleles per 96 loci in genetic samples. The examples described for each assay format utilized two different sets of fixed sequence oligonucleotides and/or bridging oligos (as described in Example 1), comprising a total 96 or 192 interrogation reactions for the selected loci depending upon whether or not SNPs were identified.

A first exemplary assay format used locus-specific fixed sequence oligos and bridging oligos, where there was a one base gap between the first fixed sequence oligo and the bridging oligos, and a second one base gap between the bridging oligos and the second fixed sequence oligo. Each of the two gaps encompassed two different SNPs. In this format, a DNA polymerase was used to incorporate each of the SNP bases, and ligase was used to seal the nicks formed thereby. SNP base discrimination derived from the fidelity of base incorporation by the polymerase, and in the event of mis-incorporation, the tendency of ligase to not seal nicks adjacent to mismatched bases.

The second exemplary assay format used two locus-specific fixed sequence oligonucleotides without a bridging oligo, where there was a ~15-35 base gap between the fixed sequence oligos, and where the gap spanned one or more SNPs. In this format, a polymerase was used to incorporate the missing bases of the gap, and a ligase was used to seal the nick formed thereby. SNP base discrimination derived from the fidelity of base incorporation by the polymerase, and in the event of misincorporation, the tendency of ligase to not seal nicks adjacent to mismatched bases.

A third exemplary assay format used allele-specific first and second fixed sequence oligos without a bridging oligo, where there was a ~15-35 base gap between the first and second fixed sequence oligos, and where the gap spanned one or more SNPs. Two separate allele-specific first fixed sequence oligos and two separate allele-specific second fixed sequence oligos were used. A polymerase was used to incorporate the missing bases, and a ligase was used to seal the nick formed thereby. SNP base discrimination derived from hybridization specificity, the tendency of non-proof-reading polymerase to not extend annealed primers with mismatches near the 3' end, and the tendency of the ligase to not seal nicks adjacent to mismatched bases.

A fourth exemplary format used allele-specific fixed sequence oligos and a locus-specific bridging oligo. In this format, two separate fixed sequence oligos complementary to the 3'end of the loci of interest, the first with a 3' base specific for one allele of the targeted SNP, and the second with a 3' base specific for the other allele of the targeted SNP. Similarly, two separate second fixed sequence oligos were used, the first with a 5' base specific for one allele of a second targeted SNP, and the second with a 5' base specific for the other allele of the second targeted SNP. The bridging oligos were complementary to the region directly adjacent to the locus regions complementary to the first and second fixed sequence oligos, and thus no polymerase was needed prior to ligation. Ligase was used to seal the nicks between the fixed sequence oligos and the bridging oligo. SNP base discrimination in this assay format derived from hybridization specificity and the tendency of the ligase to not seal nicks adjacent to mismatched bases. This exemplary format was tested using either T4 ligase or Taq ligase for creation of the contiguous template, and both were proved effective in the reaction as described below.

A fifth exemplary format used locus-specific fixed sequence oligos that were complementary to adjacent regions on the nucleic acid of interest, and thus no gap was created by hybridization of these oligos. In this format, no polymerase was required, and a ligase was used to seal the single nick between the oligos.

A sixth exemplary format used allele-specific fixed sequence oligos and locus-specific bridging oligos, where there was a short base gap of five bases between the loci region complementary to the fixed sequence oligos. The locus-specific bridging oligo in this example was a 5mer complementary to the regions directly adjacent to the regions complementary to the first and second fixed sequence oligos. In this format, no polymerase was required, and a ligase was used to seal the two nicks between the oligos.

A seventh exemplary format used locus-specific fixed sequence oligos and a locus-specific bridging oligo, where there was a shorter base gap of five bases containing a SNP in the region complementary to the bridging oligo. Allele-specific bridging oligos corresponding to the possible SNPs were included in the hybridization and ligation reaction. In this format, no polymerase was required, and a ligase was used to seal the two nicks between the oligos. SNP base discrimination in this assay format derived from hybridization specificity and the tendency of the ligase to not seal nicks adjacent to mismatched bases.

An eighth exemplary format used locus-specific fixed sequence oligos and two adjacent locus-specific bridging oligos, where there was a 10 base gap between the regions complementary to the first and second fixed sequence oligos. Locus-specific bridging oligos were included in the ligation reaction, with the gap requiring two contiguous 5mers to bridge the gap. In this format, no polymerase was required, and a ligase was used to seal the three nicks between the oligos.

For each of the above-described assay formats, an equimolar pool (40 nM each) of sets of first and second loci- or allele-specific fixed sequence oligonucleotides was created from the oligos prepared as set forth in Example 2. A separate equimolar pool (20 µM each) of bridging oligonucleotides was likewise created for the assay processes based on the sequences of the selected genomic loci.

100 µg of strepavidin beads were transferred into the wells of a 96 well plate, and the supernatant was removed. 60 µl BB2 buffer (100 mM Tris pH 8.0, 10 mM EDTA, 500 mM $NaCl_2$, 58% formamide, 0.17% Tween-80), 10 µL 40 nM fixed sequence oligo pool and 30 µL of the biotinylated template DNA prepared in Example 2 were added to the beads. The plate was sealed with an adhesive plate sealer and vortexed at 3000 rpm until beads were resuspended. The oligos were annealed to the template DNA by incubation at 70° C. for 5 minutes, followed by slow cooling to room temperature.

The plate was placed on a raised bar magnetic plate for 2 minutes to pull the magnetic beads and associated DNA to the side of the wells. The supernatant was removed by pipetting, and was replaced with 50 µl of 60% BB2 (v/v in water). The beads were resuspended by vortexing, placed on the magnet again, and the supernatant was removed. This bead wash procedure was repeated once using 50 µl 60% BB2, and repeated twice more using 50 µl wash buffer (10 mM Tris pH 8.0, 1 mM EDTA, 50 mM $NaCl_2$).

The beads were resuspended in 37 µl ligation reaction mix consisting of 1×Taq ligase buffer (Enzymatics, Beverly, Mass.), 1 U Taq ligase, and 2 µM bridging oligo pool (depending on the assay format), and incubated at 37° C. for one hour. Where appropriate, and depending on the assay format, a non-proofreading thermostable polymerase plus 200 nM each dNTP was included in this mixture. The plate was placed on a raised bar magnetic plate for 2 minutes to pull the magnetic beads and associated DNA to the side of the wells. The supernatant was removed by pipetting, and was replaced with 50 µL wash buffer. The beads were resuspended by vortexing, placed on the magnet again, and the supernatant was removed. The wash procedure was repeated once.

To elute the products from the strepavidin beads, 30 µl of 10 mM Tris 1 mM EDTA, pH 8.0 was added to each well of 96-well plate. The plate was sealed and mixed using an IKA vortexer for 2 minutes at 3000 rpm to resuspend the beads. The plate was incubated at 95° C. for 1 minute, and the supernatant aspirated using an 8-channel pipetter. 25 µl of supernatant from each well was transferred into a fresh 96-well plate for universal amplification.

Example 4: Universal Amplification of Tandem Ligated Products

The polymerized and/or ligated nucleic acids were amplified using universal PCR primers complementary to the universal sequences present in the first and second fixed sequence oligos hybridized to the loci of interest. 25 µl of each of the reaction mixtures of Example 3 were used in each amplification reaction. A 50 µl universal PCR reaction consisting of 25 µl eluted ligation product plus 1×PHUSION™ buffer (Finnzymes, Finland), 1M Betaine, 400 nM each dNTP, 1 U PHUSION™ error-correcting thermostable DNA polymerase, and the following primer pairs: TAATGATACGGCGACCACCGAGATCTACACCGGCGT-TATGCGTCGAGA (SEQ ID NO:3) and TCAAGCAGAA-GACGGCATACGAGATXAAACGACGCGATCATCG-GTCCCC GCAA (SEQ ID NO:4), where X represents one of 96 different sample indices used to uniquely identify individual samples prior to pooling and sequencing. The PCR was carried out under stringent conditions using a BioRad TETRAD™ thermocycler.

10 µl of universal PCR product from each of the samples were pooled and the pooled PCR product was purified using AMPureXP™ SPRI beads (Beckman-Coulter, Danvers, Mass.), and quantified using Quant-iT™ PicoGreen, (Invitrogen, Carlsbad, Calif.).

Example 5: Detection and Analysis of Selected Loci

The purified PCR products of each assay format were sequenced on a single lane of a slide on an Illumina HiSeq™ 2000 (Illumina, San Diego, Calif.). Sequencing runs typically give rise to ~100M raw reads, of which ~85M (85%) mapped to expected assay structures. This translated to an average of ~885K reads/sample across the experiment, and (in the case of an experiment using 96 loci) 9.2K reads/replicate/locus across 96 loci. The mapped reads were parsed into replicate/locus/allele counts, and various metrics were computed for each condition, including:

Yield: a metric of the proportion of input DNA that was queried in sequencing, computed as the average number of unique reads per locus (only counting unique identification index reads per replicate/locus) divided by the total number of genomic equivalents contained in the input DNA.

80 percentile locus frequency range: a metric of the locus frequency variability in the sequencing data, interpreted as the fold range that encompasses 80% of the loci. It was computed on the distribution of total reads per locus, across all loci, as the $90^{th}$ percentile of total reads per locus divided by the $10^{th}$ percentile of the total reads per locus.

SNP error rate: a metric of the error rate at the SNP position, and computed as the proportion of reads containing a discordant base at the SNP position.

These results are summarized in Table 1:

TABLE 1

Results Summary of Tandem Ligation Assay Formats

| ASSAY FORMAT | FIXED SEQUENCE OLIGO ($1^{st}$ and/or $2^{nd}$) | BRIDGING OLIGO USED | ENZYME USED | YIELD | 80% LOC FREQ RANGE | SNP ERROR RATE |
|---|---|---|---|---|---|---|
| 1 | LOCUS-SPECIFIC | Locus specific | pol + lig | 9.5% | 5.3 | 0.18% |
| 2 | LOCUS-SPECIFIC | No | pol + lig | 1.4% | 58.3 | 0.19% |
| 3 | ALLELE-SPECIFIC | No | pol + lig | 0.4% | 61.7 | 1.00% |
| 4 | ALLELE-SPECIFIC | Locus specific | Taq lig | 5.0% | 5.9 | 0.92% |
| 4 | ALLELE-SPECIFIC | Locus specific | T4 lig | 5.3% | 4.4 | 0.95% |
| 5 | LOCUS-SPECIFIC | No | Taq lig | 22.5% | 1.7 | N/A |
| 6 | LOCUS-SPECIFIC | Locus specific | Taq lig | 12.5 | 2.9 | N/A |
| 7 | LOCUS-SPECIFIC | Allele specific | Taq lig | 14.3 | 2.8 | 0.20% |
| 8 | LOCUS-SPECIFIC | 2 Locus specific | Taq lig | 18.5% | 2.8 | N/A |

Table 1 indicates that the locus-specific tandem ligation assay using a bridging oligo converted template DNA into targeted product with high yield (~10%), with a high proportion of product derived from targeted loci (15% of reads did not contain expected assay structures), with limited locus bias (80% of loci fall within a ~5-fold concentration range), and with high SNP accuracy (0.2% SNP error rate). The locus-specific tandem ligation assay without the use of a bridging oligo produced reduced yields and substantial locus bias, but still produced high accuracy SNP genotyping data. The allele-specific tandem ligation assay with a bridging oligo produced intermediate yields compared to the locus-specific assay using both T4 and Taq ligase, but still produced limited locus bias and high accuracy SNP genotyping data. The allele-specific tandem ligation assay without a bridging produced reduced yields and substantial locus bias, but still produced high accuracy SNP genotyping data.

Figure 5:
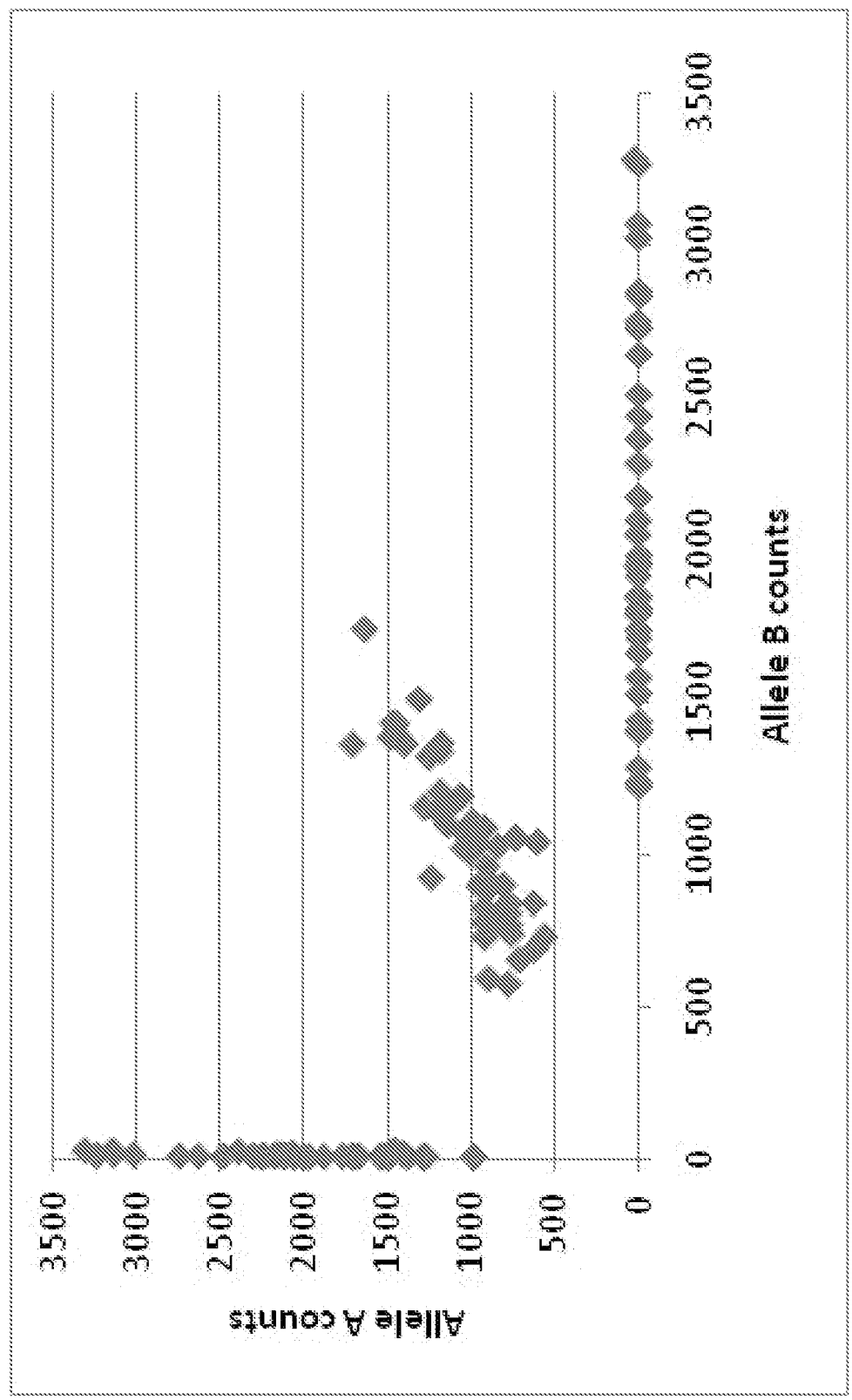
FIG. 5 illustrates the genotyping performance that was obtained using one assay system of the invention.

Assay formats six through eight showed that template DNA can be converted into targeted product with high yield (12-18%), with a high proportion of product derived from targeted loci (~76% of reads contained expected assay structures), and with limited locus bias (80% of loci fall within a 2-3-fold concentration range). FIG. 5 illustrates the genotyping performance that was obtained using assay format seven, comparing the sequence counts for the two alleles of all polymorphic assays observed in a single sample. Note the clear separation of the homozygous and heterozygous clusters, as well as the low background counts observed amongst the homozygous clusters.

Example 6: Determination of Percent Fetal DNA Using Tandem Ligation

One exemplary assay system of the invention was designed to determine percent fetal DNA concentration in a genetic sample as well as to provide counts for selected loci within the sample. This exemplary assay comprised 480 separate interrogations, each utilizing the detection of different loci in a maternal sample. The initial example utilized a determination of percent fetal DNA in subjects carrying a male fetus, and so loci on the Y chromosome were utilized as well as loci containing a paternally-inherited fetal SNP that is different from the maternal sequence.

Specifically, 480 selected nucleic acids were interrogated using the assay system. The 480 selected nucleic acids comprised 48 sequence-specific interrogations of nucleic acids corresponding to loci on chromosome Y, 192 sequence-specific interrogations of nucleic acids corresponding to loci on chromosome 21, 192 sequence-specific interrogations of selected nucleic acids corresponding to loci on chromosome 18, and 144 sequence-specific interrogations of selected nucleic acids corresponding to polymorphic loci on chromosomes 1-16 which. These assays were designed based on human genomic sequences, and each interrogation used three oligos per selected nucleic acid interrogated in the assay.

The first oligo used for each interrogation was complementary to the 3' region of the selected genomic region, and comprised the following sequential (5' to 3') oligo elements: a universal PCR priming sequence common to all assays: TACACCGGCGTTATGCGTCGAGAC (SEQ ID NO:1); an identification index specific to the selected loci comprising nine nucleotides; and a 20-24 bp sequence complementary to the selected genomic locus. This first oligo was designed for each selected nucleic acid to provide a predicted uniform $T_m$ with a two degree variation across all interrogations in the 480 assay set.

The second oligo used for each interrogation was a bridging oligo complementary to the genomic locus sequence directly adjacent to the genomic region complementary to the first oligonucleotide. Based on the selected nucleic acids of interest, the bridging oligos were designed to allow utilization of a total of 12 oligonucleotide sequences that could serve as bridging oligos for all of the 480 interrogations in the assay set.

The third oligo used for each interrogation was complementary to the 5' region of the selected genomic locus, comprised the following sequential (5' to 3') elements: a 20-24b sequence complimentary to the 5' region in the genomic locus; a hybridization breaking nucleotide which was different from the corresponding base in the genomic locus; and a universal PCR priming sequence which was common to all third oligos in the assay set: ATTGCGGGGACCGATGATCGCGTC (SEQ ID NO:2). This third oligo was designed for each selected nucleic acid to provide a predicted uniform $T_m$ with a two degree variation across all interrogations in the 480 assay set, and the $T_m$ range was substantially the same as the $T_m$ range as the first oligo set.

All oligonucleotides were synthesized using conventional solid-phase chemistry. The first and bridging oligonucleotides were synthesized with 5' phosphate moieties to enable ligation to 3' hydroxyl termini of adjacent oligonucleotides. An equimolar pool of sets of the first and third oligonucleotides used for all interrogations in the multiplexed assay was created, and a separate equimolar pool of all bridging oligonucleotides was created to allow for separate hybridization reactions.

Genomic DNA was isolated from 5 mL plasma using the Dynal Silane viral NA kit (Invitrogen, Carlsbad, Calif.). Approximately 12 ng DNA was processed from each of 37 females, including 7 non-pregnant female subjects, 10 female subjects pregnant with males, and 22 female subjects pregnant with females. The DNA was biotinylated using standard procedures, and the biotinylated DNA was immobilized on a solid surface coated with streptavidin to allow retention of the genomic DNA in subsequent assay steps.

The immobilized DNA was hybridized to the first pool comprising the first and third oligos for each interrogated sequences under stringent hybridization conditions. The unhybridized oligos in the pool were then washed from the surface of the solid support, and the immobilized DNA was hybridized to the pool comprising the bridging oligonucleotides under stringent hybridization conditions. Once the bridging oligonucleotides were allowed to hybridize to the immobilized DNA, the remaining unbound oligos were washed from the surface and the three hybridized oligos bound to the selected loci were ligated using T4 ligase to provide a contiguous DNA template for amplification.

The ligated DNA was amplified from the solid substrate using an error correcting thermostable DNA polymerase, a first universal PCR primer TAATGATACGGCGAC-CACCGAGATCTACACCGGCGTTATGCGTCGAGA (SEQ ID NO:3) and a second universal PCR primer TCAAGCAGAAGACGGCAT-ACGAGATXAAACGACGCGATCATCGGTCCC CGCAA (SEQ ID NO:4), where X represents one of 96 different sample indices used to uniquely identify individual samples prior to pooling and sequencing. 10 μL of universal PCR product from each of the 37 samples described above were and the pooled PCR product was purified using AMPure™ SPRI beads (Beckman-Coulter, Danvers, Mass.), and quantified using Quant-iT™ PicoGreen, (Invitrogen, Carlsbad, Calif.).

The purified PCR product was sequenced on 6 lanes of a single slide on an Illumina HiSeq™ 2000. The sequencing run gave rise to 384M raw reads, of which 343M (89%) mapped to expected genomic loci, resulting in an average of 3.8M reads per sample across the 37 samples, and 8K reads per sample per locus across the 480 loci. The mapped reads were parsed into sample and locus counts, and two separate metrics of percent fetal DNA were computed as follows.

Percent male DNA detected by chromosome Y loci corresponds to the relative proportion of reads derived from chromosome Y locus interrogations versus the relative proportion of reads derived from autosomal locus interrogations, and was computed as (number of chromosome Y reads in a test subject/number of autosome reads in test subject)/ (number of reads in male control subject/number of autosome reads in the male control subject). This metric was used as a measure of percent fetal DNA in the case of a male fetus using the relative reads of chromosome Y.

Percent fetal DNA detected by polymorphic loci corresponds to the proportion of reads derived from non-maternal versus maternal alleles at loci where such a distinction can be made. First, for each identified locus, the number of reads for the allele with the fewest counts (the low frequency allele) was divided by the total number of reads to provide a minor allele frequency (MAF) for each locus. Then, loci with an MAF between 0.075% and 15% were identified as informative loci. The estimated percent fetal DNA for the sample was calculated as the mean of the minor allele frequency of the informative loci multiplied by two, i.e. computed as 2× average (MAF) occurrence where 0.075%<MAF<15%.

Figure 6:
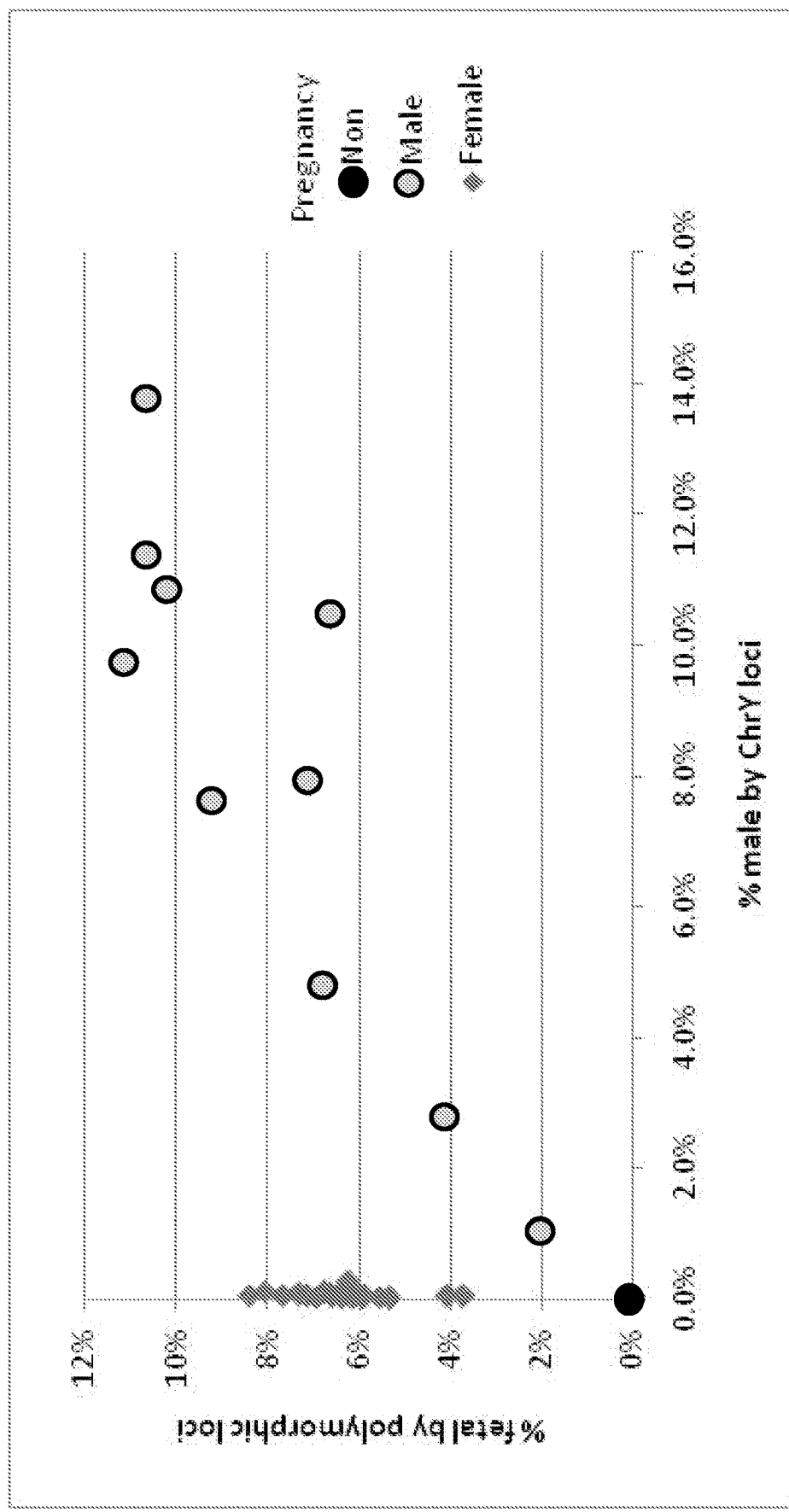
FIG. 6 is a graph illustrating results from a determination of percent fetal using an assay of the invention.

FIG. 6 demonstrates the results from these computations. As shown in FIG. 6, the percent male loci determined using the above-described chromosome Y metrics (grey circles) can separate pregnancies involving male fetuses from pregnancies involving female fetuses (grey diamonds) and non-pregnant samples (black circles). In addition, computation of the percent fetal amount in a sample by polymorphic loci metric can distinguish pregnant samples from non-pregnant samples. Finally, there was a correlation between the percent fetal DNA estimates for a sample obtained from chromosome Y and polymorphic loci in pregnancies involving male fetuses. This correlation persists down to quite low percent fetal values.

Example 7: Detection of Aneuploidy in a Maternal Sample

The assay systems of the invention were used in the detection of polymorphisms and chromosomal abnormalities in two separate cohorts of pregnant females. A first cohort of 190 normal, 36 T21, and 8 T18 pregnancies and a second cohort of 126 normal, 36 T21, and 8 T18 pregnancies were tested for fetal aneuploidy. The chromosomal aneuploidies were detected using 576 chromosome 21 and 576 chromosome 18 assays, pooled together and assayed in a single reaction, as set forth below.

Figure 7:
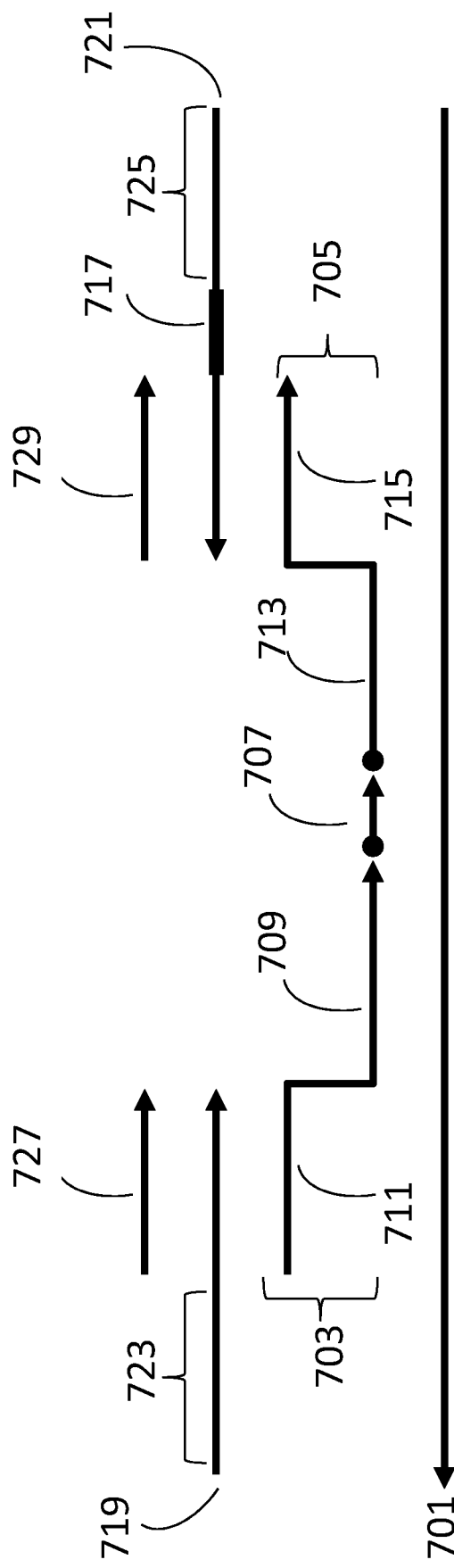
FIG. 7 illustrates the elements used for a detection of aneuploidy and polymorphism for two cohorts of maternal samples.

The elements used in the aneuploidy detection assays are illustrated in FIG. 7. The cfDNA 701 isolated from maternal samples was used as a template for hybridization, ligation, and amplification of multiple selected loci from both chromosome 21 and chromosome 18 in each maternal sample. Three oligonucleotides were hybridized to each selected locus to create ligation products for amplification and detection. The left (or first) fixed sequence oligonucleotide comprised a region complementary to a selected locus 709 and a first universal primer region 711. The right (or second) fixed sequence oligonucleotide 705 comprised a second region complementary to the selected locus 713 and a second universal primer region 715. The bridging oligonucleotides 707 used were designed so that each would hybridize to bridging regions of two or more selected loci used in the aneuploidy detection assay. When the fixed sequence oligonucleotides 703, 705 and the bridging oligonucleotide 707 hybridized to the complementary region on the cfDNA 701, their termini formed two nicks. Upon ligation of the hybridized oligonucleotides to the cfDNA, a ligation product was created for each selected locus comprising 703, 705 and 707 which was used as a template for amplification primers 719, 721.

Two amplification primers 719, 721 comprising regions complementary to the first and second universal primer regions, respectively, were then used to amplify the ligation product. This amplification product comprised the sequence of the selected locus. The right amplification primer also comprised a sample index 717 to identify the particular sample from which the locus was obtained in the multiplexed assay. Amplification with 96 distinct right amplification primers 729 enabled pooling and simultaneous sequencing of 96 different amplification products on a single lane.

The amplification primers 719, 721 also contained a left cluster sequence 723 (TAATGATACGGCGACCACCGA) (SEQ ID NO:7) and a right cluster sequence 725 (ATCTCGTATGCCGTCTTCTGCTTGA)(SEQ ID NO:8) that supported cluster amplification for sequencing using the Illumina HiSeg™ 2000 system (Illumina, San Diego, Calif.). A sequencing primer 727 comprising the first universal primer sequence was used to determine the sequence of the amplification product, and a second sequencing primer 729 was used to determine the sample index 717 of the amplification product.

Briefly, approximately 10 mL peripheral blood was collected from each patient into a BCT® tube (Streck, Omaha, Nebr.), which was shipped via overnight courier to Tandem Diagnostics. Plasma was isolated from BCT® tubes within 72 h of blood collection by centrifugation at 1600 g for 10 m. The plasma was transferred to a second tube and centrifuged at 16000 g for 10 m to remove any remaining cells. cfDNA was isolated from 4-5 mL plasma per patient. Approximately 15 ng cfDNA was isolated from each patient sample and arrayed into individual wells of a 96 well plate. All subsequent processing occurred on multiplexed batches of up to 96 cfDNA patient samples per array system method.

cfDNA isolated from the maternal samples in each well was biotinylated, precipitated and resuspended in 30 μL TE as in Example 3 above. The biotinylated template DNA was mixed with 100 μg MYONE™ C1 streptavidin-coated magnetic beads (Life Technologies, Carlsbad, Calif.), 60 μl BB2 buffer (100 mM Tris pH 8.0, 10 mM EDTA, 500 mM NaCl$_2$, 58% formamide, 0.17% Tween-80), and 10 μL of pooled 40 nM left 703 and right 705 fixed sequence oligonucleotides. The mixture was heated to 70° C., and cooled 2 hours. The beads were then magnetically immobilized to the side of the well, washed twice with 50 μL 60% BB2 (v/v with H$_2$O), washed twice more with 50 μl wash buffer (10 mM Tris pH 8.0, 1 mM EDTA, 50 mM NaCl$_2$), and then resuspended in a 50 μL reaction containing 1 U Taq ligase (Enzymatics, Beverly Mass.), 1× Taq ligase buffer (Enzymatics), and 10 μM of a 5'-phosphorylated 5mer bridging oligonucleotide 707. The mixture was incubated at 37° C. for 1 hour. The beads were again magnetically immobilized to the side of the well, washed twice with 50 wash buffer and then resuspended in 30 μL TE.

The ligation products were eluted from the immobilized beads by incubation at 95° C. for 3 minutes. The eluted ligation products were amplified by 26 cycles of PCR in a 50 μL reaction containing 1 U PHUSION™ polymerase (Thermo Fisher, Waltham Mass.), 1M Betaine, 1×PHU-SION™ buffer, and 400 nM left and right amplification primers (719, 721 respectively). The right primer contained a 7 base sample index (717) that enabled 96 sample multiplexed sequencing on the HISEQ™ 2000 (Illumina, San Diego, Calif.). The sequence of the left fixed sequence oligo was:

(SEQ ID NO: 5)
TAATGATACGGCGACCACCGAGATCTACACCGGCGTTATGCGTCGAGAC.

And the sequence of the right fixed sequence oligo was:

(SEQ ID NO: 6)
TCAAGCAGAAGACGGCATACGAGATNNNNNNNAAACGACGCGATCATCGG
TCCCCGCAAT

Amplification products from a single 96 well plate were pooled in equal volume, and the pooled amplification products were purified with AMPUREXP™ SPRI beads (Beckman-Coulter, Danvers, Mass.) according to the manufacturer's instructions. Each purified pooled library was used as template for cluster amplification on an Illumina TRUSEQ™ v2 SR cluster kit flow cell (Illumina, San Diego, Calif.) according to manufacturer's protocols. The slide was processed on an Illumina HISEQ™ 2000 (Illumina, San Diego, Calif.) to produce 56 bases of locus-specific sequence from a left sequence primer 723 and a separate read of 8 bases of sample specific sequence was obtained from the second sequence primer 725. An average of 903K raw reads per sample were collected. An average of 876K (97%) of the reads was assigned to expected assay structures.

FIG. 8 shows exemplary data for a subset of the patient samples from the second cohort, which were all analyzed in one multiplexed assay on a single lane of a sequencing run. Initially 96 different samples were run in this particular run, but six samples were later excluded from this analytical set as not meeting sample quality control thresholds. A trimmed mean was calculated for each chromosome 18 and chromosome 21 for the samples based on reads produced in the assay. The trimmed mean was computed by removing 10% of high and low counts for each chromosome by sample. The detected amplification products corresponding to the various selected loci were used to compute a chromosome 21 proportion metric and a chromosome 18 proportion metric for each sample. For chromosome 21 proportion, this was calculated as the trimmed mean of counts in the 384 chromosome 21 selected loci divided by the sum of trimmed means of counts for all 576 chromosome 21 loci and 576 chromosome 18 loci for each sample.

On average 834 read counts were observed per selected locus in the maternal samples of the first cohort, and 664 read counts were observed per selected locus from the second cohort. These counts were used to compute chromosome proportion z-scores for chromosome 21 and chromosome 18.

Briefly, the z-scores were calculated by scaling the median per locus count to a common value (e.g., 1000) for each sample, and the scaled counts were transformed by log base 2. An RMA log linear modeling and median polish were performed (Bolstad, B. M et al. (2003) *Bioinformatics* 19(2):185-193; Rafael. A. (2003) *Nucleic Acids Research* 31(4):e15; Irizarry, R A et al. (2003) *Biostatistics* 4(2):249-64) to estimate chromosome effects, locus effects, sample effects, and residuals. The estimated chromosome effects were set to a common value, e.g., 0, and 2^(chromosome effect+sample effect+residual) was calculated for each locus to create normalized counts. The Z scores were scaled using iterative censoring so that they had a mean of 0 and a standard deviation of 1.

Figure 9:
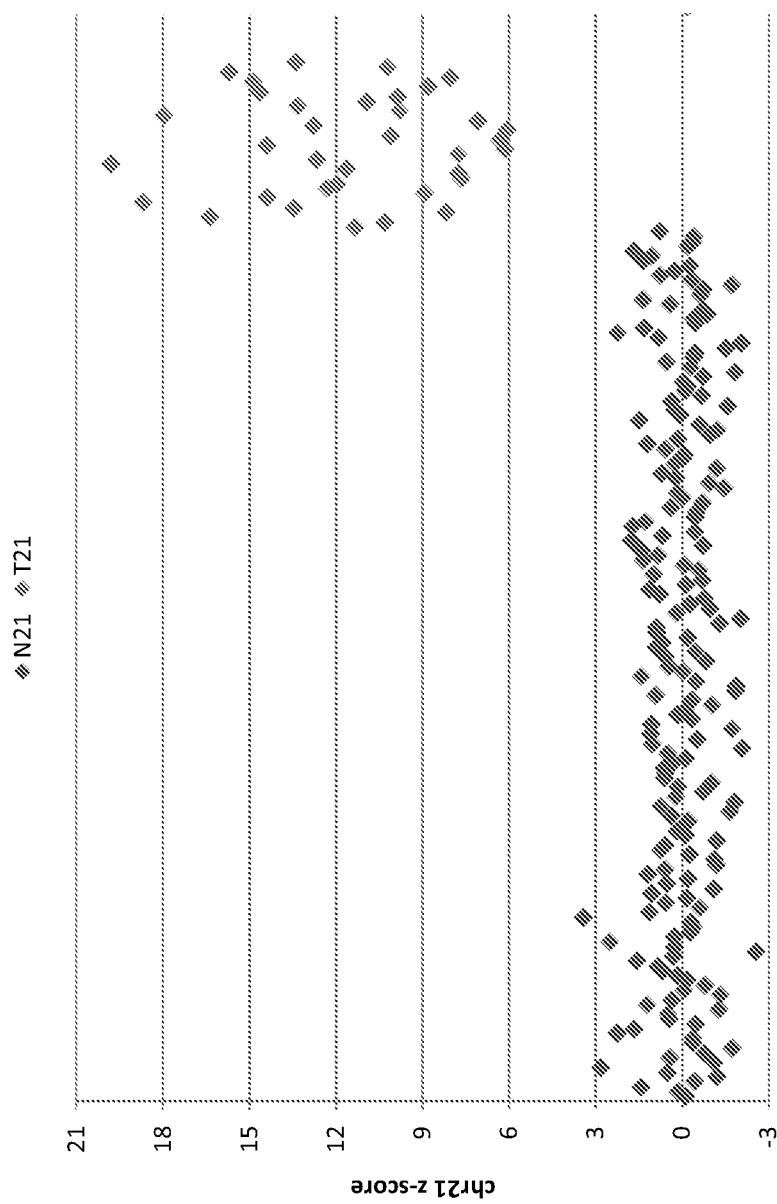
FIG. 9 illustrates the chromosome 21 aneuploidy detection achieved using one aspect of the invention for a first cohort.
Figure 10:
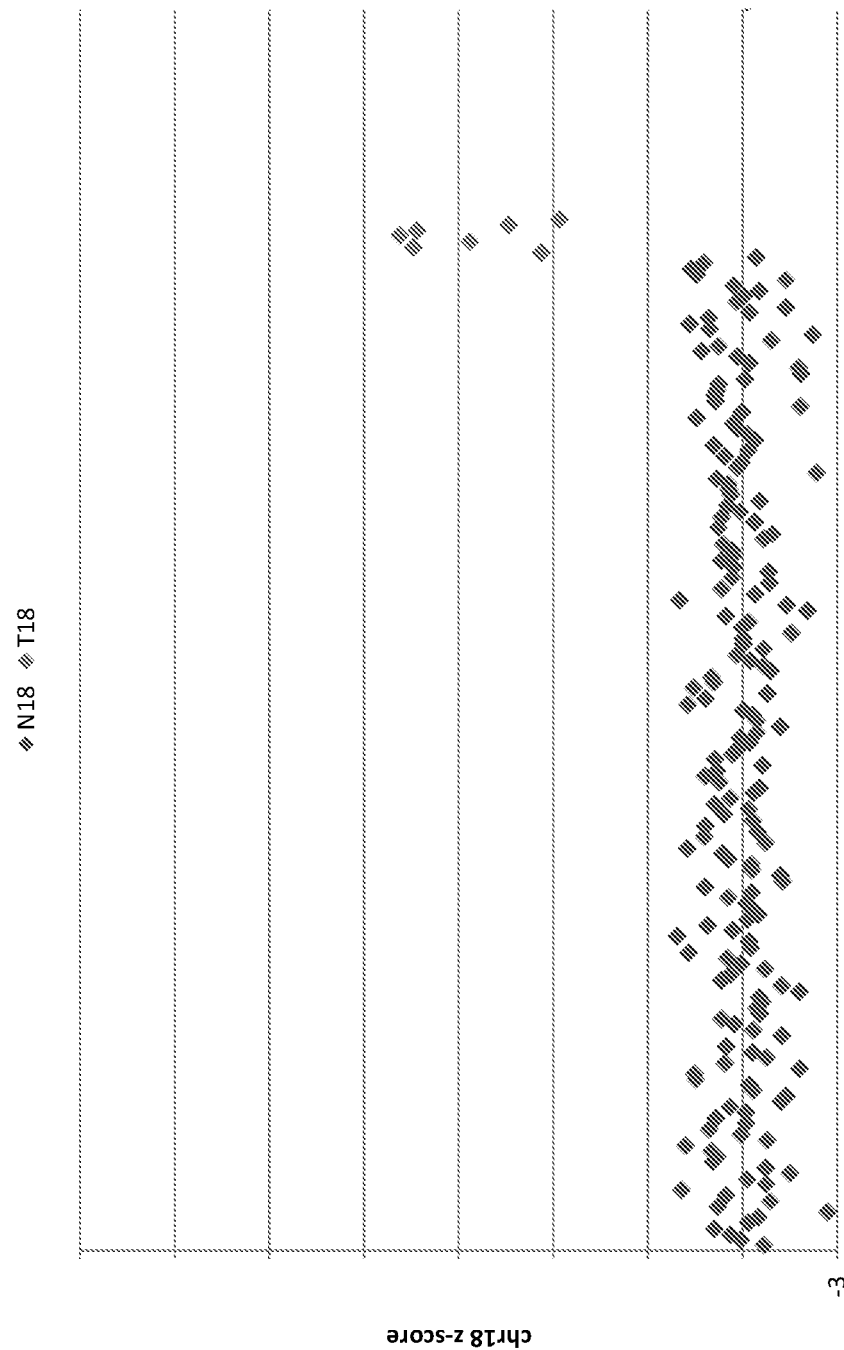
FIG. 10 illustrates the chromosome 18 aneuploidy detection achieved using one aspect of the invention for a first cohort.

Data obtained from the first cohort of samples was used to determine first cohort z-scores for chromosome 21 and chromosome 18 are illustrated in FIGS. 9 and 10, respectively. The normal samples are shown as dark grey diamonds, and the samples with a trisomy are shown as light grey diamonds. 179/180 (99.4%) normal samples (dark grey diamonds) had z-scores <3; one normal sample had a chromosome 21 z-score of 3.4 and a chromosome 18 z-score of 3.0. 35/35 (100%) T21 and 7/7 (100%) T18 samples had chromosome proportion z-scores >3. The mean T18 z-score was 8.5, and the range was 5.8-10.9. The mean T21 z-score was 11.5, and the range was 6.1-19.8.

Figure 11:
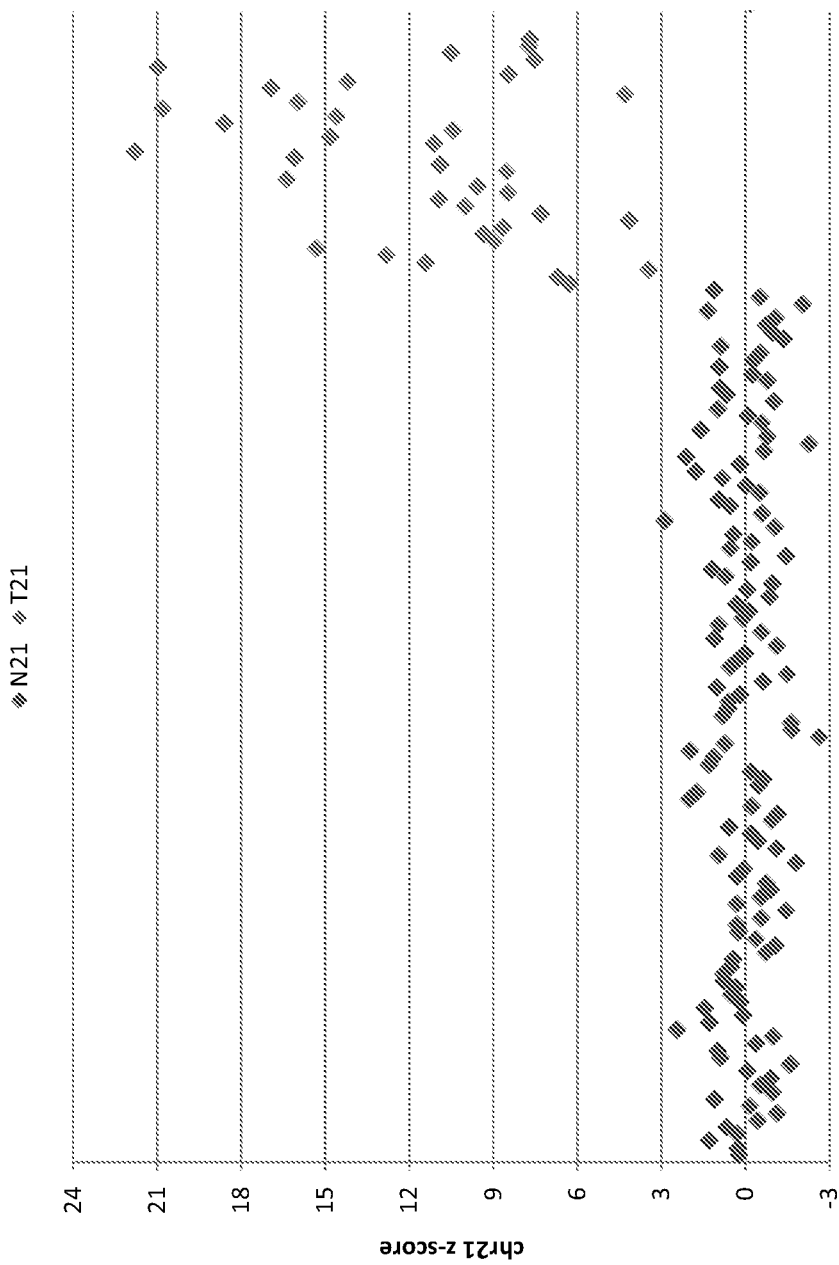
FIG. 11 illustrates the chromosome 21 aneuploidy detection achieved using one aspect of the invention for a second cohort.
Figure 12:
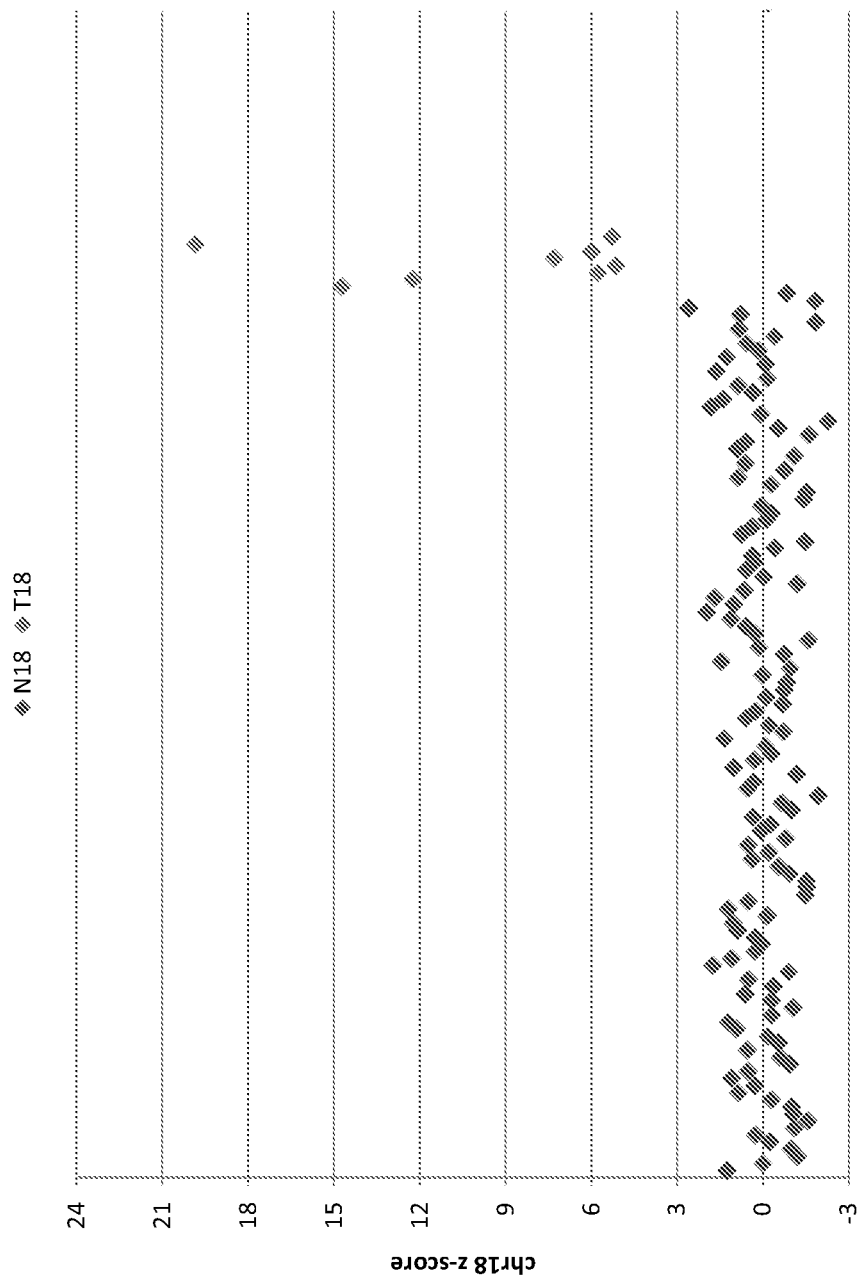
FIG. 12 illustrates the chromosome 18 aneuploidy detection achieved using one aspect of the invention for a second cohort.

The data provided in FIG. 8 was combined with data from the remaining samples of the second cohort to determine z-scores for chromosome 21 and chromosome 18 are illustrated in FIGS. 11 and 12, respectively. The normal samples are shown as dark grey diamonds, and the samples with a trisomy are shown as light grey diamonds. 125/125 normal samples had z-scores <3, 36/36 (100%) T21 and 8/8 (100%) T18 samples had z-scores >3. The mean T18 z-score was 9.5 and the range was 5.1-19.8. The mean T21 z-score was 11.4 and the range was 3.4-21.8.

In addition to the detection of aneuploidy in these cohorts, specific polymorphisms were also used to determine percent fetal contribution to the maternal samples. The general methodology used for determination of these fetal contribution percentages is described in U.S. Ser. No. 61/509,188 filed Jul. 19, 2011, which is incorporated by reference in its entirety.

Briefly, the sequencing of certain loci having detectable polymorphisms identified these loci as informative. The counts of the identified loci having fetal polymorphic regions different from the maternal polymorphic regions were used to calculate the approximate fetal contribution for the maternal sample. Each of the loci used in the calculation of percent fetal contribution to the maternal sample had a minimum of 256 counts. Exemplary SNP data sets for this calculation are illustrated below in Tables 2 and 3. The data corresponding to the identified informative loci from these sets were used in the calculation of percent contribution. The informative loci are shown in each table in bolded text.

TABLE 2

SNP Detection and Calculated Percent Fetal for Maternal Sample 1

| Chromosome/Locus | SNP_1 Counts | SNP_2 Counts | Total Counts | Calculated Percent Fetal |
|---|---|---|---|---|
| Ch01_Lc067487 | 294 | 26 | 320 | 0.210138 |
| Ch01_Lc067489 | 187 | 167 | 354 | |
| Ch01_Lc067490 | 389 | 1 | 390 | |
| Ch01_Lc067491 | 233 | 113 | 346 | |
| Ch01_Lc067492 | 0 | 267 | 267 | |
| Ch01_Lc067493 | 145 | 132 | 277 | |
| Ch01_Lc067495 | 106 | 172 | 278 | |
| Ch01_Lc067496 | 308 | 28 | 336 | |
| Ch01_Lc067497 | 298 | 0 | 298 | |
| Ch01_Lc067498 | 310 | 1 | 311 | |
| Ch01_Lc067499 | 256 | 1 | 257 | |
| Ch01_Lc067501 | 26 | 273 | 299 | |
| Ch01_Lc067503 | 296 | 0 | 296 | |
| Ch01_Lc067504 | 134 | 149 | 283 | |
| Ch02_Lc067508 | 0 | 337 | 337 | |
| Ch02_Lc067510 | 37 | 324 | 361 | |
| Ch02_Lc067511 | 138 | 147 | 285 | |
| Ch02_Lc067512 | 180 | 251 | 431 | |
| Ch02_Lc067514 | 0 | 383 | 383 | |
| Ch02_Lc067515 | 316 | 31 | 347 | |
| Ch02_Lc067516 | 276 | 2 | 278 | |
| Ch02_Lc067519 | 42 | 276 | 318 | |
| Ch02_Lc067521 | 312 | 47 | 359 | |
| Ch02_Lc067522 | 158 | 170 | 328 | |
| Ch02_Lc067523 | 38 | 328 | 366 | |
| Ch02_Lc067524 | 177 | 127 | 304 | |
| Ch02_Lc067525 | 292 | 0 | 292 | |
| Ch02_Lc067526 | 361 | 0 | 361 | |
| Ch02_Lc067527 | 261 | 26 | 287 | |
| Ch02_Lc067529 | 140 | 146 | 286 | |
| Ch03_Lc067530 | 0 | 268 | 268 | |
| Ch03_Lc067531 | 217 | 178 | 395 | |
| Ch03_Lc067532 | 245 | 153 | 398 | |
| Ch03_Lc067533 | 1 | 286 | 287 | |
| Ch03_Lc067534 | 384 | 38 | 422 | |
| Ch03_Lc067535 | 192 | 114 | 306 | |
| Ch03_Lc067537 | 32 | 276 | 308 | |
| Ch03_Lc067538 | 243 | 15 | 258 | |
| Ch03_Lc067539 | 132 | 247 | 379 | |
| Ch03_Lc067540 | 162 | 105 | 267 | |
| Ch03_Lc067541 | 239 | 35 | 274 | |
| Ch03_Lc067542 | 3 | 406 | 409 | |
| Ch03_Lc067544 | 2 | 271 | 273 | |
| Ch03_Lc067545 | 373 | 0 | 373 | |
| Ch03_Lc067546 | 354 | 0 | 354 | |
| Ch03_Lc067547 | 1 | 256 | 257 | |
| Ch03_Lc067548 | 365 | 0 | 365 | |
| Ch03_Lc067549 | 187 | 111 | 298 | |
| Ch04_Lc067550 | 33 | 312 | 345 | |
| Ch04_Lc067552 | 323 | 1 | 324 | |
| Ch04_Lc067553 | 217 | 119 | 336 | |
| Ch04_Lc067557 | 35 | 236 | 271 | |
| Ch04_Lc067558 | 184 | 166 | 350 | |
| Ch04_Lc067559 | 295 | 32 | 327 | |
| Ch04_Lc067560 | 140 | 141 | 281 | |
| Ch04_Lc067561 | 160 | 123 | 283 | |
| Ch04_Lc067562 | 313 | 2 | 315 | |
| Ch04_Lc067566 | 142 | 191 | 333 | |
| Ch04_Lc067569 | 117 | 206 | 323 | |
| Ch05_Lc067570 | 0 | 403 | 403 | |
| Ch05_Lc067571 | 229 | 219 | 448 | |
| Ch05_Lc067572 | 185 | 134 | 319 | |
| Ch05_Lc067573 | 271 | 22 | 293 | |
| Ch05_Lc067575 | 261 | 142 | 403 | |
| Ch05_Lc067578 | 0 | 399 | 399 | |
| Ch05_Lc067579 | 307 | 46 | 353 | |
| Ch05_Lc067581 | 189 | 109 | 298 | |
| Ch05_Lc067582 | 0 | 268 | 268 | |
| Ch05_Lc067583 | 167 | 203 | 370 | |
| Ch05_Lc067585 | 209 | 119 | 328 | |
| Ch05_Lc067586 | 3 | 327 | 330 | |
| Ch05_Lc067587 | 321 | 0 | 321 | |
| Ch06_Lc067589 | 286 | 0 | 286 | |
| Ch06_Lc067590 | 2 | 344 | 346 | |
| Ch06_Lc067591 | 124 | 179 | 303 | |
| Ch06_Lc067592 | 0 | 330 | 330 | |
| Ch06_Lc067593 | 0 | 286 | 286 | |
| Ch06_Lc067594 | 396 | 2 | 398 | |
| Ch06_Lc067595 | 349 | 0 | 349 | |
| Ch06_Lc067597 | 340 | 1 | 341 | |
| Ch06_Lc067598 | 0 | 412 | 412 | |
| Ch06_Lc067599 | 182 | 93 | 275 | |
| Ch06_Lc067600 | 44 | 307 | 351 | |
| Ch06_Lc067601 | 43 | 324 | 367 | |
| Ch06_Lc067602 | 358 | 1 | 359 | |
| Ch07_Lc067603 | 160 | 141 | 301 | |
| Ch07_Lc067604 | 302 | 0 | 302 | |
| Ch07_Lc067605 | 37 | 414 | 451 | |

TABLE 2-continued

SNP Detection and Calculated Percent Fetal for Maternal Sample 1

| Chromosome/Locus | SNP_1 Counts | SNP_2 Counts | Total Counts | Calculated Percent Fetal |
|---|---|---|---|---|
| Ch07_Lc067606 | 269 | 290 | 559 | |
| Ch07_Lc067607 | 166 | 159 | 325 | |
| Ch07_Lc067609 | 1 | 396 | 397 | |
| Ch07_Lc067610 | 225 | 134 | 359 | |
| Ch07_Lc067611 | 48 | 391 | 439 | |
| Ch07_Lc067612 | 2 | 333 | 335 | |
| Ch07_Lc067614 | 200 | 246 | 446 | |
| Ch07_Lc067615 | 188 | 184 | 372 | |
| Ch07_Lc067616 | 167 | 116 | 283 | |
| Ch07_Lc067617 | 204 | 186 | 390 | |
| Ch07_Lc067618 | 281 | 28 | 309 | |
| Ch07_Lc067619 | 44 | 297 | 341 | |
| Ch07_Lc067620 | 336 | 0 | 336 | |
| Ch07_Lc067621 | 48 | 342 | 390 | |
| Ch08_Lc067622 | 313 | 1 | 314 | |
| Ch08_Lc067623 | 414 | 0 | 414 | |
| Ch08_Lc067624 | 230 | 142 | 372 | |
| Ch08_Lc067625 | 0 | 377 | 377 | |
| Ch08_Lc067626 | 41 | 357 | 398 | |
| Ch08_Lc067627 | 133 | 258 | 391 | |
| Ch08_Lc067628 | 388 | 1 | 389 | |
| Ch08_Lc067629 | 348 | 0 | 348 | |
| Ch08_Lc067630 | 37 | 314 | 351 | |
| Ch08_Lc067631 | 185 | 129 | 314 | |
| Ch08_Lc067632 | 49 | 308 | 357 | |
| Ch08_Lc067633 | 186 | 195 | 381 | |
| Ch08_Lc067634 | 174 | 217 | 391 | |
| Ch08_Lc067635 | 161 | 152 | 313 | |
| Ch08_Lc067637 | 0 | 284 | 284 | |
| Ch08_Lc067638 | 343 | 50 | 393 | |
| Ch09_Lc067639 | 164 | 99 | 263 | |
| Ch09_Lc067640 | 185 | 186 | 371 | |
| Ch09_Lc067641 | 344 | 0 | 344 | |
| Ch09_Lc067642 | 294 | 0 | 294 | |
| Ch09_Lc067643 | 36 | 336 | 372 | |
| Ch09_Lc067644 | 221 | 144 | 365 | |
| Ch09_Lc067645 | 315 | 36 | 351 | |
| Ch09_Lc067646 | 141 | 143 | 284 | |
| Ch09_Lc067647 | 33 | 270 | 303 | |
| Ch09_Lc067648 | 43 | 349 | 392 | |
| Ch09_Lc067649 | 147 | 152 | 299 | |
| Ch09_Lc067650 | 201 | 187 | 388 | |
| Ch09_Lc067651 | 176 | 151 | 327 | |
| Ch10_Lc067652 | 29 | 277 | 306 | |
| Ch10_Lc067653 | 134 | 157 | 291 | |
| Ch10_Lc067654 | 174 | 196 | 370 | |
| Ch10_Lc067655 | 189 | 181 | 370 | |
| Ch10_Lc067656 | 125 | 174 | 299 | |
| Ch10_Lc067657 | 375 | 2 | 377 | |
| Ch10_Lc067658 | 0 | 345 | 345 | |
| Ch10_Lc067659 | 204 | 174 | 378 | |
| Ch10_Lc067661 | 236 | 271 | 507 | |
| Ch10_Lc067662 | 39 | 325 | 364 | |
| Ch11_Lc067663 | 2 | 378 | 380 | |
| Ch11_Lc067664 | 42 | 298 | 340 | |
| Ch11_Lc067666 | 196 | 200 | 396 | |
| Ch11_Lc067667 | 220 | 164 | 384 | |
| Ch11_Lc067668 | 20 | 290 | 310 | |
| Ch11_Lc067670 | 1 | 356 | 357 | |
| Ch12_Lc067671 | 212 | 195 | 407 | |
| Ch12_Lc067673 | 1 | 298 | 299 | |
| Ch12_Lc067674 | 242 | 30 | 272 | |
| Ch12_Lc067675 | 2 | 292 | 294 | |
| Ch12_Lc067676 | 1 | 381 | 382 | |
| Ch12_Lc067677 | 139 | 179 | 318 | |

TABLE 3

Sample 2 SNP Detection and Calculated Percent Fetal

| Chromosome/Locus | SNP_1 Counts | SNP_2 Counts | Total Counts | Calculated Percent Fetal |
|---|---|---|---|---|
| Ch01_Lc067487 | 181 | 134 | 315 | 0.096075 |
| Ch01_Lc067489 | 18 | 337 | 355 | |
| Ch01_Lc067490 | 17 | 333 | 350 | |
| Ch01_Lc067491 | 356 | 0 | 356 | |
| Ch01_Lc067492 | 12 | 264 | 276 | |
| Ch01_Lc067493 | 7 | 385 | 392 | |
| Ch01_Lc067494 | 140 | 118 | 258 | |
| Ch01_Lc067495 | 163 | 118 | 281 | |
| Ch01_Lc067496 | 198 | 172 | 370 | |
| Ch01_Lc067498 | 15 | 301 | 316 | |
| Ch01_Lc067499 | 162 | 170 | 332 | |
| Ch01_Lc067501 | 11 | 252 | 263 | |
| Ch01_Lc067502 | 129 | 130 | 259 | |
| Ch01_Lc067503 | 148 | 172 | 320 | |
| Ch01_Lc067504 | 157 | 146 | 303 | |
| Ch02_Lc067508 | 188 | 196 | 384 | |
| Ch02_Lc067510 | 1 | 356 | 357 | |
| Ch02_Lc067511 | 3 | 308 | 311 | |
| Ch02_Lc067512 | 262 | 193 | 455 | |
| Ch02_Lc067513 | 318 | 0 | 318 | |
| Ch02_Lc067514 | 1 | 440 | 441 | |
| Ch02_Lc067515 | 169 | 166 | 335 | |
| Ch02_Lc067516 | 189 | 149 | 338 | |
| Ch02_Lc067519 | 218 | 133 | 351 | |
| Ch02_Lc067521 | 153 | 180 | 333 | |
| Ch02_Lc067522 | 14 | 326 | 340 | |
| Ch02_Lc067523 | 180 | 178 | 358 | |
| Ch02_Lc067524 | 330 | 1 | 331 | |
| Ch02_Lc067526 | 202 | 185 | 387 | |
| Ch02_Lc067527 | 149 | 192 | 341 | |
| Ch02_Lc067529 | 140 | 160 | 300 | |
| Ch03_Lc067530 | 132 | 128 | 260 | |
| Ch03_Lc067531 | 20 | 392 | 412 | |
| Ch03_Lc067532 | 202 | 270 | 472 | |
| Ch03_Lc067533 | 328 | 0 | 328 | |
| Ch03_Lc067534 | 224 | 223 | 447 | |
| Ch03_Lc067535 | 188 | 142 | 330 | |
| Ch03_Lc067537 | 315 | 1 | 316 | |
| Ch03_Lc067538 | 265 | 0 | 265 | |
| Ch03_Lc067539 | 191 | 214 | 405 | |
| Ch03_Lc067540 | 166 | 124 | 290 | |
| Ch03_Lc067542 | 256 | 208 | 464 | |
| Ch03_Lc067543 | 139 | 123 | 262 | |
| Ch03_Lc067544 | 190 | 180 | 370 | |
| Ch03_Lc067545 | 378 | 12 | 390 | |
| Ch03_Lc067546 | 22 | 352 | 374 | |
| Ch03_Lc067547 | 184 | 162 | 346 | |
| Ch03_Lc067548 | 363 | 0 | 363 | |
| Ch03_Lc067549 | 0 | 312 | 312 | |
| Ch04_Lc067550 | 162 | 156 | 318 | |
| Ch04_Lc067552 | 331 | 0 | 331 | |
| Ch04_Lc067553 | 225 | 155 | 380 | |
| Ch04_Lc067555 | 121 | 146 | 267 | |
| Ch04_Lc067557 | 284 | 13 | 297 | |
| Ch04_Lc067558 | 229 | 208 | 437 | |
| Ch04_Lc067559 | 7 | 311 | 318 | |
| Ch04_Lc067560 | 154 | 136 | 290 | |
| Ch04_Lc067561 | 12 | 258 | 270 | |
| Ch04_Lc067562 | 410 | 1 | 411 | |
| Ch04_Lc067566 | 320 | 18 | 338 | |
| Ch04_Lc067569 | 0 | 289 | 289 | |
| Ch05_Lc067570 | 19 | 444 | 463 | |
| Ch05_Lc067571 | 498 | 0 | 498 | |
| Ch05_Lc067572 | 169 | 182 | 351 | |
| Ch05_Lc067573 | 294 | 0 | 294 | |
| Ch05_Lc067575 | 422 | 0 | 422 | |
| Ch05_Lc067578 | 18 | 388 | 406 | |
| Ch05_Lc067579 | 17 | 304 | 321 | |
| Ch05_Lc067580 | 156 | 149 | 305 | |
| Ch05_Lc067581 | 303 | 19 | 322 | |
| Ch05_Lc067583 | 23 | 347 | 370 | |
| Ch05_Lc067585 | 22 | 293 | 315 | |
| Ch05_Lc067586 | 391 | 0 | 391 | |

TABLE 3-continued

Sample 2 SNP Detection and Calculated Percent Fetal

| Chromosome/Locus | SNP_1 Counts | SNP_2 Counts | Total Counts | Calculated Percent Fetal |
|---|---|---|---|---|
| Ch05_Lc067587 | 434 | 1 | 435 | |
| Ch05_Lc067588 | 157 | 129 | 286 | |
| Ch06_Lc067589 | 274 | 0 | 274 | |
| Ch06_Lc067590 | 23 | 320 | 343 | |
| Ch06_Lc067591 | 10 | 342 | 352 | |
| Ch06_Lc067592 | 181 | 177 | 358 | |
| Ch06_Lc067593 | 0 | 296 | 296 | |
| Ch06_Lc067594 | 267 | 200 | 467 | |
| Ch06_Lc067595 | 212 | 201 | 413 | |
| Ch06_Lc067596 | 329 | 12 | 341 | |
| Ch06_Lc067597 | 319 | 1 | 320 | |
| Ch06_Lc067598 | 243 | 186 | 429 | |
| Ch06_Lc067600 | 0 | 341 | 341 | |
| Ch06_Lc067601 | 417 | 0 | 417 | |
| Ch06_Lc067602 | 1 | 340 | 341 | |
| Ch07_Lc067603 | 168 | 185 | 353 | |
| Ch07_Lc067604 | 333 | 11 | 344 | |
| Ch07_Lc067605 | 211 | 287 | 498 | |
| Ch07_Lc067606 | 2 | 542 | 544 | |
| Ch07_Lc067607 | 310 | 0 | 310 | |
| Ch07_Lc067609 | 178 | 189 | 367 | |
| Ch07_Lc067610 | 425 | 0 | 425 | |
| Ch07_Lc067611 | 1 | 449 | 450 | |
| Ch07_Lc067612 | 169 | 149 | 318 | |
| Ch07_Lc067614 | 0 | 446 | 446 | |
| Ch07_Lc067615 | 0 | 427 | 427 | |
| Ch07_Lc067616 | 13 | 278 | 291 | |
| Ch07_Lc067617 | 239 | 246 | 485 | |
| Ch07_Lc067618 | 17 | 267 | 284 | |
| Ch07_Lc067619 | 0 | 335 | 335 | |
| Ch07_Lc067620 | 319 | 0 | 319 | |
| Ch07_Lc067621 | 0 | 354 | 354 | |
| Ch08_Lc067622 | 25 | 232 | 257 | |
| Ch08_Lc067623 | 470 | 0 | 470 | |
| Ch08_Lc067624 | 0 | 376 | 376 | |
| Ch08_Lc067625 | 212 | 202 | 414 | |
| Ch08_Lc067626 | 377 | 0 | 377 | |
| Ch08_Lc067627 | 379 | 16 | 395 | |
| Ch08_Lc067628 | 189 | 210 | 399 | |
| Ch08_Lc067629 | 16 | 338 | 354 | |
| Ch08_Lc067630 | 152 | 153 | 305 | |
| Ch08_Lc067631 | 0 | 379 | 379 | |
| Ch08_Lc067632 | 25 | 355 | 380 | |
| Ch08_Lc067633 | 186 | 236 | 422 | |
| Ch08_Lc067634 | 2 | 375 | 377 | |
| Ch08_Lc067635 | 169 | 159 | 328 | |
| Ch08_Lc067636 | 13 | 274 | 287 | |
| Ch08_Lc067637 | 373 | 11 | 384 | |
| Ch08_Lc067638 | 28 | 431 | 459 | |
| Ch09_Lc067640 | 367 | 0 | 367 | |
| Ch09_Lc067641 | 359 | 0 | 359 | |
| Ch09_Lc067642 | 307 | 1 | 308 | |
| Ch09_Lc067643 | 350 | 32 | 382 | |
| Ch09_Lc067644 | 168 | 241 | 409 | |
| Ch09_Lc067645 | 174 | 179 | 353 | |
| Ch09_Lc067646 | 133 | 177 | 310 | |
| Ch09_Lc067647 | 199 | 188 | 387 | |
| Ch09_Lc067648 | 24 | 450 | 474 | |
| Ch09_Lc067649 | 340 | 0 | 340 | |
| Ch09_Lc067650 | 22 | 348 | 370 | |
| Ch09_Lc067651 | 20 | 365 | 385 | |
| Ch10_Lc067652 | 0 | 292 | 292 | |
| Ch10_Lc067653 | 0 | 279 | 279 | |
| Ch10_Lc067654 | 0 | 396 | 396 | |
| Ch10_Lc067655 | 160 | 170 | 330 | |
| Ch10_Lc067656 | 175 | 121 | 296 | |
| Ch10_Lc067657 | 212 | 188 | 400 | |
| Ch10_Lc067658 | 0 | 356 | 356 | |
| Ch10_Lc067659 | 400 | 13 | 413 | |
| Ch10_Lc067661 | 263 | 268 | 531 | |
| Ch10_Lc067662 | 20 | 324 | 344 | |
| Ch11_Lc067663 | 12 | 357 | 369 | |
| Ch11_Lc067664 | 142 | 179 | 321 | |
| Ch11_Lc067665 | 278 | 0 | 278 | |
| Ch11_Lc067666 | 180 | 232 | 412 | |
| Ch11_Lc067667 | 13 | 438 | 451 | |
| Ch11_Lc067668 | 0 | 365 | 365 | |
| Ch11_Lc067669 | 15 | 263 | 278 | |
| Ch11_Lc067670 | 0 | 374 | 374 | |
| Ch12_Lc067671 | 233 | 183 | 416 | |
| Ch12_Lc067672 | 0 | 269 | 269 | |
| Ch12_Lc067673 | 412 | 11 | 423 | |
| Ch12_Lc067676 | 37 | 436 | 473 | |
| Ch12_Lc067677 | 168 | 197 | 365 | |

The data for these polymorphisms was obtained in the same data set as the aneuploidy data illustrated in FIGS. 11 and 12. Thus, a single assay demonstrated the ability to identify fetal aneuploidy, and the polymorphic differences between fetal and maternal loci allowed the identification of informative loci and calculation of estimated percent fetal cfDNA in the sample based on the informative loci.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed is:

1. An assay for detecting a presence or absence of a fetal copy number variation (CNV) in a genomic region within a maternal sample comprising fetal and maternal cell-free DNA, the assay comprising the steps of:
   (a) hybridizing a first set of fixed sequence oligonucleotides with the maternal and fetal cell-free DNA in the maternal sample, wherein:
      (i) the first set of fixed sequence oligonucleotides comprises first and second fixed sequence oligonucleotides complementary to regions of 24 or more loci in a first genomic region,
      (ii) the first and second fixed sequence oligonucleotides hybridize directly adjacent to each other at each locus or are separated by a gap of one or more nucleotides, and
      (iii) the melting temperatures ($T_m$s) of the first fixed sequence oligonucleotides of the first set of fixed sequence oligonucleotides vary in a range of two degrees centigrade;
   (b) hybridizing a second set of fixed sequence oligonucleotides with the maternal and fetal cell-free DNA in the maternal sample, wherein:
      (i) the second set of fixed sequence oligonucleotides comprises first and second fixed sequence oligonucleotides complementary to regions of 24 or more loci in a second genomic region,
      (ii) the first and second fixed sequence oligonucleotides hybridize directly adjacent to each other at each locus or are separated by a gap of one or more nucleotides, and
      (iii) the $T_m$s of the first fixed sequence oligonucleotides of the second set of fixed sequence oligonucleotides vary in a range of two degrees centigrade;
   (c) when the first and second fixed sequence oligonucleotides of each set are separated by a gap of one or more nucleotides,
      (i) hybridizing bridging oligonucleotides with the maternal and fetal cell-free DNA in the maternal sample, wherein the bridging oligonucleotides are complementary to regions in the loci between the regions complementary to the first and second fixed sequence oligonucleotides of the first and second sets, to create adjacently hybridized oligonucleotides; or
      (ii) extending the first and second fixed sequence oligonucleotides of each set with a polymerase to create adjacently hybridized oligonucleotides;
   (d) ligating the first set of fixed sequence oligonucleotides, the first set of fixed sequence oligonucleotides and the bridging oligonucleotides, or the first set of extended fixed sequence oligonucleotides to create contiguous ligation products complementary to the loci in the first genomic region, and ligating the second set of fixed sequence oligonucleotides, the second set of fixed sequence oligonucleotides and bridging oligonucleotides, or the second set of extended fixed sequence oligonucleotides to create contiguous ligation products complementary to the loci in the second genomic region;
   (e) amplifying each of the contiguous ligation products complementary to the loci in the first genomic region and each of the contiguous ligation products complementary to the loci in the second genomic region to create amplification products;
   (f) detecting the amplification products;
   (g) determining a relative frequency of the loci measured from the first and second genomic regions; and
   (h) detecting the presence or absence of a fetal CNV when the relative frequency of the loci measured from the first genomic region that is different from the relative frequency of the loci measured from the second genomic region.

2. The assay of claim 1, wherein at least one fixed sequence oligonucleotide of each of the first and second sets of fixed sequence oligonucleotides comprises a universal primer region.

3. The assay of claim 2, wherein the first and second sets of fixed sequence oligonucleotides are hybridized prior to hybridization of the bridging oligonucleotides.

4. The assay of claim 1, wherein unhybridized fixed sequence oligonucleotides are removed prior to introduction of the bridging oligonucleotides.

5. The assay of claim 1, wherein the bridging oligonucleotides are hybridized simultaneously with the first and second sets of fixed sequence oligonucleotides.

6. The assay of claim 1, wherein the hybridization products of the first and second sets of fixed sequence oligonucleotides and the complementary loci in the first and second genomic regions are isolated prior to hybridization of the bridging oligonucleotides.

7. The assay of claim 1, wherein the amplification products are isolated as individual molecules prior to detection.

8. The assay of claim 7, wherein the individual isolated amplification products are further amplified to create identical copies of all or a portion of the individual amplification products prior to detection.

9. The assay of claim 7, wherein the individual isolated amplification products are further amplified to create identical copies of molecules complementary to all or a portion of the individual amplification products prior to detection.

10. The assay of claim 1, wherein the first or second oligonucleotide of each set of fixed sequence oligonucleotides comprises a sample index.

11. The assay of claim 1, wherein the amplification products are detected using high throughput sequencing.

12. The assay of claim 11, wherein the high throughput sequencing is nanopore-based sequencing.

13. The assay of claim 1, wherein the first and second genomic regions are chromosomes.

14. The assay of claim 13, wherein the copy number variation is selected from the group consisting of: Down Syndrome (Trisomy 21), Edwards Syndrome (Trisomy 18), Patau Syndrome (Trisomy 13), Klinefelter Syndrome (XXY), Triple X syndrome, XYY syndrome, Trisomy 8, Trisomy 16, Turner Syndrome, Robertsonian translocation, DiGeorge Syndrome, and Wolf-Hirschhorn Syndrome.

15. The assay of claim 13, wherein the chromosome is selected from the group consisting of: chromosome 13, chromosome 18, chromosome 21, the X chromosome, and the Y chromosome.

16. The assay of claim 1, wherein the copy number variation is an amplification or a deletion.

17. The assay of claim 16, wherein the deletion is a deletion of chromosomal region 22q11.

18. The assay of claim 1, further comprising determination of source contribution by a fetal source.

* * * * *